US011903723B2

(12) United States Patent
Barclay et al.

(10) Patent No.: US 11,903,723 B2
(45) Date of Patent: Feb. 20, 2024

(54) ANATOMICAL SURFACE ASSESSMENT METHODS, DEVICES AND SYSTEMS

(71) Applicant: Aranz Healthcare Limited, Christchurch (NZ)

(72) Inventors: Philip John Barclay, Christchurch (NZ); Bruce Leslie Keith Davey, Christchurch (NZ); Brent Stephen Robinson, Christchurch (NZ); Russell William Watson, Christchurch (NZ); Oliver John Dickie, Christchurch (NZ)

(73) Assignee: Aranz Healthcare Limited (NZ)

( * ) Notice: Subject to any disclaimer, the term of this patent is extended or adjusted under 35 U.S.C. 154(b) by 424 days.

(21) Appl. No.: 16/500,785

(22) PCT Filed: Apr. 3, 2018

(86) PCT No.: PCT/IB2018/000447
§ 371 (c)(1),
(2) Date: Oct. 3, 2019

(87) PCT Pub. No.: WO2018/185560
PCT Pub. Date: Oct. 11, 2018

(65) Prior Publication Data
US 2020/0121245 A1  Apr. 23, 2020

Related U.S. Application Data

(60) Provisional application No. 62/481,612, filed on Apr. 4, 2017.

(51) Int. Cl.
*A61B 5/00* (2006.01)
*A61B 5/01* (2006.01)
*A61B 5/107* (2006.01)

(52) U.S. Cl.
CPC ............ *A61B 5/445* (2013.01); *A61B 5/0071* (2013.01); *A61B 5/015* (2013.01); *A61B 5/1075* (2013.01);
(Continued)

(58) Field of Classification Search
CPC ....... A61B 5/445; A61B 5/0071; A61B 5/015; A61B 5/1075; A61B 5/1079; A61B 5/743;
(Continued)

(56) References Cited

U.S. PATENT DOCUMENTS 3,259,612 A   7/1966   Peter
3,335,716 A   8/1967   Alt et al.
(Continued)

FOREIGN PATENT DOCUMENTS

AT     549703      3/2012
CN     110326029   10/2019
(Continued)

OTHER PUBLICATIONS

David N. Mashburn et al., Enabling user-guided segmentation and tracking of surface-labeled cells in time-lapse image sets of living tissues, NIH Public Access, May 1, 2013 (Year: 2013).*
(Continued)

*Primary Examiner* — Sanjay Cattungal
(74) *Attorney, Agent, or Firm* — Perkins Coie LLP

(57) ABSTRACT

Methods for assessing a skin surface of a patient and associated systems and devices are described herein. A method configured in accordance with embodiments of the present technology can include, for example, receiving a three-dimensional data set representative of the patient's skin surface and determining a boundary of a feature of the patient's skin in the three-dimensional data set. The method can further include determining, with a processor, a three- (Continued)

dimensional surface area of the feature within the boundary. In some embodiments, the method can also include identifying a plurality of sub-regions within the boundary and identifying one or more tissue types in each sub-region.

19 Claims, 26 Drawing Sheets

(52) U.S. Cl.
CPC ............ *A61B 5/1079* (2013.01); *A61B 5/743* (2013.01); *A61B 5/7475* (2013.01)

(58) Field of Classification Search
CPC .......... A61B 5/7475; A61B 5/441–447; A61B 6/466; A61B 5/442; A61B 5/0077; A61B 5/7425; A61B 5/7275; A61B 5/0073; A61B 5/1109; A61B 5/6844; A61B 5/1072; A61B 5/1077; A61B 5/444; A61B 5/0059; A61B 5/0064; G06T 7/00; G06T 7/10; G06K 9/624
See application file for complete search history.

(56) References Cited

U.S. PATENT DOCUMENTS

| | | |
|---|---|---|
| 4,090,501 A | 5/1978 | Chaitin |
| 4,170,987 A | 10/1979 | Anselmo et al. |
| 4,236,082 A | 11/1980 | Butler |
| 4,505,583 A | 3/1985 | Konomi |
| 4,515,165 A | 5/1985 | Carroll |
| 4,535,782 A | 8/1985 | Zoltan |
| 4,556,057 A | 12/1985 | Hiruma et al. |
| 4,724,480 A | 2/1988 | Hecker et al. |
| 4,736,739 A | 4/1988 | Flaton |
| 4,768,513 A | 9/1988 | Suzuki |
| 4,773,097 A | 9/1988 | Suzaki et al. |
| 4,821,117 A | 4/1989 | Sekiguchi |
| 4,839,807 A | 6/1989 | Doi et al. |
| 4,851,984 A | 7/1989 | Doi et al. |
| 4,894,547 A | 1/1990 | Leffell et al. |
| 4,930,516 A | 6/1990 | Alfano et al. |
| 4,957,114 A | 9/1990 | Zeng et al. |
| 4,979,815 A | 12/1990 | Tsikos |
| 4,996,994 A | 3/1991 | Steinhauer et al. |
| D315,901 S | 4/1991 | Knowles |
| 5,003,977 A | 4/1991 | Suzuki et al. |
| 5,016,173 A | 5/1991 | Kenet et al. |
| 5,036,853 A | 8/1991 | Jeffcoat et al. |
| 5,080,100 A | 1/1992 | Trotel |
| 5,157,461 A | 10/1992 | Page |
| 5,174,297 A | 12/1992 | Daikuzono |
| 5,241,468 A | 8/1993 | Kenet |
| 5,270,168 A | 12/1993 | Grinnell |
| 5,319,550 A | 6/1994 | Griffith |
| 5,363,854 A | 11/1994 | Martens et al. |
| 5,369,496 A | 11/1994 | Alfano et al. |
| 5,396,331 A | 3/1995 | Kitoh et al. |
| 5,408,996 A | 4/1995 | Salb |
| 5,421,337 A | 6/1995 | Richards-Kortum et al. |
| 5,515,449 A | 5/1996 | Tsuruoka et al. |
| 5,519,208 A | 5/1996 | Esparza et al. |
| 5,528,703 A | 6/1996 | Lee |
| 5,531,520 A | 7/1996 | Grimson et al. |
| 5,532,824 A | 7/1996 | Harvey et al. |
| 5,561,526 A | 10/1996 | Huber et al. |
| 5,588,428 A | 12/1996 | Smith et al. |
| 5,590,660 A | 1/1997 | MacAulay et al. |
| 5,603,318 A | 2/1997 | Heilbrun et al. |
| 5,627,907 A | 5/1997 | Gur et al. |
| 5,644,141 A | 7/1997 | Hooker et al. |
| 5,648,915 A | 7/1997 | McKinney et al. |
| 5,673,300 A | 9/1997 | Reckwerdt et al. |
| 5,689,575 A | 11/1997 | Sako et al. |
| 5,699,798 A | 12/1997 | Hochman et al. |
| 5,701,902 A | 12/1997 | Vari et al. |
| 5,717,791 A | 2/1998 | Labaere et al. |
| D393,068 S | 3/1998 | Kodama |
| 5,740,268 A | 4/1998 | Nishikawa et al. |
| 5,749,830 A | 5/1998 | Kaneko et al. |
| 5,784,162 A | 7/1998 | Cabib et al. |
| 5,791,346 A | 8/1998 | Craine et al. |
| 5,799,100 A | 8/1998 | Clarke et al. |
| 5,810,014 A | 9/1998 | Davis et al. |
| 5,836,872 A * | 11/1998 | Kenet ..................... G06T 7/136 600/306 |
| 5,910,972 A | 6/1999 | Ohkubo et al. |
| 5,921,937 A | 7/1999 | Davis et al. |
| 5,946,645 A | 8/1999 | Rioux et al. |
| 5,957,837 A | 9/1999 | Raab |
| 5,967,797 A | 10/1999 | Maldonado |
| 5,967,979 A | 10/1999 | Taylor et al. |
| 5,969,822 A | 10/1999 | Fright et al. |
| 5,974,165 A | 10/1999 | Giger et al. |
| 6,032,070 A | 2/2000 | Flock et al. |
| 6,081,612 A | 6/2000 | Gutkowicz-Krusin et al. |
| 6,081,739 A | 6/2000 | Lemchen |
| 6,091,995 A | 7/2000 | Ingle et al. |
| 6,101,408 A | 8/2000 | Craine et al. |
| 6,208,749 B1 | 3/2001 | Gutkowicz-Krusin et al. |
| 6,215,893 B1 | 4/2001 | Leshem et al. |
| 6,265,151 B1 | 7/2001 | Canter et al. |
| 6,266,453 B1 | 7/2001 | Hibbard et al. |
| 6,272,278 B1 | 8/2001 | Takahata et al. |
| 6,278,793 B1 | 8/2001 | Gur et al. |
| 6,307,957 B1 | 10/2001 | Gutkowicz-Krusin et al. |
| 6,324,417 B1 | 11/2001 | Cotton |
| D453,350 S | 2/2002 | Fenton |
| 6,359,513 B1 | 3/2002 | Kuo et al. |
| 6,359,612 B1 | 3/2002 | Peter |
| D455,166 S | 4/2002 | Raad |
| 6,381,026 B1 | 4/2002 | Schiff et al. |
| 6,381,488 B1 | 4/2002 | Dickey et al. |
| 6,392,744 B1 | 5/2002 | Holec |
| 6,396,270 B1 | 5/2002 | Smith |
| 6,413,212 B1 | 7/2002 | Raab |
| 6,421,463 B1 | 7/2002 | Poggio et al. |
| 6,427,022 B1 | 7/2002 | Craine et al. |
| 6,491,632 B1 | 12/2002 | Taylor |
| 6,567,682 B1 | 5/2003 | Osterweil et al. |
| 6,594,388 B1 | 7/2003 | Gindele et al. |
| 6,594,516 B1 | 7/2003 | Steckner et al. |
| 6,603,552 B1 | 8/2003 | Cline et al. |
| 6,611,617 B1 | 8/2003 | Crampton |
| 6,611,833 B1 | 8/2003 | Johnson |
| 6,631,286 B2 | 10/2003 | Pfeiffer et al. |
| 6,648,820 B1 | 11/2003 | Sarel |
| 6,671,349 B1 | 12/2003 | Griffith |
| 6,678,001 B1 | 1/2004 | Elberbaum |
| 6,690,964 B2 | 2/2004 | Bieger et al. |
| 6,715,675 B1 | 4/2004 | Rosenfeld |
| 6,754,370 B1 | 6/2004 | Hall-Holt et al. |
| 6,770,186 B2 | 8/2004 | Rosenfeld et al. |
| 6,798,571 B2 | 9/2004 | Wetzel et al. |
| 6,809,803 B1 | 10/2004 | O'Brien et al. |
| 6,810,279 B2 | 10/2004 | Mansfield et al. |
| 6,816,606 B2 | 11/2004 | Wetzel et al. |
| 6,816,847 B1 | 11/2004 | Toyama |
| 6,862,410 B2 | 3/2005 | Miyoshi |
| 6,862,542 B2 | 3/2005 | Lockhart et al. |
| 6,873,340 B2 | 3/2005 | Luby |
| 6,873,716 B1 | 3/2005 | Bowker |
| 6,879,394 B2 | 4/2005 | Amblard et al. |
| 6,907,193 B2 | 6/2005 | Kollias et al. |
| 6,915,073 B2 | 7/2005 | Seo |
| 6,922,523 B2 | 7/2005 | Merola et al. |
| 6,941,323 B1 | 9/2005 | Galperin |
| 6,961,517 B2 | 11/2005 | Merola et al. |
| 6,968,094 B1 | 11/2005 | Gallagher |
| 6,993,169 B2 | 1/2006 | Wetzel et al. |
| 7,006,223 B2 | 2/2006 | Mullani |
| 7,013,172 B2 | 3/2006 | Mansfield et al. |
| 7,015,906 B2 | 3/2006 | Olschewski et al. |

(56) References Cited

U.S. PATENT DOCUMENTS

| | | |
|---|---|---|
| 7,027,153 B2 | 4/2006 | Mullani |
| 7,040,536 B2 | 5/2006 | Rosenfeld |
| 7,054,674 B2 | 5/2006 | Cane et al. |
| 7,064,311 B2 | 6/2006 | Jung et al. |
| 7,068,828 B2 | 6/2006 | Kim et al. |
| 7,068,836 B1 | 6/2006 | Rubbert et al. |
| 7,074,509 B2 | 7/2006 | Rosenfeld et al. |
| 7,103,205 B2 | 9/2006 | Wang et al. |
| 7,106,885 B2 | 9/2006 | Osterweil et al. |
| 7,127,094 B1 | 10/2006 | Elbaum et al. |
| 7,127,280 B2 | 10/2006 | Dauga |
| 7,128,894 B1 | 10/2006 | Tannous et al. |
| 7,130,465 B2 | 10/2006 | Muenzenmayer et al. |
| 7,136,191 B2 | 11/2006 | Kaltenbach et al. |
| D533,555 S | 12/2006 | Odhe et al. |
| 7,155,049 B2 | 12/2006 | Wetzel et al. |
| 7,162,063 B1 | 1/2007 | Craine et al. |
| 7,167,243 B2 | 1/2007 | Mullani |
| 7,167,244 B2 | 1/2007 | Mullani |
| 7,181,363 B2 | 2/2007 | Ratti et al. |
| 7,194,114 B2 | 3/2007 | Schneiderman |
| 7,212,660 B2 | 5/2007 | Wetzel et al. |
| 7,227,621 B2 | 6/2007 | Lee et al. |
| 7,233,693 B2 | 6/2007 | Momma |
| D547,347 S | 7/2007 | Kim |
| 7,248,724 B2 | 7/2007 | Gutenev |
| D554,682 S | 11/2007 | Martinez |
| 7,295,226 B1 | 11/2007 | Meron et al. |
| 7,298,881 B2 | 11/2007 | Giger et al. |
| D561,804 S | 2/2008 | Asai |
| 7,347,365 B2 | 3/2008 | Rowe |
| 7,376,346 B2 | 5/2008 | Merola et al. |
| 7,400,754 B2 | 7/2008 | Jung et al. |
| 7,421,102 B2 | 9/2008 | Wetzel et al. |
| 7,426,319 B2 | 9/2008 | Takahashi |
| 7,440,597 B2 | 10/2008 | Rowe |
| 7,450,783 B2 | 11/2008 | Talapov et al. |
| 7,460,250 B2 | 12/2008 | Keightley et al. |
| 7,474,415 B2 | 1/2009 | Lin et al. |
| 7,487,063 B2 | 2/2009 | Tubic et al. |
| 7,489,799 B2 | 2/2009 | Nilsen et al. |
| 7,495,208 B2 | 2/2009 | Czarnek et al. |
| 7,496,399 B2 | 2/2009 | Maschke |
| 7,509,861 B2 | 3/2009 | Masotti et al. |
| 7,538,869 B2 | 5/2009 | Treado et al. |
| 7,545,963 B2 | 6/2009 | Rowe |
| D597,205 S | 7/2009 | Koch |
| 7,580,590 B2 | 8/2009 | Lin et al. |
| 7,581,191 B2 | 8/2009 | Rice et al. |
| 7,587,618 B2 | 9/2009 | Inui et al. |
| 7,595,878 B2 | 9/2009 | Nelson et al. |
| 7,603,031 B1 | 10/2009 | Viaud et al. |
| D603,441 S | 11/2009 | Wada |
| 7,613,335 B2 | 11/2009 | McLennan et al. |
| 7,620,211 B2 | 11/2009 | Browne et al. |
| 7,647,085 B2 | 1/2010 | Cane et al. |
| 7,668,350 B2 | 2/2010 | Rowe |
| 7,684,589 B2 | 3/2010 | Nilsen et al. |
| 7,724,379 B2 | 5/2010 | Kawasaki et al. |
| 7,729,747 B2 | 6/2010 | Stranc et al. |
| 7,735,729 B2 | 6/2010 | Rowe |
| 7,738,032 B2 | 6/2010 | Kollias et al. |
| 7,751,594 B2 | 7/2010 | Rowe et al. |
| 7,765,487 B2 | 7/2010 | Cable |
| 7,819,311 B2 | 10/2010 | Rowe et al. |
| 7,869,641 B2 | 1/2011 | Wetzel et al. |
| 7,876,948 B2 | 1/2011 | Wetzel et al. |
| 7,881,777 B2 | 2/2011 | Docherty et al. |
| 7,894,645 B2 | 2/2011 | Barsky |
| 7,912,320 B1 | 3/2011 | Minor |
| 7,912,534 B2 | 3/2011 | Grinvald et al. |
| 7,916,834 B2 | 3/2011 | Piorek et al. |
| 7,931,149 B2 | 4/2011 | Gilad et al. |
| 7,951,395 B2 | 5/2011 | Lee et al. |
| 8,000,776 B2 | 8/2011 | Gono |
| 8,019,801 B1 | 9/2011 | Robb et al. |
| 8,026,942 B2 | 9/2011 | Payonk et al. |
| 8,071,242 B2 | 12/2011 | Rosenfeld et al. |
| 8,078,262 B2 | 12/2011 | Murphy et al. |
| 8,094,294 B2 | 1/2012 | Treado et al. |
| 8,105,233 B2 | 1/2012 | Abou El Kheir |
| D653,687 S | 2/2012 | Yu |
| 8,123,704 B2 | 2/2012 | Richards |
| 8,150,500 B2 | 4/2012 | Goldman et al. |
| 8,161,826 B1 | 4/2012 | Taylor |
| 8,165,357 B2 | 4/2012 | Rowe |
| 8,184,873 B2 | 5/2012 | Rowe et al. |
| D662,122 S | 6/2012 | Goodwin |
| D664,655 S | 7/2012 | Daniel et al. |
| 8,213,695 B2 | 7/2012 | Zouridakis |
| 8,218,862 B2 | 7/2012 | Demirli et al. |
| 8,218,873 B2 | 7/2012 | Boncyk et al. |
| 8,218,874 B2 | 7/2012 | Boncyk et al. |
| 8,224,077 B2 | 7/2012 | Boncyk et al. |
| 8,224,078 B2 | 7/2012 | Boncyk et al. |
| 8,224,079 B2 | 7/2012 | Boncyk et al. |
| 8,229,185 B2 | 7/2012 | Ennis et al. |
| 8,238,623 B2 | 8/2012 | Stephan et al. |
| 8,306,334 B2 | 11/2012 | Paschalakis et al. |
| 8,326,031 B2 | 12/2012 | Boncyk et al. |
| 8,335,351 B2 | 12/2012 | Boncyk et al. |
| 8,437,544 B2 | 5/2013 | Boncyk et al. |
| 8,457,395 B2 | 6/2013 | Boncyk et al. |
| 8,463,030 B2 | 6/2013 | Boncyk et al. |
| 8,463,031 B2 | 6/2013 | Boncyk et al. |
| 8,465,762 B2 | 6/2013 | Lee et al. |
| 8,467,600 B2 | 6/2013 | Boncyk et al. |
| 8,467,602 B2 | 6/2013 | Boncyk et al. |
| 8,478,036 B2 | 7/2013 | Boncyk et al. |
| 8,478,037 B2 | 7/2013 | Boncyk et al. |
| 8,480,641 B2 | 7/2013 | Jacobs |
| 8,488,880 B2 | 7/2013 | Boncyk et al. |
| 8,494,264 B2 | 7/2013 | Boncyk et al. |
| 8,498,460 B2 | 7/2013 | Patwardhan |
| 8,520,942 B2 | 8/2013 | Boncyk et al. |
| 8,533,879 B1 | 9/2013 | Taylor |
| 8,548,245 B2 | 10/2013 | Boncyk et al. |
| 8,548,278 B2 | 10/2013 | Boncyk et al. |
| 8,582,817 B2 | 11/2013 | Boncyk et al. |
| 8,588,476 B1 | 11/2013 | Spicola, Jr. |
| 8,588,527 B2 | 11/2013 | Boncyk et al. |
| D697,210 S | 1/2014 | Delaney et al. |
| 8,638,986 B2 | 1/2014 | Jiang et al. |
| 8,661,915 B2 | 3/2014 | Taylor |
| 8,712,193 B2 | 4/2014 | Boncyk et al. |
| 8,718,410 B2 | 5/2014 | Boncyk et al. |
| 8,734,342 B2 | 5/2014 | Cable |
| 8,755,053 B2 | 6/2014 | Fright et al. |
| 8,768,052 B2 | 7/2014 | Kawano |
| 8,773,508 B2 | 7/2014 | Daniel et al. |
| 8,774,463 B2 | 7/2014 | Boncyk et al. |
| 8,787,621 B2 | 7/2014 | Spicola, Sr. et al. |
| 8,787,630 B2 | 7/2014 | Rowe |
| 8,795,169 B2 | 8/2014 | Cosentino et al. |
| 8,798,368 B2 | 8/2014 | Boncyk et al. |
| 8,800,386 B2 | 8/2014 | Taylor |
| 8,814,841 B2 | 8/2014 | Hartwell |
| 8,824,738 B2 | 9/2014 | Boncyk et al. |
| 8,837,868 B2 | 9/2014 | Boncyk et al. |
| 8,842,941 B2 | 9/2014 | Boncyk et al. |
| 8,849,380 B2 | 9/2014 | Patwardhan |
| D714,940 S | 10/2014 | Kim |
| 8,855,423 B2 | 10/2014 | Boncyk et al. |
| 8,861,859 B2 | 10/2014 | Boncyk et al. |
| 8,867,839 B2 | 10/2014 | Boncyk et al. |
| 8,873,891 B2 | 10/2014 | Boncyk et al. |
| 8,875,331 B2 | 11/2014 | Taylor |
| 8,885,983 B2 | 11/2014 | Boncyk et al. |
| 8,892,190 B2 | 11/2014 | Docherty et al. |
| 8,904,876 B2 | 12/2014 | Taylor et al. |
| 8,913,800 B2 | 12/2014 | Rowe |
| 8,923,563 B2 | 12/2014 | Boncyk et al. |
| D720,864 S | 1/2015 | Behar et al. |
| 8,938,096 B2 | 1/2015 | Boncyk et al. |

(56) References Cited

U.S. PATENT DOCUMENTS

| | | |
|---|---|---|
| 8,939,918 B2 | 1/2015 | Richards |
| 8,948,459 B2 | 2/2015 | Boncyk et al. |
| 8,948,460 B2 | 2/2015 | Boncyk et al. |
| D724,216 S | 3/2015 | Gant et al. |
| 8,997,588 B2 | 4/2015 | Taylor |
| 9,014,513 B2 | 4/2015 | Boncyk et al. |
| 9,014,514 B2 | 4/2015 | Boncyk et al. |
| 9,014,515 B2 | 4/2015 | Boncyk, V et al. |
| 9,020,305 B2 | 4/2015 | Boncyk et al. |
| 9,025,813 B2 | 5/2015 | Boncyk et al. |
| 9,025,814 B2 | 5/2015 | Boncyk et al. |
| 9,031,278 B2 | 5/2015 | Boncyk et al. |
| 9,036,947 B2 | 5/2015 | Boncyk et al. |
| 9,036,948 B2 | 5/2015 | Boncyk et al. |
| 9,041,810 B2 | 5/2015 | Ecker et al. |
| D735,879 S | 8/2015 | Behar et al. |
| 9,110,925 B2 | 8/2015 | Boncyk et al. |
| 9,116,920 B2 | 8/2015 | Boncyk et al. |
| 9,135,355 B2 | 9/2015 | Boncyk et al. |
| 9,141,714 B2 | 9/2015 | Boncyk et al. |
| 9,148,562 B2 | 9/2015 | Boncyk et al. |
| D740,945 S | 10/2015 | Booth |
| 9,154,694 B2 | 10/2015 | Boncyk et al. |
| 9,154,695 B2 | 10/2015 | Boncyk et al. |
| 9,167,800 B2 | 10/2015 | Spicola, Jr. |
| 9,179,844 B2 | 11/2015 | Fright et al. |
| 9,186,053 B2 | 11/2015 | Viola |
| 9,196,067 B1 | 11/2015 | Freed |
| 9,224,205 B2 | 12/2015 | Tsin et al. |
| 9,235,600 B2 | 1/2016 | Boncyk et al. |
| 9,244,943 B2 | 1/2016 | Boncyk et al. |
| 9,262,440 B2 | 2/2016 | Boncyk et al. |
| 9,268,197 B1 | 2/2016 | Digregorio et al. |
| 9,285,323 B2 | 3/2016 | Burg et al. |
| 9,288,271 B2 | 3/2016 | Boncyk et al. |
| 9,311,520 B2 | 4/2016 | Burg et al. |
| 9,311,540 B2 | 4/2016 | Ecker et al. |
| 9,311,552 B2 | 4/2016 | Boncyk et al. |
| 9,311,553 B2 | 4/2016 | Boncyk et al. |
| 9,311,554 B2 | 4/2016 | Boncyk et al. |
| 9,317,769 B2 | 4/2016 | Boncyk et al. |
| 9,324,004 B2 | 4/2016 | Boncyk et al. |
| 9,330,326 B2 | 5/2016 | Boncyk et al. |
| 9,330,327 B2 | 5/2016 | Boncyk et al. |
| 9,330,328 B2 | 5/2016 | Boncyk et al. |
| 9,330,453 B2 | 5/2016 | Soldatitsch et al. |
| 9,342,748 B2 | 5/2016 | Boncyk et al. |
| D758,608 S | 6/2016 | Behar et al. |
| 9,377,295 B2 | 6/2016 | Fright et al. |
| 9,395,234 B2 | 7/2016 | Cosentino et al. |
| 9,399,676 B2 | 7/2016 | Schurpf et al. |
| 9,438,775 B2 | 9/2016 | Powers |
| 9,451,928 B2 | 9/2016 | Falco et al. |
| 9,525,867 B2 | 12/2016 | Thomas et al. |
| 9,528,941 B2 | 12/2016 | Burg et al. |
| 9,607,380 B2 | 3/2017 | Burg et al. |
| D783,838 S | 4/2017 | Zhao et al. |
| 9,690,904 B1 | 6/2017 | Zizi |
| 9,808,206 B1 | 11/2017 | Zhao et al. |
| 9,818,193 B2 | 11/2017 | Smart |
| 9,861,285 B2 | 1/2018 | Fright et al. |
| 9,863,811 B2 | 1/2018 | Burg |
| 9,955,910 B2 | 5/2018 | Fright et al. |
| 9,958,383 B2 | 5/2018 | Hall et al. |
| 9,972,077 B2 | 5/2018 | Adiri et al. |
| 9,996,923 B2 | 6/2018 | Thomas |
| 10,013,527 B2 | 7/2018 | Fairbairn et al. |
| D827,827 S | 9/2018 | Canfield et al. |
| 10,068,329 B2 | 9/2018 | Adiri et al. |
| D831,197 S | 10/2018 | Scruggs et al. |
| 10,117,617 B2 | 11/2018 | Cantu et al. |
| 10,130,260 B2 | 11/2018 | Patwardhan |
| 10,143,425 B1 | 12/2018 | Zhao et al. |
| D837,388 S | 1/2019 | Dacosta et al. |
| 10,267,743 B2 | 4/2019 | Burg et al. |
| 10,307,382 B2 | 6/2019 | Jung et al. |
| 10,362,984 B2 | 7/2019 | Adiri et al. |
| 10,368,795 B2 | 8/2019 | Patwardhan |
| 10,559,081 B2 | 2/2020 | Omer et al. |
| RE47,921 E | 3/2020 | Patwardhan |
| D877,931 S | 3/2020 | Dacosta et al. |
| 10,607,340 B2 | 3/2020 | Kim et al. |
| 10,614,623 B2 | 4/2020 | D'alessandro |
| 10,617,305 B2 | 4/2020 | Patwardhan et al. |
| 10,652,520 B2 | 5/2020 | Otto et al. |
| 10,674,953 B2 | 6/2020 | Baker et al. |
| 10,692,214 B2 | 6/2020 | Bisker |
| 10,702,160 B2 | 7/2020 | Patwardhan |
| 10,775,647 B2 | 9/2020 | Joy et al. |
| 10,777,317 B2 | 9/2020 | Fairbairn et al. |
| D898,921 S | 10/2020 | Dacosta et al. |
| D899,604 S | 10/2020 | Dacosta et al. |
| D903,863 S | 12/2020 | Dacosta et al. |
| 10,874,302 B2 | 12/2020 | Fright et al. |
| 10,880,488 B2 | 12/2020 | Tashayyod et al. |
| 10,940,328 B2 | 3/2021 | Lv et al. |
| 11,116,407 B2 | 9/2021 | Dickie et al. |
| 11,134,848 B2 | 10/2021 | Bala et al. |
| 11,138,707 B2 | 10/2021 | Yeo et al. |
| 11,250,945 B2 | 2/2022 | Fairbairn et al. |
| 11,315,245 B2 | 4/2022 | Moore |
| 2002/0054297 A1 | 5/2002 | Lee et al. |
| 2002/0149585 A1 | 10/2002 | Kacyra et al. |
| 2002/0197600 A1 | 12/2002 | Maione et al. |
| 2003/0004405 A1 | 1/2003 | Townsend et al. |
| 2003/0006770 A1 | 1/2003 | Smith |
| 2003/0031383 A1 | 2/2003 | Gooch |
| 2003/0036751 A1 | 2/2003 | Anderson et al. |
| 2003/0085908 A1 | 5/2003 | Luby |
| 2003/0164841 A1 | 9/2003 | Myers |
| 2003/0164875 A1 | 9/2003 | Myers |
| 2003/0229514 A2 | 12/2003 | Brown |
| 2003/0231793 A1 | 12/2003 | Crampton |
| 2004/0013292 A1* | 1/2004 | Raunig ............... G06T 7/0012 |
| | | 382/128 |
| 2004/0014165 A1 | 1/2004 | Keidar et al. |
| 2004/0059199 A1 | 3/2004 | Thomas et al. |
| 2004/0080497 A1 | 4/2004 | Enmei |
| 2004/0117343 A1 | 6/2004 | Johnson |
| 2004/0136579 A1 | 7/2004 | Gutenev |
| 2004/0146290 A1 | 7/2004 | Kollias et al. |
| 2004/0201694 A1 | 10/2004 | Gartstein et al. |
| 2004/0225222 A1 | 11/2004 | Zeng et al. |
| 2004/0264749 A1 | 12/2004 | Skladnev et al. |
| 2005/0012817 A1 | 1/2005 | Hampapur et al. |
| 2005/0027567 A1 | 2/2005 | Taha |
| 2005/0033142 A1 | 2/2005 | Madden et al. |
| 2005/0084176 A1 | 4/2005 | Talapov et al. |
| 2005/0094262 A1 | 5/2005 | Spediacci et al. |
| 2005/0111757 A1 | 5/2005 | Brackett et al. |
| 2005/0154276 A1 | 7/2005 | Barducci et al. |
| 2005/0190988 A1 | 9/2005 | Feron |
| 2005/0237384 A1 | 10/2005 | Jess et al. |
| 2005/0259281 A1 | 11/2005 | Boust |
| 2005/0273011 A1 | 12/2005 | Hattery et al. |
| 2005/0273267 A1 | 12/2005 | Maione |
| 2006/0008178 A1 | 1/2006 | Seeger et al. |
| 2006/0012802 A1 | 1/2006 | Shirley |
| 2006/0036135 A1 | 2/2006 | Kern |
| 2006/0036156 A1 | 2/2006 | Lachaine et al. |
| 2006/0044546 A1 | 3/2006 | Lewin et al. |
| 2006/0055943 A1 | 3/2006 | Kawasaki et al. |
| 2006/0058665 A1 | 3/2006 | Chapman |
| 2006/0072122 A1 | 4/2006 | Hu et al. |
| 2006/0073132 A1 | 4/2006 | Congote |
| 2006/0089553 A1 | 4/2006 | Cotton |
| 2006/0098876 A1 | 5/2006 | Buscema |
| 2006/0135953 A1 | 6/2006 | Kania et al. |
| 2006/0151601 A1 | 7/2006 | Rosenfeld |
| 2006/0159341 A1* | 7/2006 | Pekar ............... G06T 7/149 |
| | | 382/173 |
| 2006/0204072 A1 | 9/2006 | Wetzel et al. |
| 2006/0210132 A1 | 9/2006 | Christiansen et al. |
| 2006/0222263 A1 | 10/2006 | Carlson |

(56) References Cited

U.S. PATENT DOCUMENTS

| | | |
|---|---|---|
| 2006/0268148 A1 | 11/2006 | Kollias et al. |
| 2006/0269125 A1 | 11/2006 | Kalevo et al. |
| 2006/0293613 A1 | 12/2006 | Fatehi et al. |
| 2007/0065009 A1 | 3/2007 | Ni et al. |
| 2007/0097381 A1 | 5/2007 | Tobiason et al. |
| 2007/0125390 A1 | 6/2007 | Afriat et al. |
| 2007/0129602 A1 | 6/2007 | Bettesh et al. |
| 2007/0229850 A1 | 10/2007 | Herber |
| 2007/0273894 A1 | 11/2007 | Johnson |
| 2007/0276195 A1 | 11/2007 | Xu et al. |
| 2007/0276309 A1 | 11/2007 | Xu et al. |
| 2008/0006282 A1 | 1/2008 | Sukovic |
| 2008/0021329 A1 | 1/2008 | Wood et al. |
| 2008/0045807 A1 | 2/2008 | Psota et al. |
| 2008/0088704 A1 | 4/2008 | Wendelken et al. |
| 2008/0098322 A1 | 4/2008 | Champion et al. |
| 2008/0126478 A1 | 5/2008 | Ferguson et al. |
| 2008/0165357 A1 | 7/2008 | Stem |
| 2008/0232679 A1 | 9/2008 | Hahn |
| 2008/0246759 A1 | 10/2008 | Summers |
| 2008/0275315 A1 | 11/2008 | Oka et al. |
| 2008/0285056 A1 | 11/2008 | Blayvas |
| 2008/0312642 A1 | 12/2008 | Kania et al. |
| 2008/0312643 A1 | 12/2008 | Kania et al. |
| 2009/0116712 A1 | 5/2009 | Al-Moosawi et al. |
| 2009/0118720 A1 | 5/2009 | Black et al. |
| 2009/0221874 A1 | 9/2009 | Vinther |
| 2009/0225333 A1 | 9/2009 | Bendall |
| 2009/0234313 A1 | 9/2009 | Mullejeans et al. |
| 2010/0004564 A1 | 1/2010 | Jendle |
| 2010/0020164 A1 | 1/2010 | Perrault |
| 2010/0091104 A1 | 4/2010 | Sprigle et al. |
| 2010/0111387 A1 | 5/2010 | Christiansen, II et al. |
| 2010/0113940 A1 | 5/2010 | Sen et al. |
| 2010/0121201 A1* | 5/2010 | Papaioannou ......... A61B 5/445 600/477 |
| 2010/0149551 A1 | 6/2010 | Malinkevich |
| 2010/0156921 A1 | 6/2010 | McLennan et al. |
| 2010/0191126 A1 | 7/2010 | Al-Moosawi et al. |
| 2010/0278312 A1 | 11/2010 | Ortiz |
| 2011/0032349 A1 | 2/2011 | San Matias et al. |
| 2011/0102550 A1 | 5/2011 | Daniel et al. |
| 2011/0125028 A1 | 5/2011 | Wood et al. |
| 2011/0190637 A1 | 8/2011 | Knobel et al. |
| 2012/0035469 A1 | 2/2012 | Whelan et al. |
| 2012/0059266 A1 | 3/2012 | Davis et al. |
| 2012/0078088 A1 | 3/2012 | Whitestone et al. |
| 2012/0078113 A1 | 3/2012 | Whitestone et al. |
| 2012/0226152 A1 | 9/2012 | Porikli |
| 2012/0253200 A1 | 10/2012 | Stolka et al. |
| 2012/0265236 A1 | 10/2012 | Wesselmann et al. |
| 2012/0275668 A1 | 11/2012 | Chou et al. |
| 2013/0051651 A1 | 2/2013 | Leary et al. |
| 2013/0162796 A1 | 6/2013 | Bharara et al. |
| 2013/0335545 A1 | 12/2013 | Darling |
| 2014/0048687 A1 | 2/2014 | Drzymala et al. |
| 2014/0088402 A1 | 3/2014 | Xu |
| 2014/0354830 A1 | 12/2014 | Schafer et al. |
| 2015/0077517 A1 | 3/2015 | Powers |
| 2015/0089994 A1 | 4/2015 | Richards |
| 2015/0142462 A1 | 5/2015 | Vaidya et al. |
| 2015/0150457 A1* | 6/2015 | Wu ..................... A61B 5/6898 600/425 |
| 2015/0214993 A1 | 7/2015 | Huang |
| 2015/0250416 A1* | 9/2015 | LaPlante ............... A61B 5/445 600/476 |
| 2015/0265236 A1 | 9/2015 | Garner et al. |
| 2015/0270734 A1 | 9/2015 | Davison et al. |
| 2016/0100790 A1 | 4/2016 | Cantu et al. |
| 2016/0157725 A1 | 6/2016 | Munoz |
| 2016/0178512 A1 | 6/2016 | Hall et al. |
| 2016/0206205 A1* | 7/2016 | Wu ..................... A61B 5/445 |
| 2016/0259992 A1 | 9/2016 | Knodt et al. |
| 2016/0261133 A1 | 9/2016 | Wang |
| 2016/0262659 A1 | 9/2016 | Fright et al. |
| 2016/0275681 A1 | 9/2016 | D'alessandro |
| 2016/0284084 A1* | 9/2016 | Gurcan ................. G06T 7/0016 |
| 2016/0338594 A1 | 11/2016 | Spahn et al. |
| 2017/0076446 A1* | 3/2017 | Pedersen ................ A61B 5/445 |
| 2017/0079577 A1 | 3/2017 | Fright et al. |
| 2017/0084024 A1* | 3/2017 | Gurevich ............. A61B 5/0071 |
| 2017/0085764 A1 | 3/2017 | Kim et al. |
| 2017/0086940 A1 | 3/2017 | Nakamura |
| 2017/0127196 A1 | 5/2017 | Blum et al. |
| 2017/0236273 A1 | 8/2017 | Kim et al. |
| 2017/0258340 A1 | 9/2017 | Przybyszewski et al. |
| 2017/0262985 A1 | 9/2017 | Finn |
| 2017/0303790 A1 | 10/2017 | Bala et al. |
| 2017/0303844 A1 | 10/2017 | Baker et al. |
| 2018/0132726 A1 | 5/2018 | Dickie et al. |
| 2018/0214071 A1 | 8/2018 | Fright et al. |
| 2018/0252585 A1 | 9/2018 | Burg |
| 2018/0254100 A1 | 9/2018 | Fairbairn et al. |
| 2018/0271378 A1 | 9/2018 | Fright et al. |
| 2018/0279943 A1 | 10/2018 | Budman et al. |
| 2018/0296092 A1 | 10/2018 | Hassan et al. |
| 2018/0303413 A1 | 10/2018 | Hassan et al. |
| 2018/0322647 A1 | 11/2018 | Harrington et al. |
| 2018/0336720 A1 | 11/2018 | Larkins et al. |
| 2019/0133513 A1 | 5/2019 | Patwardhan |
| 2019/0240166 A1 | 8/2019 | Jung et al. |
| 2019/0273890 A1 | 9/2019 | Christiansen, II et al. |
| 2019/0290187 A1 | 9/2019 | Ariri et al. |
| 2019/0298183 A1 | 10/2019 | Burg et al. |
| 2019/0298252 A1 | 10/2019 | Patwardhan |
| 2019/0307337 A1 | 10/2019 | Little et al. |
| 2019/0307400 A1 | 10/2019 | Zhao et al. |
| 2019/0310203 A1 | 10/2019 | Burg et al. |
| 2019/0336003 A1 | 11/2019 | Patwardhan |
| 2019/0350535 A1 | 11/2019 | Zhao et al. |
| 2019/0369418 A1 | 12/2019 | Joy et al. |
| 2020/0014910 A1 | 1/2020 | Larkins |
| 2020/0121245 A1 | 4/2020 | Barclay et al. |
| 2020/0126226 A1 | 4/2020 | Adiri et al. |
| 2020/0126227 A1 | 4/2020 | Adiri et al. |
| 2020/0196962 A1 | 6/2020 | Zhao et al. |
| 2020/0209214 A1 | 7/2020 | Zohar et al. |
| 2020/0211193 A1 | 7/2020 | Adiri et al. |
| 2020/0211228 A1 | 7/2020 | Adiri et al. |
| 2020/0211682 A1 | 7/2020 | Zohar et al. |
| 2020/0211693 A1 | 7/2020 | Adiri et al. |
| 2020/0211697 A1 | 7/2020 | Adiri et al. |
| 2020/0225166 A1 | 7/2020 | Burg et al. |
| 2020/0234444 A1 | 7/2020 | Budman et al. |
| 2020/0286600 A1 | 9/2020 | De Brouwer et al. |
| 2020/0297213 A1 | 9/2020 | Patwardhan |
| 2020/0359971 A1 | 11/2020 | Zhao et al. |
| 2020/0364862 A1 | 11/2020 | Dacosta et al. |
| 2020/0383631 A1 | 12/2020 | Canfield et al. |
| 2021/0000387 A1 | 1/2021 | Zizi |
| 2021/0004995 A1 | 1/2021 | Burg et al. |
| 2021/0068664 A1 | 3/2021 | Fright et al. |
| 2021/0219907 A1 | 7/2021 | Fright et al. |
| 2021/0386295 A1 | 12/2021 | Dickie et al. |
| 2022/0215538 A1 | 7/2022 | Robinson et al. |
| 2022/0270746 A1 | 8/2022 | Fairbairn et al. |

FOREIGN PATENT DOCUMENTS

| | | |
|---|---|---|
| DE | 2642841 A1 | 3/1978 |
| DE | 3420588 A1 | 12/1984 |
| DE | 4120074 A1 | 1/1992 |
| EP | 355221 A1 | 2/1990 |
| EP | 552526 A1 | 7/1993 |
| EP | 650694 A1 | 5/1995 |
| EP | 1210906 A1 | 6/2002 |
| EP | 1248237 A2 | 10/2002 |
| EP | 1351036 A1 | 10/2003 |
| EP | 1303267 | 4/2004 |
| EP | 1584405 A2 | 10/2005 |
| EP | 1611543 A2 | 1/2006 |
| EP | 1467706 | 3/2007 |
| EP | 1946567 A2 | 7/2008 |
| EP | 119660 A1 | 5/2009 |

(56) References Cited

FOREIGN PATENT DOCUMENTS

| | | |
|---|---|---|
| EP | 2272047 | 3/2012 |
| EP | 2883037 | 6/2015 |
| EP | 3114462 | 1/2017 |
| EP | 3143378 | 3/2017 |
| EP | 3160327 | 5/2017 |
| EP | 2750673 | 8/2017 |
| EP | 3251332 | 12/2017 |
| EP | 3270770 | 1/2018 |
| EP | 3286695 | 2/2018 |
| EP | 3364859 | 8/2018 |
| EP | 3365057 | 8/2018 |
| EP | 3371779 | 9/2018 |
| EP | 3371780 | 9/2018 |
| EP | 3381015 | 11/2019 |
| EP | 3586195 | 1/2020 |
| EP | 3589187 | 1/2020 |
| EP | 3602501 | 2/2020 |
| EP | 3555856 | 4/2020 |
| EP | 3655924 | 5/2020 |
| EP | 3371781 | 9/2020 |
| EP | 3707670 | 9/2020 |
| ES | 2384086 | 6/2012 |
| FR | 2570206 A1 | 3/1986 |
| GB | 2458927 | 11/2012 |
| GB | 2544263 | 5/2017 |
| GB | 2544460 | 5/2017 |
| GB | 2544725 | 5/2017 |
| GB | 2545394 | 6/2017 |
| GB | 2557633 | 6/2018 |
| GB | 2557928 | 7/2018 |
| GB | 2559977 | 8/2018 |
| GB | 2559978 | 8/2018 |
| JP | 2011516849 | 5/2011 |
| JP | 5467404 | 4/2014 |
| NZ | 293713 A | 9/1997 |
| NZ | 588740 | 7/2012 |
| WO | 2000003210 A1 | 1/2000 |
| WO | 2000030337 A2 | 5/2000 |
| WO | 2002001143 A2 | 1/2002 |
| WO | 2002065069 A2 | 8/2002 |
| WO | 2002093450 A1 | 11/2002 |
| WO | 2004092874 A2 | 10/2004 |
| WO | 2004095372 A1 | 11/2004 |
| WO | 2005033620 A2 | 4/2005 |
| WO | 2006078902 A2 | 7/2006 |
| WO | 2007029038 A1 | 3/2007 |
| WO | 2007043899 A1 | 4/2007 |
| WO | 2007059780 A1 | 5/2007 |
| WO | 2008033010 A1 | 3/2008 |
| WO | 2008039539 A2 | 4/2008 |
| WO | 2008048424 A2 | 4/2008 |
| WO | 2008057056 A1 | 5/2008 |
| WO | 2008071414 A1 | 6/2008 |
| WO | 2008080385 A1 | 7/2008 |
| WO | 2009046218 A2 | 4/2009 |
| WO | WO2009122200 | 10/2009 |
| WO | 2010048960 A1 | 5/2010 |
| WO | 2012146720 A1 | 11/2012 |
| WO | WO2016069463 | 5/2016 |
| WO | 2016199134 A1 | 12/2016 |
| WO | WO-2016199134 A1 * | 12/2016 ........... A61B 5/0077 |
| WO | WO2017077276 | 5/2017 |
| WO | WO2017077277 | 5/2017 |
| WO | WO2017077278 | 5/2017 |
| WO | WO2017089826 | 6/2017 |
| WO | WO2018109453 | 6/2018 |
| WO | WO2018109479 | 6/2018 |
| WO | WO2018154271 | 8/2018 |
| WO | WO2018154272 | 8/2018 |
| WO | 2018185560 A2 | 10/2018 |
| WO | WO2019239106 | 12/2019 |
| WO | WO2019239147 | 12/2019 |
| WO | WO2020014779 | 1/2020 |
| WO | WO2020141346 | 7/2020 |
| WO | WO2020251938 | 12/2020 |

OTHER PUBLICATIONS

Stephen M. Plaza et al., Minimizing Manual Image Segmentation Turn-Around Time for Neuronal Reconstruction by Embracing Uncertainty, Plos One, vol. 7, Issue 9, Sep. 2012 (Year: 2012).*
K. Sundeep Kumar & B. Eswara Reddy, Wound Image Analysis Classifier for Efficient Tracking of Wound Healing Status, Signal & Image Processing : An International Journal (SIPIJ) vol. 5, No. 2, pp. Apr. 15-27, 2014 (Year: 2014).*
Dowsett C et al., Triangle of Wound Assessment—made easy, Wounds Asia (www.woundsasia.com), May 2015 (Year: 2015).*
Afromowitz, et al., "Multispectral Imaging of Burn Wounds: A New Clinical Instrument for Evaluating Burn Depth", IEEE Transactions on Biomedical Engineering, vol. 35, No. 10, pp. 842-850; Oct. 1988.
Ahn et al., "Advances in Wound Photography and Assessment Methods," Advances in Skin & Wound Care, Feb. 2008, pp. 85-93.
Ahroni, JH et al "Reliability of computerized wound surface area determinations" Wounds: A Compendium of Clinical Research and Practice, No. 4, (1992) 133-137.
Anderson, R., et al. "The Optics of Human Skin", The Journal of Investigative Dermatology, vol. 77, No. 1, pp. 13-19; Jul. 1981.
Armstrong, DG et al "Diabetic foot ulcers: prevention, diagnosis and classification" Am Fam Physician Mar. 15, 1998; 57 (6) :1325-32, 1337-8.
Bale, S, Harding K, Leaper D. An Introduction to Wounds. Emap Healthcare Ltd 2000.
Beaumont, E et al. "RN Technology Scorecard: Wound Care Science at the Crossroads" American Journal of Nursing Dec. 1998 98(12):16-18, 20-21.
Bergstrom, N, Bennett MA, Carlson CE. Treatment of Pressure Ulcers: Clinical Practice Guideline No. 15. Rockville, MD: U.S. Department of Health and Human Services. Public Health Service, Agency for Health Care Policy and Research 1994: 95-0652: [O].
Berriss 1997: Automatic Quantitative Analysis of Healing Skin Wounds using Colour Digital Image Processing: William Paul Berriss, Stephen John Sangwine [E].
Binder, et al., "Application of an artificial neural network in epiluminescence microscopy pattern analysis of pigmented skin lesions: a pilot study", British Journal of Dermatology 130; pp. 460-465; 1994.
Bland, JM et al. "Measurement error and correlation coefficients" BMJ Jul. 6, 1996; 313 (7048) :41-2.
Bland, JM et al. "Measurement error" BMJ Jun. 29, 1996; 312 (7047) :1654.
Bohannon Richard; Barbara A Pfaller Documentation of Wound Surface Area from Tracings of Wound Perimeters [E].
Bolton, L., "Re Measuring Wound Length, Width, and Area: Which Technique?" Letters, Advances in Skin & Wound Care, pp. 450-452, vol. 21, No. 10.
Bostock, et al, Toward a neural network based system for skin cancer diagnosis; IEEE Conference on Artificial neural Networks, ISBN: 0-85296-573-7, pp. 215-219, May 1993.
BPG2005: Assessment and Management of Foot Ulcers for People with Diabetes:Nursing Best Practice Guidelines, Toronto, Ontario [E], Mar. 2013.
Briers, J.D., "Laser speckle contrast imaging for measuring blood flow," Optica Applicata, 2007, pp. 139-152, vol. XXXVII, No. 1-2.
Briggs Corporation: Managed care making photo documentation a wound care standard. Wound care solutions product catalog 1997.
Brown, G "Reporting outcomes for Stage IV pressure ulcer healing: a proposal" Adv Skin Wound Care (2000)13:277-83.
Callieri 2003: Callieri M, Cignoni P, Pingi P, Scopigno R. Derma: Monitoring the evolution of skin lesions with a 3D system, VMV 2003. 8th International Fall Workshop, Vision, Modeling, and Visualization 2003, Nov. 19-21, 2003, Munich, Germany [E].
Campana: XML-based synchronization of mobile medical devices [E], 2002, 2 pages.
Cardinal et al., "Early healing rates and wound area measurements are reliable predictors of later complete wound closure," Wound Rep. Reg., 2008, pp. 19-22, vol. 16.

(56) References Cited

OTHER PUBLICATIONS

Cardinal et al., "Wound shape geometry measurements correlate to eventual wound healing," Wound Rep. Reg., 2009, pp. 173-178, vol. 17.
Cascinelli, N., et al. "Results obtained by using a computerized image analysis system designed as an aid to diagnosis of cutaneous melanoma", Melanoma Research, vol. 2, pp. 163-170, 1992.
Cleator et al., "Mobile wound care: Transforming care through technology," Rehab & Community Care Medicine, Winter 2008, pp. 14-15.
Collins, C et al "The Role of Ultrasound in Lower Extremity Wound Management" International Journal of Lower Extremity Wounds (2002) 1: 229-235.
Daubechies, I., "The Wavelet Transform, Time-Frequency Localization and Signal Analysis", IEEE Trans Inform Theory, vol. 36, No. 5, pp. 961-1005; Sep. 1990.
De Vet, HC et al "Current challenges in clinimetrics" J Clin Epidemiol Dec. 2003; 56 (12) :1137-41.
De Vet, H C., et al., "When to use agreement versus reliability measures", J Clin Eoidemiol 59 (10), (Oct. 2006), 1033-9.
Debray, M., Couturier P, Greuillet F, Hohn C, Banerjee S, Gavazzi G, Franco A. "A preliminary study of the feasibility of wound telecare for the elderly." Journal of Telemedicine & Telecare 2001: 7(6): 353-8. [A].
Duckworth et al., "A Clinically Affordable Non-Contact Wound Measurement Device," 2007, pp. 1-3.
Duff, et al. (2003), Loftus Hills A, Morrell C 2000 Clinical. Guidelines for the management of venous leg ulcers: Implementation Guide. Royal College of Nursing; 2000: 001 (213): 1-48. [E].
Ercal, F., "Detection of Skin Tumor Boundaries in Color Images", IEEE Transactions of Medical Imaging, vol. 12, No. 3, pp. 624-627, Sep. 1993.
Ercal, F., et al. "Neural Network Diagnosis of Malignant Melanoma From Color Images", IEEE Transactions of Biomedical Engineering, vol. 41, No. 9, pp. 837-845, Sep. 1994.
Ferrell, B "Pressure ulcers. Assessment of healing" Clin Geriatr Med (1997)13:575-87.
Fette, A.M., "A clinimetric analysis of wound measurement tools," World Wide Wounds, 2006, [retrieved on Jul. 26, 2006]. Retrieved from the Internet: <URL: http://www.worldwidewounds.com/2006/January/Fette/Clinimetric-Ana . . . >, 6 pages.
Fitzpatrick et al., "Evaluating patient-based outcome measures for use in clinical trials," Health Technology Assessment, 1998, vol. 2, No. 14, 86 pages.
Flahr et al., "Clinimetrics and Wound Science," Wound Care Canada, 2005, pp. 18-19, 48, vol. 3, No. 2.
Flanagan, M. "Improving accuracy of wound measurement in clinical practice" Ostomy Wound Manage Oct. 2003, 49(10):28-40.
Flanagan, M., "Wound measurement: can it help us to monitor progression to healing?" JWound Care May 2003, 12(5):189-94.
Gethin et al., "Wound Measurement: the contribution to practice," EWMA Journal, 2007, pp. 26-28, vol. 7, No. 1.
Gilman, T "Wound outcomes: the utility of surface measures" Int J Low Extrem Wounds Sep. 2004; 3 (3) : 125-32.
Goldman, RJ "The patientcom, 1 year later" Adv Skin Wound Care Nov.-Dec. 2002; 15 (6) :254, 256.
Goldman, RJ et al. "More than one way to measure a wound: An overview of tools and techniques" Adv Skin Wound Care (2002) 15:236-45.
Golston, et al. "Automatic Detection of Irregular Borders in Malanoma and Other Skin Tumors", Computerized Medical Imaging and Graphics, vol. 16, No. 3, pp. 199-203, 1992.
Graaf, R., et al. "Optical properties of human dermis in vitro and in vivo", Applied Optics, vol. 32, No. 4, pp. 435-447, Feb. 1, 1993.
Greene, A., "Computer image analysis in the diagnosis of melanoma", Journal of the American Academy of Dermatology; vol. 31, No. 6, pp. 958-964, 1994.
Griffin, JW et al "A comparison of photographic and transparency-based methods for measuring wound surface area" Phys Ther Feb. 1993; 73 (2) :117-22.

Haghpanah et al., "Reliability of Electronic Versus Manual Wound Measurement Techniques," Arch Phys Med Rehabil, Oct. 2006, pp. 1396-1402, vol. 87.
Hansen 1997: Wound Status Evaluation Using Color Image Processing Gary: L. Hansen, Ephraim M. Sparrow, Jaydeep Y. Kokate, Keith J. Leland, and Paul A. Iaizzo [E].
Hayes 2003:Hayes S, Dodds, S. Digital photography in wound care. Nursing Times 2003:9(42):48-9. [A].
Herbin, et al, Color Quantitation Through Image Processing in Dermatology; IEEE Transaction on Medical Imaging, vol. 9, Issue 3, pp. 262-269, Sep. 1990.
Hibbs, P "The economics of pressure ulcer prevention" Decubitus Aug. 1998; 1 (3) :32-8.
Houghton 2000: Houghton PE, Kincaid CB, Campbell KE, Woodbury MG, Keast DH. Photographic assessment of the appearance of chronic pressure and leg ulcers. Ostomy Wound management 2000: 46(4): 20-6, 28-30. [A].
HSA Global, "Mobile Wound Care", Marketing material (2009).
Huang, C., et al."Border irregularity: atypical moles versus melanoma", Eur J Dermatol, vol. 6, pp. 270-273, Jun. 1996.
Iakovou, D. et al., "Integrated sensors for robotic laser welding," Proceedings of the Third International WLT-Conference on Lasers in Manufacturing, Jun. 2005, pp. 1-6.
International Search Report and Written Opinion for International Application No. PCT/US2004/028445 filed Sep. 1, 2004.
International Search Report and Written Opinion dated Jan. 23, 2019, International Application No. PCT/IB2018/000447, 20 pages.
International Search Report and Written Opinion dated Jul. 2, 2019, International Application No. PCT/IB2018/001572, 17 pages.
International Search Report and Written Opinion dated Mar. 1, 2007, International Application No. PCT/NZ2006/000262, 12 pages.
Johnson, JD (1995) Using ulcer surface area and volume to document wound size, J Am Podiatr Med Assoc 85(2), (Feb. 1995), 91-5.
Jones, et al, An Instrument to Measure the Dimension of Skin Wounds; IEEE Transaction on Biomedical Engineering, ISSN: 0018-9294; vol. 42, Issue 5, pp. 464-470, May 1995.
Jones, TD "Improving the Precision of Leg Ulcer Area Measurement with Active Contour Models", PhD Thesis (1999) http://www.comp.glam.ac.uklpages/staff/tjones/ThesisOL/Title.Htm.
Jones, TD et al "An active contour model for measuring the area of leg ulcers" IEEE Trans Med Imaging Dec. 2000, 19(12):1202-10.
Kecelj-Leskovec et al., "Measurement of venous leg ulcers with a laser-based three-dimensional method: Comparison to computer planimetry with photography," Wound Rep Reg, 2007, pp. 767-771, vol. 15.
Kenet, R., et al. "Clinical Diagnosis of Pigmented Lesions Using Digital Epiluminescence Microscopy", Arch Dermatol, vol. 129, pp. 157-174; Feb. 1993.
Khashram et al., "Effect of TNP on the microbiology of venous leg ulcers: a pilot study," J Wound Care, Apr. 2009, pp. 164-167, vol. 18, No. 4.
Kloth, LC et al "A Randomized Controlled Clinical Trial to Evaluate the Effects of Noncontact Normothermic Wound Therapy on Chronic Full-thickness Pressure Ulcers" Advances in Skin & Wound Care Nov./Dec. 2002, 15(6):270-276.
Korber et al., "Three-dimensional documentation of wound healing: First results of a new objective method for measurement," JDDG, Oct. 2006, (Band 4), pp. 848-854.
Koren, et al, Interactive Wavelet Processing and Techniques Applied to Digital Mammography; IEEE Conference Proceedings, ISBN: 0-7803-3192-3; vol. 3, pp. 1415-1418, May 1996.
Kovesi, P., "Image Features From Phase Congruency", University of Western Australia, pp. 1-30; Technical Report 9/4, Revised Jun. 1995.
Krouskop, TA et al "A noncontact wound measurement system" J Rehabil Res Dev May-Jun. 2002, 39(3):337-45.
Kundin 1989: Kudin JI. A new way to size up a wound. American Journal of Nursing 1989: (2):206-7.
Lakovou, D. et al., "Integrated sensors for robotic laser welding," Proceedings of the Third International WLT-Conference on Lasres in Manufacturing, Jun. 2005, pp. 1-6.

(56) References Cited

OTHER PUBLICATIONS

Langemo et al., "Measuring Wound Length, Width, and Area: Which Technique?", Advances in Skin & Wound Care, Jan. 2008, pp. 42-45, vol. 21, No. I.
Langemo, DK et al "Comparison of 2 Wound Volume Measurement Methods" Advances in Skin & Wound Care Jul./Aug. 2001, vol. 14(4), 190-196.
Langemo, DK et al "Two-dimensional wound measurement: comparison of 4 techniques" Advances in Wound Care Nov.-Dec. 1998, 11(7):337-43.
Laughton, C et al. "A comparison of four methods of obtaining a negative impression of the foot" J Am Podiatr Med Assoc May 2002; 92 (5) :261-8.
Lee, et al, A Multi-stage Segmentation Method for Images of Skin Lesions; IEEE Conference Proceedings on Communication, Computers, and Signal Processing, ISBN 0-7803-2553-2, pp. 602-605, May 1995.
Levoy, et al. "The Digital Michelangelo Project: 3D Scanning Of Large Statues," ACM, 2000.
Lewis 1997: Lewis P, McCann R, Hidalgo P, Gorman M. Use of store and forward technology for vascular nursing teleconsultation service. Journal of Vascular Nursing 1997. 15(4): 116-23. [A].
Lewis, JS, Achilefu S, Garbow JR, Laforest R, Welch MJ., Small animal imaging. current technology and perspectives for oncological imaging, Radiation Sciences, Washington University School of Medicine, Saint Louis, MO, USA, Eur J Cancer. Nov. 2002;38(16):2173-88.
Li, D. 2004, Database design and implementation for wound measurement system. Biophotonics, 2004: 42-43. [E].
Liu et al., "Wound measurement by curvature maps: a feasibility study," Physiol. Meas., 2006, pp. I 107-1123, vol. 27.
Lorimer, K "Continuity through best practice: design and implementation of a nurse-led community leg-ulcer service" Can J Nurs Res Jun. 2004, 36(2):105-12.
Lowery et al., "Technical Overview of a Web-based Telemedicine System for Wound Assessment," Advances in Skin & Wound Care, Jul./Aug. 2002, pp. 165-169, vol. 15, No. 4.
Lowson, S., "The safe practitioner: Getting the record straight: the need for accurate documentation," J Wound Care, Dec. 2004, vol. 13, No. 10, [retrieved on Dec. 17, 2004). Retrieved from the Internet: <URL: http://www.journalofwoundcare.com/nav?page=jowc.article&resource=l455125>, 2 pages.
Lucas, C., "Pressure ulcer surface area measurement using instant full-scale photography and transparency tracings," Advances in Skin & Wound Care, Jan./Feb. 2002, [retrieved on Jul. 28, 2006]. Retrieved from the Internet: <URL: http://www.findarticles.com/p/articles/mi_qa3977/is_200201 /ai_n904 . . . >, 7 pages.
Lunt, M.J., "Review of duplex and colour Doppler imaging of lower-limb arteries and veins," World Wide Wounds, 2000, [retrieved on Apr. 17, 2005]. Retrieved from the Internet: <URL: http://www.worldwidewounds.com/2000/sept/Michael-Lunt/Dopple . . . >, 6 pages.
Maglogiannis et al., "A system for the acquisition of reproducible digital skin lesions images," Technol and Health Care, 2003, pp. 425-441, vol. 11.
Malian et al., "MEDPHOS: A New Photogrammetric System for Medical Measurement," 2004, Commission V, WG V/3, 6 pages.
Mallat, S., et al. "Characterization of signals from multiscale edges", IEEE Trans Patt and Mech Int'l; 14:710-732; 1992.
Marchesini, R., et al. "In vivo Spectrophotometric Evaluation of Neoplastic and Non-Neoplastic Skin Pigmented Lesions. III. CCD Camera-Based Reflectance Imaging", Photochemistry and Photobiology, vol. 62, No. 1, pp. 151-154; 1995.
Marjanovic et al., "Measurement of the volume of a leg ulcer using a laser scanner," Physiol. Meas., 1998, pp. 535-543, vol. 19.
Mastronjcola et al., "Burn Depth Assessment Using a Tri-stimulus Colorimeter," Wounds—ISSN: !044-7946, Sep. 2005, pp. 255-258, vol. 17, No. 9.
McCardle, J., "Visitrak: wound measurement as an aid to making treatment decisions," The Diabetic Foot, Winter 2005, [retrieved on Mar. 30, 2008). Retrieved from the Internet: <URL: http://findarticles.com/p/articles/mi_ mOMDQ/is_4_8/ai_n16043804/print>, 4 pages.
Menzies, S., "The Morphologic Criteria of the Pseudopod in Surface Microscopy", Arch Dermatol, vol. 131, pp. 436-440, Apr. 1995.
Molnar et al., "Use of Standardized, Quantitative Digital Photography in a Multicenter Web-based Study," 2009, ePlasty, pp. 19-26, vol. 9.
Nachbar, et al., "The ABCD rule of dermatology", Journal of the American Academy of Dermatology, vol. 3, No. 4, pp. 551-559, Apr. 1994.
National Pressure Ulcer Advisory Panel, "FAQ: Photography for pressure ulcer documentation," 1 1P56, 4 pages.
National Pressure Ulcer Advisory Panel, Position Statement, 1998, [retrieved on Jan. 6, 2005], Retrieved from the Internet: <URL: http://www.npuap.org/>, 2 pages (Pressure Ulcer Healing Chart attached, 2 pages).
Oduncu et al., "Analysis of Skin Wound Images Using Digital Color Image Processing: A Preliminary Communication," Lower Extremity Wounds, 2004, pp. 151-156, vol. 3, No. 3.
Pages, Jordi, et al., "Plane-to-plane positioning from image-based visual serving and structured light," Proceedings of 2004 IEEE/RSJ International Conference on Intelligent Robots and Systems, Sep. 28-Oct. 2, 2004, pp. 1004-1009.
Patete et al., "A non-invasive, three-dimensional, diagnostic laser imaging system for accurate wound analysis," Physiol. Meas., 1996, pp. 71-79, vol. 17.
Payne, C., "Cost benefit comparison of plaster casts and optical scans of the foot for the manufacture of foot orthoses," AJPM, 2007, pp. 29-31, vol. 41, No. 2.
Pehamberger, H., et al. "In vivo epiluminescence microscopy of pigmented skin lesions. I. Pattern analysis of pigmented skin lesions", Journal of American Academy of Dermatology, vol. 17, No. 4, pp. 571-583, Oct. 1987.
Plassman, et al. "Problems of Assessing Wound Size," Would healing Research Unit, University of Wales College of Medicine, Cardiff CF4 4XN, Wales, UK (1993) (Unpublished).
Plassmann et al., "MAVIS: a non-invasive instrument to measure area and volume of wounds," Medical Engineering & Physics, 1998, pp. 332-338, vol. 20.
Plassmann, P., "Recording Wounds—Documenting Woundcare," Medical Computing Group, 1998, pp. 1-31.
Rogers et al., "Measuring Wounds: Which Stick to Use?", Podiatry Management, Aug. 2008, pp. 85-90.
Romanelli et al., "Technological Advances in Wound Bed Measurements," Wounds, 2002, pp. 58-66, vol. 14, No. 2, [retrieved on Apr. 8, 2005]. Retrieved from the Internet: <URL: http:/lwww.medscape.com/viewarticle/430900 _print>, 8 pages.
Russell, L., "The importance of wound documentation & classification," British J Nursing, 1999, pp. 1342-1354, vol. 8, No. 20.
Salcido, R., "The Future of Wound Measurement," Advances in Skin & Wound Care, Mar./Apr. 2003, pp. 54, 56, vol. 13, No. 2.
Salcido, R., "Pressure Ulcers and Wound Care," Physical Medicine and Rehabilitation, eMedicine, 2006, [retrieved on]. Retrieved from the Internet: <URL: http://www.emedicine.com/pmr/topic 179.htm>, 25 pages.
Salmhofer, et al., "Wound teleconsultation in patients with chronic leg ulcers," 2005.
Sani-Kick et al., "Recording and Transmission of Digital Wound Images with the Help of a Mobile Device," 2002, 2 pages.
Santamaria et al., "The effectiveness of digital imaging and remote expert wound consultation on healing rates in chronic lower leg ulcers in the Kimberley region of Western Australia," Primary Intention, May 2004, pp. 62-70, vol. 12, No. 2.
Schindewolf, et al. "Comparison of classification rates for conventional and dermatoscopic images of malignant and benign melanocytic lesions using computerized colour image analysis", Eur J Dermatol, vol. 3, No. 4, pp. 299-303, May 1993.
Schindewolf, T., et al. "Classification of Melanocytic Lesions with Color and Texture Analysis Using Digital Image Processing", The International Academy of Cytology, Analytical and Quantitative Cytology and Histology, vol. 15, No. 1, pp. 1-11, Feb. 1993.
Schindewolf, T., et al. "Evaluation of different image acquisition techniques for a computer vision system in the diagnosis of malig-

(56) References Cited

OTHER PUBLICATIONS nant melanoma", Journal of the American Academy of Dermatology, vol. 31, No. 1, pp. 33-41, Jul. 1994.
Schultz et al., "Wound bed preparation: a systematic approach to wound management," Wound Repair and Regeneration, Mar./Apr. 2003, p. SI-S28, vol. 1 1, No. 2, Supplement.
Shaw et al., "An Evaluation of Three Wound Measurement Techniques in Diabetic Foot Wounds," Diabetes Care, 2007, [retrieved on Mar. 30, 2008], Retrieved from the Internet: <URL: http://care.diabetesjournals.org/cgi/content/full/30/ I 0/2641 ?ck=nck>, 5 pages.
Sheehan et al., "Percent Change in Wound Area of Diabetic Foot Ulcers Over a 4-Week Period Is a Robust Predictor of Complete Healing in a 12-Week Prospective Trial," Diabetes Care, Jun. 2003, pp. 1879-1882, vol. 26, No. 6.
Sheng, Chao, Brian W. Pogue, Hamid Dehghani, Julia A. O'Hara, P. J. Hoopes, Numerical light dosimetry in murine tissue: analysis of tumor curvature and angle of incidence effects upon fluence in the tissue, Proc. SPIE, vol. 4952, 39 (2003), DOI:10.1117/12.474081, Online Publication Date: Jul. 28, 2003.
Smith & Nephew, "Leg ulcer guidelines: a pocket guide for practice," National Guideline Clearinghouse, U.S. Dept of Health & Human Services, 2002, [retrieved on Jan. 10, 2012]. Retrieved from the Internet: <URL: http://guidelines.gov/content.aspx?id=9830 &search=Pressure+Ulcer>, 17 pages.
Smith & Nephew, "Visitrak Wound Measurement Device," Wound Management, [retrieved on Apr. 7, 2005]. Retrieved from the Internet: <URL: http://wound.smith-nephew.com/us/node.asp?NodeId=3 I 20>, 7 pages.
Smith & Nephew, "Guidelines for the Management of Leg Ulcers in Ireland" www.smith-nephew.com.
Smith et al., "Three-Dimensional Laser Imaging System for Measuring Wound Geometry," Lasers in Surgery and Medicine, 1998, pp. 87-93, vol. 23.
Sober, et al., "Computerized Digital Image Analysis: An Aid for Melanoma Diagnosis", The Journal of Dermatology, vol. 21, pp. 885-890, 1994.
Solomon et al., "The use of video image analysis for the measurement of venous ulcers," British J Dermatology, 1995, pp. 565-570, vol. I 33.
Steiner, A., "In vivo epiluminescence microscopy of pigmented skin lesions. II. Diagnosis of small pigmented skin lesions and early detection of malignant melanoma", Journal of the American Academy of Dermatology, vol. 17, No. 4, pp. 584-591; Oct. 1987.
Stoecker, et al. "Automatic Detection of Asymmetry in Skin Tumors", Computerized Medical Imaging and Graphics, vol. 16, No. 3, pp. 191-197, 1992.
Takiwaki, et al., "A rudimentary system for automatic discrimination among basic skin lesions on the basis of color analysis of video images", Journal of the American Academy of Dermatology, vol. 32, No. 4, pp. 600-604, Apr. 1995.
Tellez, R., "Managed Care Making Photo Documentation a Wound Care Standard," Wound Care, 1997, [retrieved on Aug. 29, 2005], Retrieved from the Internet: <URL: http://woundcare.org/newsvol2n4/arl.htm>, 2 pages.
Thali, M.J., et al. "Optical 3D surface digitizing in forensic medicine: 3D documentation of skin and bone injuries." Forensic Science International. 2003.
Thawer et al., "A Comparison of Computer-Assisted and Manual Wound Size Measurement," Ostomy Wound Management, Oct. 2002, pp. 46-53, vol. 48, No. IO.
Treuillet et al., "Three-Dimensional Assessment of Skin Wounds Using a Standard Digital Camera," IEEE Transactions on Medical Imaging, May 2009, pp. 752-762, vol. 28, No. 5.
Umbaugh et al., "Automatic Color Segmentation Algorithms with Application to Skin Tumor Feature Identification", IEEE Engineering in Medicine and Biology, pp. 75-82, Sep. 1993.
Umbaugh, et al., "An Automatic Color Segmentation Algorithm with Application to Identification of Skin Tumor Borders", Computerized Medical Imaging and Graphics, vol. 16, No. 3, pp. 227-235, May-Jun. 1992.
Umbaugh, et al., "Automatic Color Segmentation of Images with Application to Detection of Variegated Coloring in Skin Tumors", IEEE Engineering in Medicine and Biology Magazine, Dec. 1989, pp. 43-52.
Van Zuijlen et al., "Reliability and Accuracy of Practical Techniques for Surface Area Measurements of Wounds and Scars," Lower Extremity Wounds, 2004, pp. 7-11, vol. 3, No. I.
Vermolen et al., "A simplified model for growth factor induced healing of circular wounds," 2005, pp. 1-15.
Voigt, H., et al. "Topodermatographic Image Analysis for Melanoma Screening and the Quantitative Assessment of Tumor Dimension Parameters of the Skin", Cancer, vol. 75, No. 4, Feb. 15, 1995.
Walker, N, Rogers A, Birchall N, Norton R, MacMahon S. Leg ulcers in New Zealand: age at onset, recurrence and provision of care in an urban population. NZ Med J; 2002; 115(1156):286-9.
Walker, N, Vandal A, Holden K, Rogers A, Birchall N, Norton R, Triggs C, MacMahon S. Does capture-recapture analysis provide more reliable estimates of the incidence and prevalence of leg ulcers in the community? Aust NZJ Public Health 2002; 26(5):451-5.
Walker, N., Rodgers A, Birchall N, Norton R, MacMahon S. The occurrence of leg ulcers in Auckland: results of a population-based study. NZ Med J; 2002: 115 (1151): 159-162.
Wallenstein et al., "Statistical analysis of wound-healing rates for pressure ulcers," Amer J Surgery, Jul. 2004 (Supplement), pp. 73S-78S, vol. 188.
Wang et al., "A comparison of digital planimetry and transparency tracing based methods for measuring diabetic cutaneous ulcer surface area," Zhongguo Xiu Fu Chong Jian Wai Ke Za Zhi, May 2008, pp. 563-566, vol. 22, No. 5, [retrieved on Sep. 15, 2009]. Retrieved from the Internet: <URL: http://www.ncbi.nlm.nih.gov/pu bmed/ I 8630436?ordinalpos= I &itool=E . . . >, I page.
Wendelken et al., "Key Insights On Mapping Wounds With Ultrasound," Podiatry Today, Jul. 2008, [retrieved on Jul. 14, 2008]. Retrieved from the Internet: <URL: http://www.podiatrytoday.com/article/5831>, 5 pages.
Wilbright, W.A., The Use of Telemedicine in the Management of Diabetes-Related Foot Ulceration: A Pilot Study, Advances in Skin & Wound Care, Jun. 2004, [retrieved on Jul. 28, 2006]. Retrieved from the Internet: <URL: http://www.findarticles.com/p/articles/mi_qa3977/is_200406/ai_n942 . . . >, 6 pages.
Wild et al., "Wound healing analysis and measurement by means of colour segmentation," ETRS Poster Presentation V28, Sep. 15, 2005, V28-I 7, 1 page.
Williams, C., "The Verge Videometer wound measurement package," British J Nursing, Feb./Mar. 2000, pp. 237-239, vol. 9, No. 4.
Woodbury et al., Pressure ulcer assessment instruments: a critical appraisal, Ostomy Wound Management, May 1999, pp. 48-50, 53-55, vol. 45, No. 5, [retrieved on Dec. 8, 2005]. Retrieved from the Internet: <URL: http://gateway.ut.ovid.com.ezproxy.otago.ac.nzigw2/ovidweb.cgi>, 2 pages.
Woodbury, M.G., "Development, Validity, Reliability, and Responsiveness of a New Leg Ulcer Measurement Tool," Advances in Skin & Wound Care, May 2004, [retrieved on Jul. 28, 2006]. Retrieved from the Internet.
Zhao, et al, The Classification of the Depth of Burn Injury Using Hybrid Neural Network; IEEE Conference on Engineering in Medicine and Biology Society, ISBN 0-7803-2475-7; vol. 1, pp. 815-816, Sep. 1995.
Zimmet, "Venous Leg Ulcers: Evaluation and Management," American College of Phlebology. 1998.
Non-Final Office Action dated Oct. 24, 2022, U.S. Appl. No. 17/398,883, 18 pages.
Extended European Search Report for European Application No. EP22204772.2 filed Apr. 3, 2018, dated Apr. 13, 2023, 6 pages.
Final Office Action dated Jul. 13, 2023, U.S. Appl. No. 17/398,883, 22 pages.
Non-Final Office Action dated Mar. 29, 2023, U.S. Appl. No. 17/100,615, 10 pages.

\* cited by examiner

ANATOMICAL SURFACE ASSESSMENT METHODS, DEVICES AND SYSTEMS

CROSS-REFERENCE TO RELATED APPLICATION

This application is a 35 U.S.C. § 371 application of International Application No. PCT/IB2018/000447, filed Apr. 3, 2018, which claims priority to U.S. Provisional Patent Application No. 62/481,612, titled "ANATOMICAL SURFACE ASSESSMENT METHODS, DEVICES AND SYSTEMS," filed Apr. 4, 2017, both of which are incorporated herein by reference in their entirety.

TECHNICAL FIELD

The present technology is generally related to devices, systems and methods for assessing anatomical surface features.

BACKGROUND

Various techniques have been used to monitor wounds, ulcers, sores, lesions, tumours etc. (herein referred to collectively as "wounds") both within hospitals and for outpatients. Typically these wounds are flat or concave and up to 150 millimetres (around 6 inches) across, though larger wounds are also possible. Manual techniques are typically labour-intensive and require examination and contact by skilled personnel. Such measurements may be inaccurate and there may be significant variation between measurements made by different personnel. Further, these approaches may not preserve any visual record for review by an expert or for subsequent comparison.

A number of techniques for the automated monitoring of wounds have been proposed. A common approach is to place a reference object next to the wound, capture an image, and determine the size of the wound utilising the scale of the reference object. It is often undesirable to place a reference object near to a wound and this requires an additional cumbersome step for a user and risks contamination of the wound. Further, when the target is not in the plane of the wound, or if it is oblique, or if the wound is not planar, there will be errors in any area calculation. Further, a reference object may be misplaced.

It is an object of the present technology to provide improved devices, systems, and methods for assessing and/or treating wounds and/or other anatomical features.

SUMMARY

According to one embodiment a method of assessing a feature on a patient's skin surface includes: receiving a three-dimensional data set representative of the patient's skin surface; determining a boundary of the feature in the three-dimensional data set; and determining with a processor a three-dimensional surface area of the feature within the boundary.

A plurality of sub-regions may be identified within the boundary and one or more tissue types may be identified in each sub-region.

A processor may automatically identify the plurality of sub-regions. The processor may automatically identify the plurality of sub-regions by analysis of one or more of: three-dimensional image data; thermal image data; fluorescence image data; and texture image data.

Alternatively, a user may manually identify the plurality of sub-regions via a user interface.

In a further alternative, a user may manually identify one or more of the plurality of sub-regions via a user interface and a processor may automatically identify one or more others of the plurality of sub-regions.

The method may include determining for each sub-region a proportion of a surface area of that sub-region occupied by each tissue type identified in that sub-region.

The method may include determining for each sub-region a proportion of a surface area of that sub-region occupied by each tissue type identified in that sub-region; determining a surface area of each sub-region; and aggregating the determined proportions of tissue types to determine one or more of: an aggregated surface area occupied by each tissue type; and an aggregated proportion of the surface area of the feature occupied by each tissue type.

The method may include determining for each sub-region a proportion of a surface area of that sub-region occupied by each tissue type identified in that sub-region; determining a surface area of each sub-region; aggregating the determined proportions of tissue types and aggregating the tissue types into tissue classes, to determine one or more of: an aggregated surface area occupied by each tissue class; and an aggregated proportion of the surface area of the feature occupied by each tissue class.

The tissue classes may include a viable tissue class and a non-viable tissue class.

The feature may be a wound and the surface area may be a wound bed area.

Three-dimensional image data of the patient's skin surface may be captured and processed to form the three-dimensional data set.

According to another embodiment a method of assessing a feature on a patient's skin surface uses a handheld capture device that includes a three-dimensional imaging system. A first data set may be captured using the handheld capture device at a first device pose, and a second data set may be captured using the handheld capture device at a second device pose. Each of the first and second data sets may include three-dimensional image data of the patient's skin surface captured by the three-dimensional imaging system. At least the first and second data sets may be processed to form a three-dimensional model of the patient's skin surface including the feature.

The handheld capture device may include a thermal camera, and the first data set and the second data set may each include thermal image data, which may be registered with the three-dimensional model.

The handheld capture device may include a texture camera, and the first data set and the second data set may each include texture image data, which may be registered with the three-dimensional model.

The first data set and the second data set may each include fluorescence image data, which may be registered with the three-dimensional model.

In a further embodiment a method of displaying data representative of a feature on a patient's skin surface, includes: displaying a first representation of the feature based on first data captured at a first time; and displaying a second representation of the feature based on second data captured at a second time.

An animation may be displayed including at least the first and second representations.

A third representation of the feature may be created and displayed, based at least in part on an interpolation or extrapolation from at least the first and second data.

An animation may be displayed including at least the first, second and third representations.

In another embodiment a method of displaying data representative of a feature on a patient's skin surface, includes: displaying a first representation relating to the feature based on first data captured at a first time; displaying a second representation relating to the feature based on second data captured at a second time; and creating and displaying a third representation relating to the feature based at least in part on an interpolation or extrapolation from at least the first and second data.

An animation may be displayed including at least the first, second and third representations.

Each representation may be an image. The image may include a representation of a three-dimensional model including the feature.

The image may further include one or more of: a representation of thermal image data overlaid on the representation of the three-dimensional model; a representation of fluorescence image data overlaid on the representation of the three-dimensional model; a representation of texture image data overlaid on the representation of the three-dimensional model; and one or more wound dimensions.

In another embodiment, a method of displaying data representative of a feature on a patient's skin surface, may include: displaying a three-dimensional model of the skin surface including the feature; and on the displayed surface, displaying one or more indicators of a further parameter associated with the feature.

The one or more indicators may comprise one or more of: a representation of thermal image data overlaid on the representation of the three-dimensional model; a representation of fluorescence image data overlaid on the representation of the three-dimensional model; a representation of texture image data overlaid on the representation of the three-dimensional model; and one or more wound dimensions.

In a further embodiment a handheld skin assessment device may include: a three-dimensional image capture unit; a thermal image capture unit; the device having a desired capture range at which three-dimensional image data and thermal image data of a patient's skin surface will be captured by the three-dimensional image capture unit and the thermal image capture unit; and a guide arrangement configured to guide the user to position the device at the desired capture range from the patient's skin surface.

In another embodiment a handheld skin assessment device may include: a UV light source; a three-dimensional image capture unit; the device having a desired capture range at which three-dimensional image data and fluorescence image data of a patient's skin surface will be captured; and a guide arrangement configured to guide the user to position the device at the desired capture range from the patient's skin surface.

Fluorescence image data may be captured by the three-dimensional image capture unit.

Alternatively, the device may include a fluorescence camera, wherein the fluorescence image data is captured by the fluorescence camera.

The device may include one or more optical filters arranged to filter light during capture of the fluorescence image data.

In a further embodiment a handheld skin assessment device may include: a source of UV light arranged, in use, to project UV light onto a patient's skin surface; an image capture device configured to capture a plurality of image frames of the patient's skin surface, at an image frame capture rate; and electronics configured to modulate the UV light at a function of the image frame capture rate.

In a further embodiment a method of assessing a patient's skin includes: projecting UV light onto a patient's skin surface during a first time period; capturing a plurality of images of the patient's skin surface over at least a second time period immediately following the first time period; analysing fluorescence in each of the plurality of images to determine a fluorescence lifetime or fluorescence decay profile.

In another embodiment a handheld skin assessment device includes: a UV light source arranged, in use, to project UV light onto a patient's skin surface; a three-dimensional image capture device arranged, in use, to capture three-dimensional image data of the patient's skin surface; and a controller configured to control at least the UV light source and the three-dimensional image capture device to capture: a three-dimensional image data set with the UV light source off; and a fluorescence image data set with the UV light source on.

A processor may be configured to determine one or more range values from the three-dimensional image data, and to correct intensity values in the fluorescence image data set based on the one or more range values.

Fluorescence image data may be captured by the three-dimensional image capture unit.

Alternatively the device may include a fluorescence camera, wherein the fluorescence image data is captured by the fluorescence camera.

The device may include one or more optical filters arranged to filter light during capture of the fluorescence image data.

It is acknowledged that the terms "comprise", "comprises" and "comprising" may, under varying jurisdictions, be attributed with either an exclusive or an inclusive meaning. For the purpose of this specification, and unless otherwise noted, these terms are intended to have an inclusive meaning—i.e., they will be taken to mean an inclusion of the listed components which the use directly references, and possibly also of other non-specified components or elements.

BRIEF DESCRIPTION OF THE DRAWINGS

The accompanying drawings which are incorporated in and constitute part of the specification, illustrate embodiments of the present technology and, together with the general description of the present technology given above, and the detailed description of embodiments given below, serve to explain the principles of the present technology, in which.

DETAILED DESCRIPTION

Overview

Described herein is a software facility for automatically assessing an anatomical surface feature ("the facility"), such as a wound, and for managing information related to assessed anatomical surface features across a range of patients and institutions. While the following discussion liberally employs the term "wound" to refer to the anatomical surface feature(s) being assessed, the present devices, systems, and methods may be straightforwardly applied to anatomical surface features of other types, such as ulcers, sores, lesions, tumors, bruises, burns, moles, psoriasis, keloids, skin cancers, erythema, cellulitis, and the like. Similarly, a wide variety of users may use the facility, including doctors, nurses, technologists, or any other caregiver of the patient, or the patient.

As discussed in greater detail below, the facility may be implemented using readily available portable computing devices, thereby taking advantage of existing device capabilities without the need for separate hardware attachments (although in some embodiments auxiliary hardware devices may be used). As used herein, the terms "computer" and "computing device" generally refer to devices that have a processor and non-transitory memory, as well as any data processor or any device capable of communicating with a network. Data processors include programmable general-purpose or special-purpose microprocessors, programmable controllers, application-specific integrated circuits (ASICs), programming logic devices (PLDs), system on chip (SOC) or system on module (SOM) ("SOC/SOM"), an ARM class CPU with embedded Linux or Android operating system or the like, or a combination of such devices. Computer-executable instructions may be stored in memory, such as random access memory (RAM), read-only memory (ROM), flash memory, or the like, or a combination of such components. Computer-executable instructions may also be stored in one or more storage devices, such as magnetic or optical-based disks, flash memory devices, or any other type of non-volatile storage medium or non-transitory medium for data. Computer-executable instructions may include one or more program modules, which include routines, programs, objects, components, data structures, and so on that perform particular tasks or implement particular abstract data types.

Anatomical Surface Feature Assessment

Figure 1:
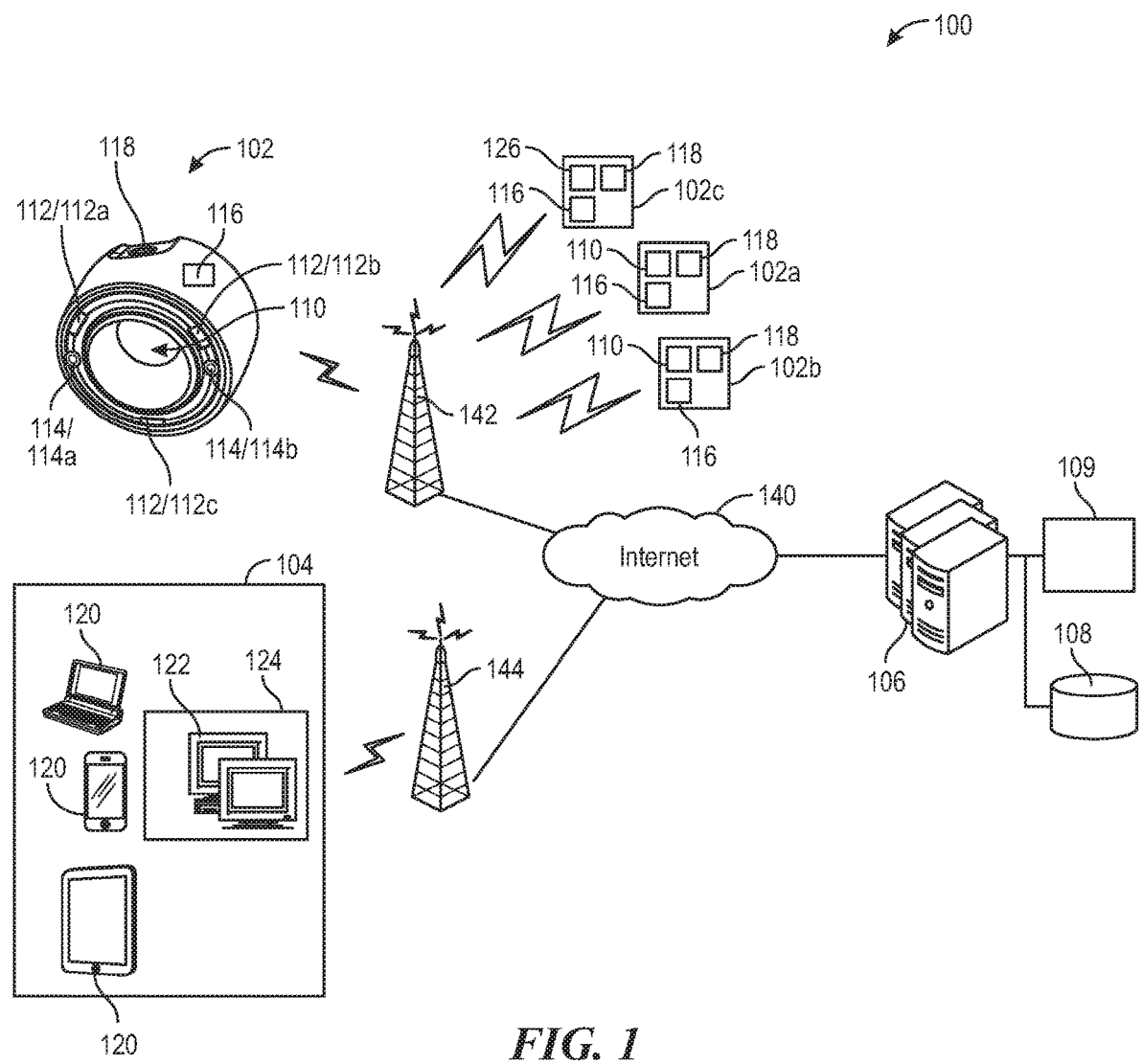
FIG. 1 is a diagram showing some of the components typically incorporated in at least some of the computer systems and other devices on which the facility executes.

FIG. 1 is a block diagram showing a sample environment having multiple components in which the facility executes. The environment 100 may include one or more capture devices 102, 102a, 102b, 102c, one or more personal computing devices 104, one or more server computers 106, and one or more persistent storage devices 108. The capture device 102, 102a, 102b, 102c and the personal computing device 104 communicate (wirelessly or through a wired connection) with the server computer 106 through a network 140 such as, for example, a Local Area Network (LAN), a Wide Area Network (WAN), and/or the Internet. In the embodiment shown in FIG. 1, the capture device 102, 102a, 102b, 102c may or may not communicate directly with the personal computing device 104. For example, the capture device 102, 102a, 102b, 102c may communicate wirelessly with a first base station or access point 142 using a wireless mobile telephone standard, such as the Global System for Mobile Communication (GSM), or another wireless standard, such as IEEE 802.11, and the first base station or access point 142 communicates with the server computer 106 via the network 140. Likewise, the computing device 104 may communicate wirelessly with a second base station or access point 144 using a wireless mobile telephone standard, such as the Global System for Mobile Communication (GSM), or another wireless standard, such as IEEE 802.11, and the second base station or access point 144 communicates with the server computer 106 via the network 140. In some embodiments, confidential patient data generated by the capture device 102, 102a, 102b, 102c is only temporarily stored locally, or not at all, and instead is permanently stored at the storage device 108 associated with the server computer 106. The facility can be practiced on any of the computing devices disclosed herein (e.g., one or more personal computing devices 104, one or more server computers 106, etc.), and may include an interface module that generates graphical user interfaces (GUIs) to allow users to access the facility (as described in greater detail below with reference to FIGS. 2-29).

The personal computing device 104 can include one or more portable computing devices 120 (e.g., a smart phone, a laptop, a tablet, etc.) and/or one or more desktop computing devices 122. During data capture with the capture device 102, 102a, 102b, 102c at the point-of-care, the personal computing device 104 may also be present (i.e., in the same treatment room), or the personal computing device 104 may be remote (i.e., outside of the treatment room but in the same treatment facility, outside of the treatment room and remote from the treatment facility, etc.). The desktop computing devices 122, if utilized, are typically associated with a particular property, e.g., a medical treatment center 124 (e.g., a hospital, a doctor's office, a clinic, etc.). The portable computing devices 120 and desktop computing devices 124 communicate with each other and the server computer 106 through networks including, for example, the Internet. In some instances the portable computing devices 120 and desktop computing devices 122 may communicate with each other through other wireless protocols, such as near field or Bluetooth.

The capture device 102, 102a, 102b, 102c is a handheld, portable imaging device that includes one or more sensing devices for generating data characterizing the wound ("wound data") at the point-of-care. In the embodiment shown in FIG. 1, the capture device 102 may include an image sensor 110 (e.g., a digital camera), a depth sensor 112 (also known as a "range imager"), and a computing device 116 (shown schematically) in communication with the image sensor 110 and the depth sensor 112.

Alternatively, in some embodiments the capture device may be a smartphone 102a, tablet 102b or other capture device including an image sensor 110 and a computing device 116. The capture device may for example be an iPhone, iPad, Android phone, other Smartphone, tablet etc.). The capture device may include one, two or some other number of cameras, and/or structured light arrangements, 3D cameras etc. In such embodiments a separate personal computing device 104 may not be required. As discussed below, an auxiliary device may be mounted to or connected to a capture device 102, 102a, 102b, 102c.

Further a variety of different capture devices 102, 102a, 102b, 102c may be used in the environment 100. Different types of capture device 102, 102a, 102b may be used to capture data in relation to the same wound, at the same or different times, by the same or different users. The data from a variety of different capture devices 102, 102a, 102b may be processed in the facility.

The capture device 102, 102a, 102b, 102c is also in wireless communication with the server computer 106 (e.g., via the network 140). The image sensor 110 is configured to generate image data of the wound (e.g., pixels containing RGB color data). In some embodiments, a hyperspectral image sensor may be used, i.e. a sensor that has sensitivity outside the conventional RGB visible spectrum range. In some embodiments a spectrometer or array of spectrometers may be used to provide greater color resolution than a conventional RGB sensor. A spectrometer or array of spectrometers may be particularly useful in analysis of fluorescence. Where provided, the depth sensor 112 is configured to generate depth data characterizing the depth or topography of the wound. For example, in some embodiments the depth sensor 112 is a structured light device configured to emit structured light (e.g., one or more lasers, DLP projectors, film projectors, etc. where the emitted light may be infra-red, visible, ultraviolet, etc.) in a predetermined arrangement toward the wound. In such embodiments, for example, the depth sensor 112 may comprise three laser elements (labeled 112a-112c) spaced apart around a circumference of the capture device 102. The laser elements 112a-112c have a fixed positional relationship with respect to one another, and also with respect to the image sensor 110. Together the laser elements 112a-112c can be configured to create a structured light pattern (e.g., a laser point(s), a laser fan(s), etc.) In some embodiments the laser elements do not need to be symmetrically arranged. In other embodiments, the depth sensor 112 can include other suitable devices for range imaging, such as an ultrasonic sensor, a stereo camera, a plenoptic camera, a time-of-flight camera, an ISM band miniature radar, etc.

The capture device 102, 102a, 102b, 102c also includes a rechargeable power source and an actuator 118 (e.g., a button, a switch, touch screen etc.) for initiating data capture. When a user presses the actuator 118, the computing device 116 activates the image sensor 110 (and the depth sensor 112 if included) to generate data. The computing device 116 then communicates the captured data to the remote server computer 106 for further processing by the facility. In some embodiments, the computing device 116 may partially or completely process the captured data before communicating the captured data to the remote server computer 106. In some embodiments, the capture device 102, 102a, 102b, 102c may partially or completely process the captured data before communicating with the computing device 116. In some embodiments, the computing device 116 wirelessly communicates with the server computer 106 (e.g., over a network). Such a cordless arrangement can be advantageous as it allows the user greater freedom of movement with the capture device 102, 102a, 102b, 102c, which can be especially beneficial when trying to access certain anatomical locations. Also, the absence of a cord reduces the surface area available at the point-of-care on which bacteria and/or other unwanted microorganisms may bind and travel. In some embodiments, the capture device 102, 102a, 102b, 102c may be permanently cordless (i.e., no input port), and in other embodiments, the capture device 102, 102a, 102b, 102c may be configured to detachably receive an electronic connector, such as a power cord or a USB cord, or a permanently attached retracting cord may be provided. The computing device 116 may automatically transfer the captured data to the remote server computer 106 (e.g., over the network 140) at the moment the data is captured. In certain embodiments, however, the computing device 116 may not be in communication with the network 140; in such scenarios, the captured data may be temporarily stored in the volatile and/or non-volatile memory of the capture device 102, 102a, 102b, 102c for later transfer to the server computer 106.

The capture device 102, 102a, 102b, 102c may include additional features for enhancing data collection from the wound, such as one or more light sources 114 (e.g., a light emitting diode (LED), an incandescent light source, an ultraviolet light source, a flash etc.) for illuminating the wound before or during data capture, an indicator (not shown) configured to provide a visual and/or audio signal (e.g., images, text, lights, etc.) to the user, a thermal camera, a video camera, and/or one or more input/output devices (e.g., a microphone, a speaker, a port for communicating electrically with external components, such as a power source, the personal computing device 104, etc.). In some embodiments, the capture device 102, 102a, 102b, 102c is configured for wireless charging, e.g., via a dock or cradle (not shown). In such embodiments, the charging cradle may also serve as an access point for the network 140. As discussed in greater detail below with reference to FIGS. 6A-6B, the capture device 102, 102a, 102b, 102c and/or image sensor 110 may also be configured to capture images of barcodes and/or QR codes displayed on the computing device 104, such as a barcode and/or a QR code that enable the capture device 102, 102a, 102b, 102c to be configured to connect to the network 140.

In some embodiments, the capture device 102, 102a, 102b, 102c may have other configurations than that shown in FIG. 1. For example, although the image sensor 110, depth sensor 112, and computing device 116 are shown as part of a single component and/or within the same housing, in other embodiments, any or all of the of the image sensor 110, the depth sensor 112, and the computing device 116 can be separate components. Likewise, in some embodiments, the capture device 102, 102c does not include separate image and depth sensors, and instead includes a stereo camera that is configured to generate both image data and depth data. In other embodiments the capture device may include a display-less imaging device connected (by wired or wireless link) to a display device. Additional details regarding suitable capture devices 102 and methods of use can be found in U.S. Pat. No. 8,755,053, filed May 11, 2009; U.S. Pat. No. 9,179,844, filed Nov. 27, 2012; U.S. patent application Ser. No. 15/144,722; and U.S. Provisional Patent Application No. 62/423,709 filed 17 Nov. 2016, all of which are incorporated herein by reference in their entireties.

As discussed above, the facility may include an interface module that generates graphical user interfaces (GUIs) to allow users to access the facility. The interface module also provides application programming interfaces (APIs) to enable communication and interfacing with the facility. APIs may be used by other applications, web portals, or distributed system components to use the system. For example, an application operating on a personal computing device may use an API to interface with system servers and receive capture data from the system. The API may utilize, for example, Representational State Transfer (REST) architecture and Simple Object Access Protocol (SOAP) protocols.

In some embodiments the capture device 102, 102a, 102b, 102c may include one or more further data gathering components, such as a positioning module (e.g. GPS), Inertial Measurement Unit, temperature sensor etc. Alternatively, such functions may in some embodiments be provided by a separate auxiliary module configured for attachment to the capture device 102, 102a, 102b, 102c.

Any of the capture devices 102, 102a, 102b, 102c and/or the personal computing devices 104 may provide access to video and/or audio communications, including video conferencing. Any of the capture devices 102, 102a, 102b, 102c and/or the personal computing devices 104 may provide access to remote medical expert systems. A remote medical expert may review or assess data captured by the capture device 102, 102a, 102b, 102c in real time, or at a later time.

The facility may provide for automated billing based on usage and/or data gathered by the capture devices 102, 102a, 102b, 102c. The facility may also maintain inventory information for capture devices 102, 102a, 102b, 102c.

The following methods may be implemented using appropriate facility software running on the capture device 102, 102a, 102b, 102c, personal computing device 104, and/or server computer 106 and/or further computing devices within the environment. In some embodiments, methods may be implemented through an application running on a capture device 102, 102a, 102b, 102c. Methods may be implemented across two or more devices and/or computers. For example, a method may include data capture steps implemented on a capture device 102, 102a, 102b, 102c, data analysis steps implemented on the capture device 102, 102a, 102b, 102c and/or personal computing device 104 and/or server computer 106, and data storage steps implemented on server computer 106 and persistent storage devices 108. In some embodiments, the personal computing device 104 may be omitted.

Figure 2:
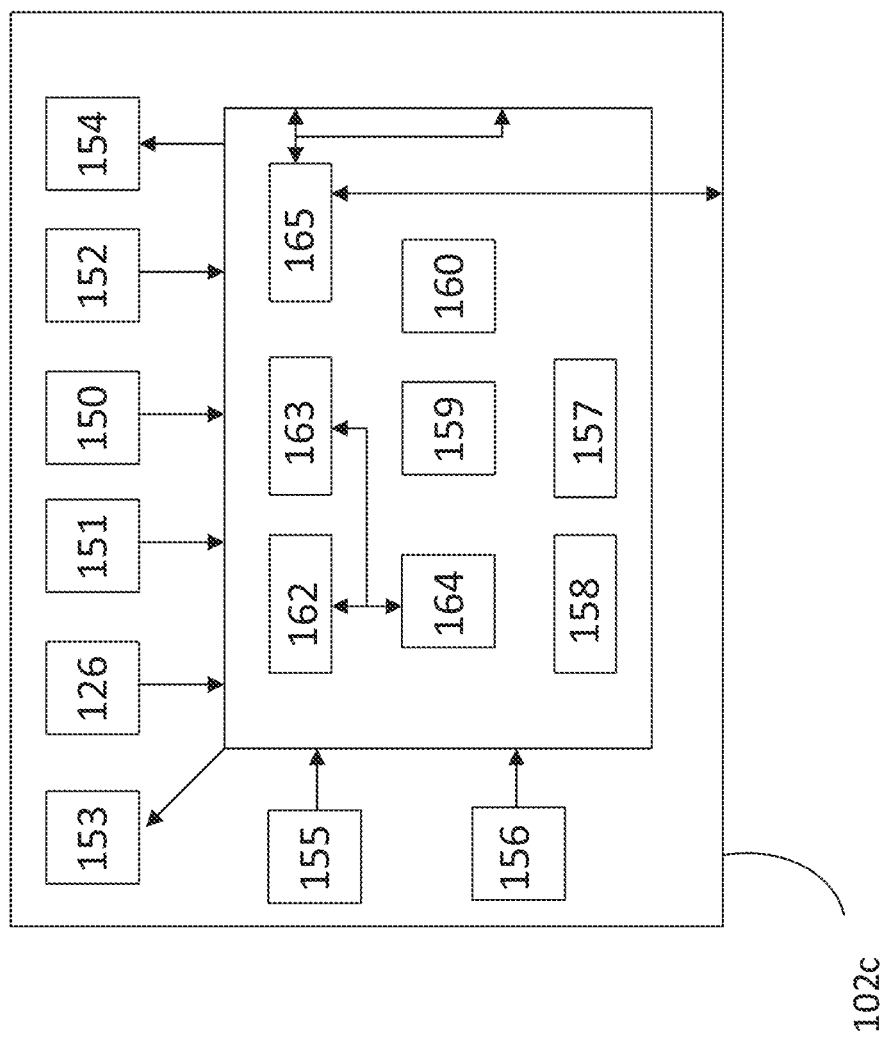
FIG. 2 is a schematic view of one type of capture device.

FIG. 2 is a more detailed functional diagram of one capture device 102c. This version of capture device 102c includes a 3D camera 126. For the purposes of this specification, a 3D camera 126 is a device that creates a topographic map of the surface structure as seen from the viewpoint of the camera. Because the map represents, in some sense, the depth of the surface, the map is typically referred to as a depth map or depth image. Rather than the familiar contours of a topographic map, the surface is typically represented by a finite number of samples—commonly called the point cloud—specifying where particular points happen to lie on surface. The surface itself is typically continuous but can represented by such sample points. The map may be fully-sampled in the sense that there will be a point in the point cloud for every pixel within a two dimensional sampling region of the 2D image sensor (or one of the sensors in the case of a stereo camera) contained within the 3D camera unit. In some embodiments the sampling region will occupy the entire area of the sensor.

Unlike a conventional 2D camera in which the image is uniformly sampled (ie: each image pixel is a predictable angular increment away from its neighbors), the separations of the points in the point cloud depend on the local surface structure and therefore are not necessarily arranged in a completely regular fashion.

In general, a point cloud can be just a list of locations of points in 3D space. In Cartesian coordinates, we can say a point P in the point cloud is located at coordinates [x, y, z]. The sampling is arbitrary. Sampling of the depth image is a bit more constrained however. A depth image P(i, j) consists of the triplets P(i, j)=[x(i, j), y(i, j), z(i, j)] where i and j are the pixel indices of the sensor in the 3D camera.

Suitable 3D cameras include stereo cameras, fully sampled structured light cameras, fully sampled time of flight cameras, depth from focus 3D cameras, light field (or plenoptic) 3D cameras and holographic cameras.

Figure 3:
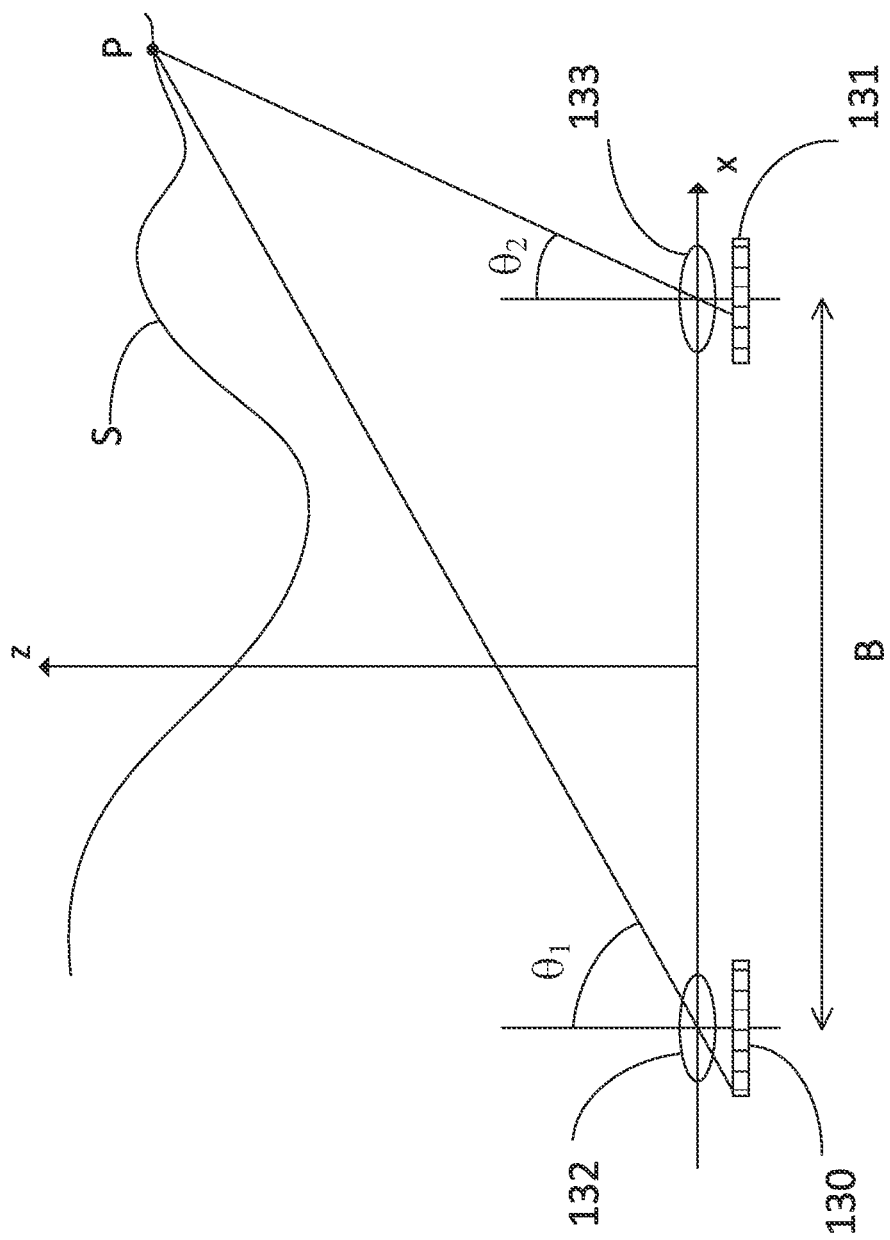
FIG. 3 illustrates one type of 3D camera.

Stereophotogrammetry (often abbreviated to "stereo" and performed with a stereo camera) uses a similar principle to that used by the human eye/brain to provide depth perception. A stereo camera may include two image sensors 130, 131 separated by a known, fixed, baseline B, as indicated in FIG. 3. Triangles are formed between the centers of the two lenses 132, 133 and points on the surface S. For the triangle corresponding to each point, P, the two angles $\theta_1$ and $\theta_2$ are determined by the angles of the rays from each of the sensors to P. The geometry of the triangle is solved to give the [x, z] coordinates of point P. The y coordinate is determined by knowing which sensor rows are being used to image P.

This process is repeated for all relevant pixel pairs (ie: all pixel pairs associated with a common intersection point on the surface) to provide a fully sampled depth image.

Stereophotogrammetry requires that each point P on the surface be correctly identified in each image as being associated with a particular pair of pixels. This is known as the correspondence problem. In practice this requires that the surface contains visible, distinct, details or features. For example stereophotogrammetry will not work well, if at all, on a blank sheet of paper that has no markings.

If the surface does not have intrinsic detail then detail can be added in the form of markings such as physical dots or the like. Alternatively a projector can be used to project a pattern onto the surface. This pattern might resemble the types of patterns used by structured light 3D projectors, eg: lines, grids, dots, etc. This pattern is used as an aid to stereophotogrammetry, and is distinct from a pattern that forms the basis for a structured light 3D camera as described below. The pattern used as a stereophotogrammetry aid does not need to be known or stable between successive stereo frame captures.

In an alternative embodiment the 3D camera may be a fully sampled structured light camera. Structured light devices rely on projecting a known pattern or patterns onto a surface. Simple (non-fully sampled) forms of structured light may project a single point or a single line (emitted by spot or fan lasers respectively), for example as shown in FIG. 4.

In the structured light case the angle ($\theta_1$) of the laser 135 is both fixed and known. Therefore only one optical camera 136 is required. However, because the angle is fixed, the coordinates of only a single point can be determined, ie: the intersection of the laser beam with the surface at point P.

Figure 4:
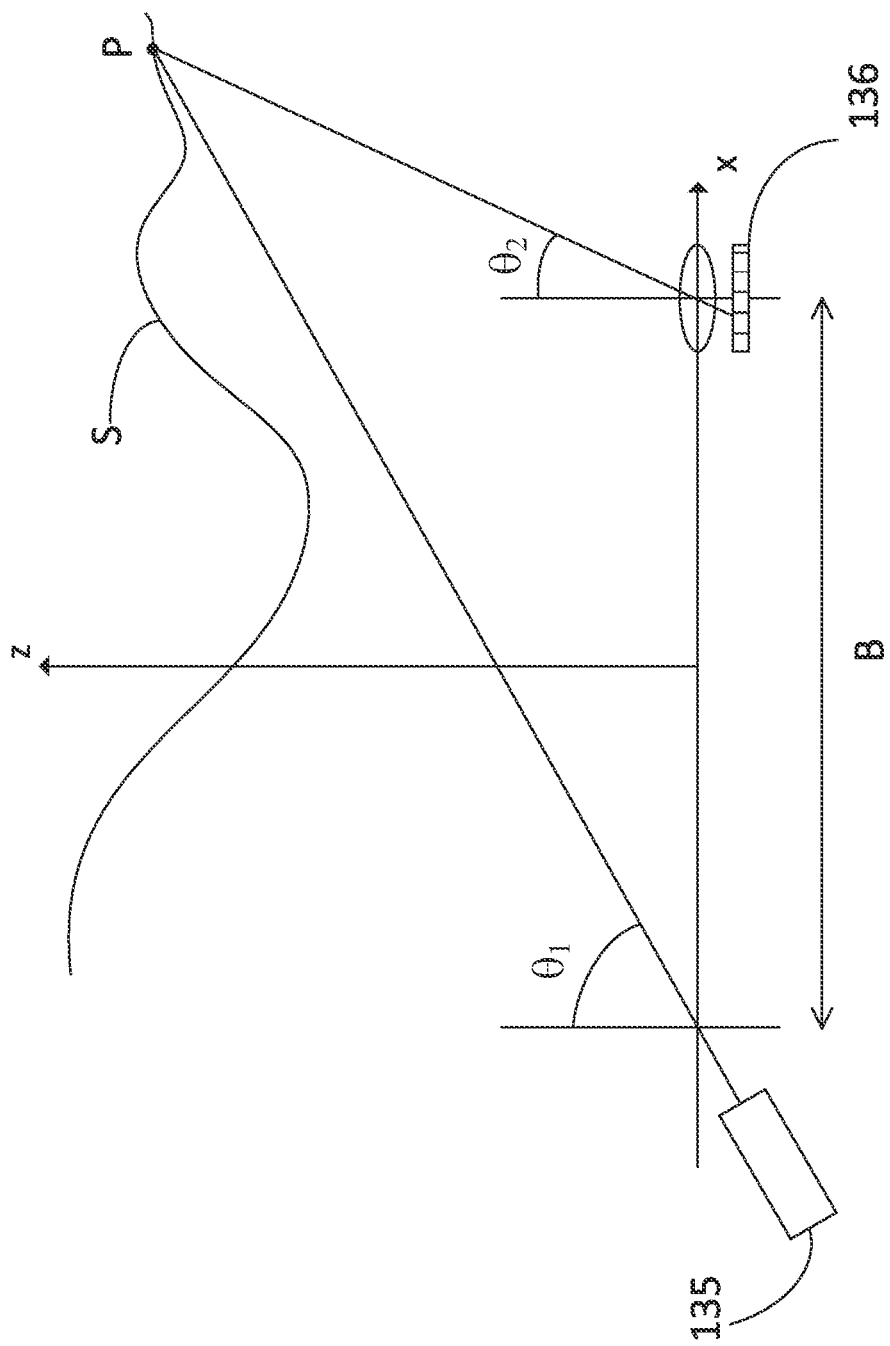
FIG. 4 illustrates another type of 3D camera.
Figure 5:
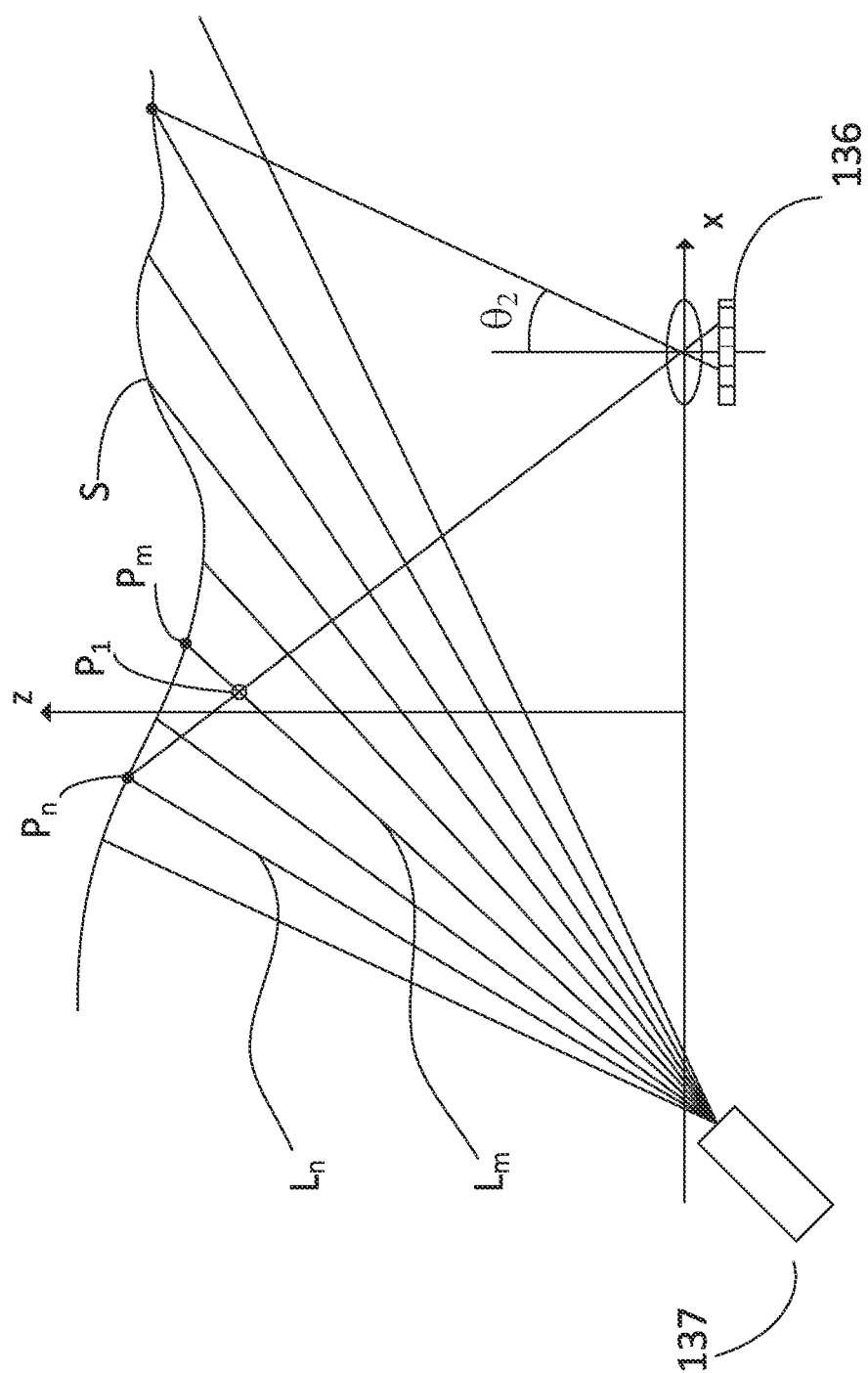
FIG. 5 illustrates a further type of 3D camera.

A fan laser will also emit light out of the plane of the diagram of FIG. 4. Therefore, coordinates of points lying on a line (ie: extending out of the page) can be determined with a fan laser. But the fan laser cannot produce fully sampled 3D from a single image capture. Some devices have used several distinct fan beams or laser spots. However, these also do not produce fully sampled 3D data.

Fully sampled 3D data may be obtained using a structured light pattern that simultaneously illuminates the entire surface. This is conceptually illustrated in FIG. 5, where multiple fan beams are emitted by laser projector 137 and intersect at multiple points Pn, Pm etc. along the surface.

Structured light requires that the projected pattern is constant with respect to angle (which is typically the case except at very close ranges). As the camera's response is invariant with angle, the reflected pattern looks the same to the camera regardless of the target range.

Triangulation methods that rely on correspondence can encounter difficulties with highly oblique surfaces. This is because the feature or pattern appears to be stretched differently when viewed from opposite ends of the baseline.

One limitation of the 'floodlight' approach is that there is now ambiguity regarding which fan laser corresponds to which intersection point. Identification methods such as counting lasers will likely fail in practice. For example if the system misidentifies point Pn as being illuminated by laser Lm instead of laser Ln then it will erroneously assign a point on the surface to the point at P1.

Another difficulty with using multiple fan lasers is that there are gaps in coverage. Parts of the surface are still not illuminated.

Fully sampled 3D structured light cameras use patterns that provide more complete coverage used in conjunction with spatial or temporal coding schemes to uniquely identify which part of the illumination is detected by each sensor pixel (or group of pixels).

Spatial encoding uses dot patterns and spatial correlation. The patterns are pseudo random in the sense that they are (a) fully known and (b) uncorrelated over space (or at least widely separated sub-regions of space). Only one frame is required to compute the depth image.

Temporal encoding illuminates different regions of the surface with mutually uncorrelated sequences of unique binary codes. For example, one direction might be illuminated with a white-white-black-white-black sequence and an adjacent region might be illuminated with a white-black-white-white-black sequence. Because multiple frames are required to produce the depth image, temporal encoding requires that motion is sufficiently small over the course of the entire capture (or, equivalently, the frame rate of the capture is very high).

Figure 6:
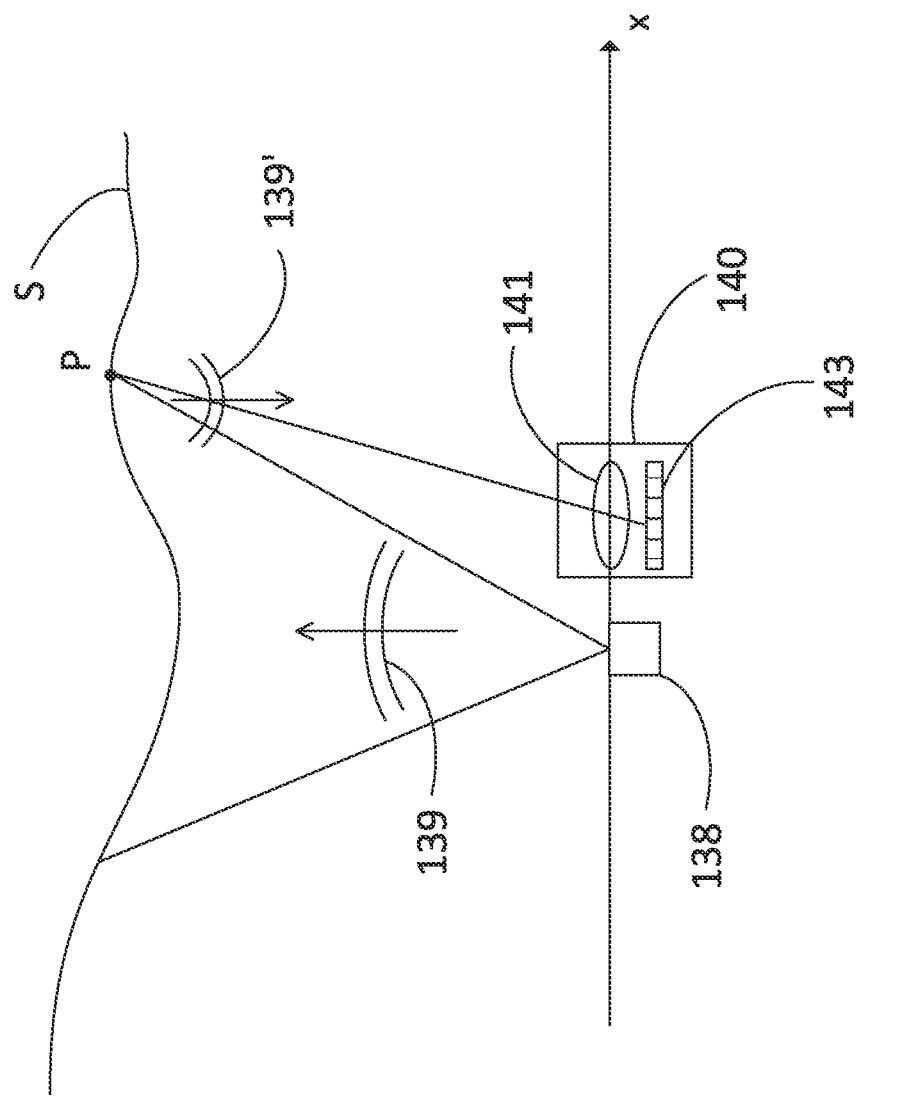
FIG. 6 illustrates yet another type of 3D camera.

In an alternative embodiment the 3D camera 126 may be a time of flight camera, as illustrated in FIG. 6.

Time of flight uses the same basic principles as radar and sonar. Light with unique characteristics, usually in the form of a pulse 138 floodlights the surface S, the times for the reflections 139 (echoes) from the surface to arrive back at the camera 140 are measured, and the ranges to the points P on the surface S are calculated based on the measured times and knowledge of the speed of propagation, ie: range($\theta$) =speed*time/2. The factor of 2 is needed because the time is a round-trip time. The time measurements need to be very precise because the speed of light is very fast. For example, 1 mm change in range is equivalent to 6.6 pico-seconds.

The arrival time for each pixel can be measured by emitting a brief duration light pulse and counting the time taken for the pulse to return. Alternatively, the arrival time can be inferred by emitting a tone burst and measuring the phase of the return. In either case, there can be a range ambiguity, i.e. did the received echo come from the most recently emitted pulse (or tone burst) or an earlier one?

Practical TOF 3D cameras use a projector 138 that illuminates the entire field of view with pulses 139 or tone bursts and a camera 140 for detecting reflected pulses 139'. The camera 140 may include a lens 141 and a 2D array of optical sensors 143 with each pixel of the sensor being connected to its own channel of time measurement circuitry. There is no need for a baseline. Therefore, the projector 138 can be placed very close to camera 140.

In practice, current (low cost) TOF cameras produce depth images that have noise on the order of a few mm, which is too great for wound monitoring applications, unless additional processing such as spatial and temporal averaging is employed.

In a further embodiment, the 3D camera 126 may be a depth from focus camera. Image contrast is maximized when the image is in best focus. This phenomenon is the basis for certain classes of autofocus algorithms used in digital cameras. Not all regions or points on the surface will simultaneously be in good focus when the surface has structure. A 3D camera based on depth from focus exploits these phenomena, specifically:

- Multiple image frames may be captured in rapid succession, each frame with the lens set to a different focal distance.
- Local contrast may be measured over different regions in the image, for example by measuring the variance of the image brightness over a small region of pixels.
- For each region of interest, the focal distance that results in the maximum image contrast represents the distance from the camera to that part of the surface
- Repeat for all regions to construct a depth map Depth resolution may be determined by the size of the lens aperture, ie: the larger the aperture, the smaller the depth of focus, and the greater the depth resolution. It is assumed that motion is negligible and lighting is constant during the captures.

In another embodiment the 3D camera 126 may be a light field (also known as plenoptics) camera or a holographic camera. A light field camera records not only the intensity but also the directions of the light rays. This can be achieved using an array of cameras or an array of micro-lenses located within the optical path. In principle, a single capture of the light field is sufficient to emulate stereophotogrammetry or depth from focus. Holography is related except that it uses coherent light and records the phase of the light as well as the magnitude.

In general, a 3D camera captures a depth map from a single point of view at a single time. Structured light using temporal encoding, TOF with averaging, and depth from focus require multiple frame captures over a short time period. However, because capture times are still relatively small (i.e. the multiple frames are captured in rapid sequence over a very short time period such that device movement between frames is negligible), these are categorized as 3D cameras for the purposes of this specification.

3D cameras that can capture and process quickly enough can be employed to produce real-time depth maps (3D video).

3D cameras may use fixed focus lenses with depth of field (AKA depth of focus) large enough to maintain adequate focus between minimum and maximum ranges to the target, or at least over the maximum variation in surface structure for fixed range operation. This is achieved by using small optical apertures. The smaller the aperture the larger the depth of field, but at the expense of light sensitivity. The reason to use fixed focus lenses is that changing the focus shifts the lens relative to the sensor (at least for simple lenses), which in turn changes the parameters needed in the triangulation calculations. In other words, with variable focus lenses the camera calibration would be more complicated.

Structured light and TOF cameras often use infrared lasers. Infrared enables a visible light image to be obtained with a separate texture camera (i.e. color or RGB camera, though monochrome sensors may also be used) simultaneously with the depth image. Lasers are often used because it is easier to design systems where the pattern is largely invariant with range.

On the other hand, stereophotogrammetry using visible light has the advantage that the texture image is obtained simultaneously with the depth image and without needing a separate texture camera.

3D cameras have a number of disadvantages:
Occlusion. Triangulation based methods only work on those parts of the surface that are in line of sight at both ends of the baseline. This is not such an issue with TOF and depth from focus.
Limited field of view (coverage) of the target. Because the capture is from a single point of view, a 3D camera may not be able to capture depth data from the far side of the object.

These disadvantages may be (largely) overcome by performing captures from multiple points of view, either by having an array of cameras or by multiple captures from a single capture device. When moving a single camera between multiple captures, it is desirable to know the pose (i.e. the position and orientation) of the camera relative to the target. This can be achieved by using mechanical arms and position encoders, or by a suitable tracking arrangement, for example using inertial measurement units (IMUs), magnetic trackers, optical trackers, etc.

Alternatively, or in addition to tracking device pose, Structure from Motion may be used to build up a self-consistent map of the target, ie: keeping track of the relative positions of many features by analysis of the captured image data. However, without knowing the absolute size of part of some object within the scene, the absolute scale cannot be determined. This problem is overcome when a 3D camera is employed in concert with Structure from Motion. The 3D camera provides the absolute scale.

Returning to FIG. 2, the capture device 102c may also include a thermal camera 150 (also known as a thermographic camera, infrared camera or thermal imaging camera). The thermal camera 150 may include a microbolometer array sensor or any other suitable thermal imaging sensor. For assessment of a patient's skin surface, the thermal camera may be sensitive in the long-infrared (wavelengths on the order of 10 um). Variances in temperature at the skin surface or within a wound area may indicate inflammation, infection, necrosis, or the presence of a biofilm. Further, the temperature at the skin surface may be indicative of a level of perfusion within the tissue. Thermal image data may also provide information on the extent or intensity of burns. Sensitive thermal imaging devices may allow variance in temperature over the course of a pulse cycle to be monitored, providing information on pulse rate.

Thermal image data may be registered with and/or displayed with data from other cameras as discussed below.

The capture device 102c may further include an additional 2D texture or RGB camera 151. This may be used to capture RGB image data of the skin surface. It may also or alternatively be used in combination with a UV light source 152 to capture fluorescence data. The UV light source 152 may be configured to illuminate the skin surface with a substantially homogenous intensity of UV light of a wavelength or wavelength range suitable to cause fluorescence in bacteria, biofilms or the like that may be present within a wound or on the skin surface.

The UV light source may be a narrow band device such as a UV light emitting diode. Alternatively, a broader band UV light source may be used, or sources emitting two or more distinct UV wavelengths. The UV light source may emit light with a wavelength in the range 370 to 420 nm. However, in other embodiments, other fluorescence-inducing wavelengths may be used. For example, wavelengths up to 500 to 550 nm, or in the range 350 to 550 nm, may be used. The different wavelengths may excite fluorescence in different bacteria or biofilms. In still further embodiments, multiple fluorescence images may be captured, each using a light source of a different wavelength or wavelength range. Analyzing the different fluorescence signals in these multiple images may allow the signals from different bacteria or biofilms to be distinguished from each other. Multi-spectral cameras may be used to detect fluorescence with increased resolution within the visible RGB spectrum. Hyper-spectral or other cameras may be used to detect fluorescence outside the visible RGB spectrum.

A sufficient number of LEDs may be mounted in the device housing or in a separate add-on device, to give an illumination intensity of 10,000 lux or more at the skin surface, during image capture with the device positioned at a desired capture distance from the skin surface. This high level of illuminance, comparable with a camera flash, is desirable because it will dominate typical room lighting thus making it easier to obtain images with consistent white balance (color temperature). Multiple LEDs emulate a diffuse illumination source which helps reduce specular reflections. Alternatively an optical diffuser or diffusers may be placed in front of the LEDs or other light sources. In other embodiments a lower or higher UV illuminance may be used.

In some embodiments the presence of fluorescence may be detected. In other embodiments the intensity of the fluorescence signal may be measured, and this intensity will depend on the illumination intensity at the skin surface. It may therefore be desirable to guide the user to position the device at a desired range from the skin surface, using any of the guiding methods discussed herein, or any other suitable guiding method. In other embodiments the intensity of the fluorescence signal may be corrected for the range from the device to specific points on the surface. For example, from the three-dimensional image data, the range from the device to each point on the surface can be determined. Based on the range information and knowledge of the UV light source (e.g. the light source power and expected drop off in intensity with distance) a correction factor may be determined for the fluorescence image data set as a whole, or for each pixel within the fluorescence image data set, or for each of a number of sub-regions within the fluorescence image data set. The detected intensity of the fluorescence signal may then be corrected using that correction factor. The correction factor may correct for the effects of range on the intensity of the UV light at the skin surface and/or for the effects (if any) of range on the intensity of the fluorescence signal at the image sensor.

Any suitable optical filters may be used in order to restrict the illumination provided by the UV light source to a desired wavelength range or ranges. Further, any suitable optical filters may be used to restrict the wavelengths incident upon the RGB sensor to the expected fluorescence wavelengths of particular bacteria, biofilms etc. Fixed filters may be used, or tunable filters, such as liquid crystal filters, may be used.

In a further embodiment, the device 102c may be arranged to modulate the UV light source as a function of the sensor frame rate. In this way either a subtraction of background from fluorescence signal can be performed by analysis of different image frames. In a simple case, the UV source may flash on/off every second frame. Then the background ambient light may be subtracted. Motion tracking (as described elsewhere in this specification) may be used to improve the registration between frames. A background subtraction may be performed with as few as two frames (one with UV light source on and one with UV light source off). Averaging over a larger number of frames may improve the final data.

In a further embodiment the device 102c may be configured to switch the UV light source on during a first time period and then off. Immediately after the UV light source has been switched off, a plurality of images of the patient's skin surface may be captured. As the images are captured over a period of time, the fluorescence intensity in each image can be analysed and generally will fall away over time. By analysing fluorescence in each of the plurality of images a fluorescence lifetime or fluorescence decay profile can be determined. The fluorescence lifetime or decay profile may be characteristic of a particular bacteria or biofilm.

In further embodiments the device 102c may communicate with the building's environmental control system or a local lighting controller to momentarily turn off the room lighting during capture of the fluorescence image in order to improve the contrast of the image, ie: by reducing or eliminating ambient light.

In further embodiments the fluorescence signal may be captured in 3D images by the 3D camera 126, rather than by a separate texture camera. This may require either a 3D camera capable of capturing RGB data, or a 3D camera with suitable filters.

Fluorescence image data may be captured without the use of added dyes or contrast agents, or in appropriate cases dyes or contrast agents may be applied to the patient's skin surface if desired.

Bacteria believed to fluoresce include *Pseudomanas aeruginosa, Pyoderma gangrenosum, Serratia marcescens, Viridans streptococci, Staphylococcus aureus, Staphylococcus epidermidis, Corynebacterium diptheriae, Enterobacter, Enterococcus*. Various other bacteria and/or biofilms of interest may also fluoresce and the invention is not limited in this regard.

Fluorescence image data may be registered with and/or displayed with data from other cameras as discussed below.

The capture device 102c may include one or more further capture devices 152, from a group including but not limited to: an ultrasound A or B mode device, a Doppler ultrasound device, an ultrasound elastography device, a terahertz RADAR device, a spot temperature probe, a code reader (such as a barcode or QR code reader, RFID reader etc.), a biometric reader (such as a fingerprint scanner, retina or iris scanner), microphone, a video camera, a location system (such as GPS or a local location system dedicated to the use environment), an IMU, an oximeter, a pulse oximeter, an odor sensor, a pH sensor, a moisture sensor.

The capture device 102c may also include a guiding module 153. The guiding module 153 may be configured to implement any of the guiding arrangement discussed herein, in order to assist the user in correctly positioning and/or orienting the capture device 102c during capture of data.

The capture device 102c may also include one or more illumination sources 154. These may include one or more white light sources, one or more UV sources, other sources for exciting fluorescence. The illumination sources may also include an overlay projector that is configured to project an image onto the skin surface. The image may be a guide image as discussed below. The projector may also be used to project wound information onto the wound. For example, a visible projection based on thermal or fluorescence data not visible to the human eye may be projected onto the wound to indicate wound properties to a healthcare professional. A region of infection may be identified by such a projection, for example.

The capture device 102c may include one or more tracking devices 155, including inertial measurement unit (IMU) devices and/or magnetic tracking devices.

The capture device 102c may include an actuator or trigger 156, such as a button that will cause the capture of data when actuated by a user.

The capture device 102c may include a battery 157, user interface 158, image display 159, status display 160. Other user input and/or display devices may be provided. User input and/or display functions may be combined in touchscreens or similar devices.

The capture device 102c may include a processor 162 and controller 163. A synchronization module 164 may ensure correct switching of the various cameras and other data capture units.

A communications module 165 may control communication over any suitable wired or wireless links to external devices, networks, storage, servers etc., e.g. as discussed above with reference to FIG. 1.

Figure 7:
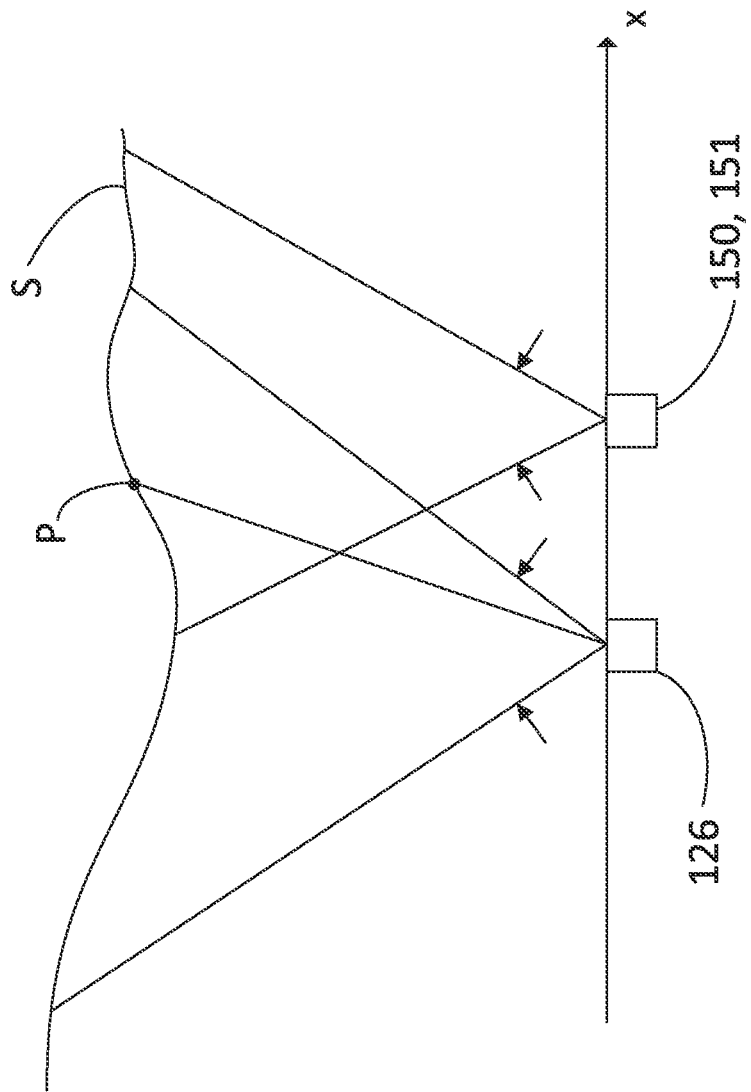
FIG. 7 illustrates a device including a 3D camera and a further camera.

FIG. 7 shows how three-dimensional image data from the 3D camera 126 may be registered with data from a texture camera 151 or thermal camera 150. A point $P_1$ on the surface S is known in the three-dimensional data set. The relative positions of the 3D camera 126 and texture or thermal camera 151, 150 are fixed and known. A projection can be taken from point $P_1$ back through the optical origin of the camera 151, 150 to identify a point on the sensor of that camera 151, 150. That sensor point may correspond to a pixel, or the signals from a group of pixels may be averaged to provide a value for the sensor point. The texture or thermal image data may thus be registered to the three-dimensional image data.

This registration method is only possible within the field of view of the 3D camera 126, i.e. in a region where the fields of view of the 3D camera 126 and the texture or thermal camera 151, 150 overlap. The overlap between the captured images depends on the range to the skin surface.

A similar registration may be performed for any number of image data sets captured by the capture device 102c, so that e.g. thermal, RGB and fluorescence data sets may all be registered with the three-dimensional image data set.

It may be desirable to fill "holes" in the 3D data set. Holes in this context are locations in the depth map capture which are missing. A 3D location for this missing pixel cannot be determined, and therefore cannot be projected into the other cameras as discussed above. Therefore, such holes may propagate through all datasets. To resolve this issue, some form of interpolation may be applied to the depth map to create a virtual depth at the missing location within the depth map. Once this has been performed, the interpolated 3D location can be used in the subsequent projections/processing.

The interpolation of the depth map may be achieved using a range of interpolation techniques, although in general they all perform the same basic function of generating a valid depth at the given location based on the surrounding values. In one embodiment, the x,y values of each location within the 'hole' may be generated using separate linear interpolation, then the z value may be generated using a 2D spline from the surrounding locations.

The x value of the hole may be determined by testing each pixel directly upwards and downwards until a valid pixel is found (perhaps more than 1-pixel away for larger holes). Once the up/down valid pixel locations have been found, the x value may be calculated by linear interpolation of the x values from each of these endpoint points. A similar process may be applied for the y value except in the horizontal direction. Higher order interpolation can be implemented by using additional valid x and y values.

The z location of each pixel within the hole may be generated using a 2D spline using a "donut" of all the points surrounding the hole. The 'width' of this donut may be adjusted, in one embodiment a value of about 3 pixels may be suitable. These points may be used to calculate the 2D spline, then the z-value of each location within the hole calculated from its freshly generated x,y value. A common spline may be used for all points within the hole, evaluated at the x,y location of each point within the hole.

As noted above, the Applicant's system may include a number of different capture devices 102, 102a, 102b and 102c, including devices disclosed herein and/or devices as disclosed in U.S. Pat. No. 8,755,053, filed May 11, 2009; U.S. Pat. No. 9,179,844, filed Nov. 27, 2012; U.S. patent application Ser. No. 15/144,722; and U.S. Provisional Patent Application No. 62/423,709 filed 17 Nov. 2016, the entire contents of which are hereby incorporated by reference. Further devices, including devices supplied by other parties, may also be supported.

The various devices each provide a set of captured data that may differ from the data provided by other devices. For example, one device may provide a full data set including for example three-dimensional image data, thermal image data, texture image data and fluorescence image data, wound cap area, wound bed area, wound volume, average and maximum depth. This first device may provide data at a high level of accuracy such that a high level of confidence can be placed in, e.g. the calculated wound volume. A second device may provide a data set including texture image data and structured light (i.e. non-fully sampled) data, wound bed area and wound volume. The second device does not provide full 3D data and the level of confidence in the calculated wound volume may therefore be lower. A third device may provide a data set including only a texture image with approximate scale information. While a 2D wound area can be calculated, a wound volume is not provided. Further, the level of confidence in the wound area may be lower still. Any of the data sets may also include details of a current treatment regime, such as types of dressings applied, drug(s) being administered, dosage, when given, etc.

Figure 8:
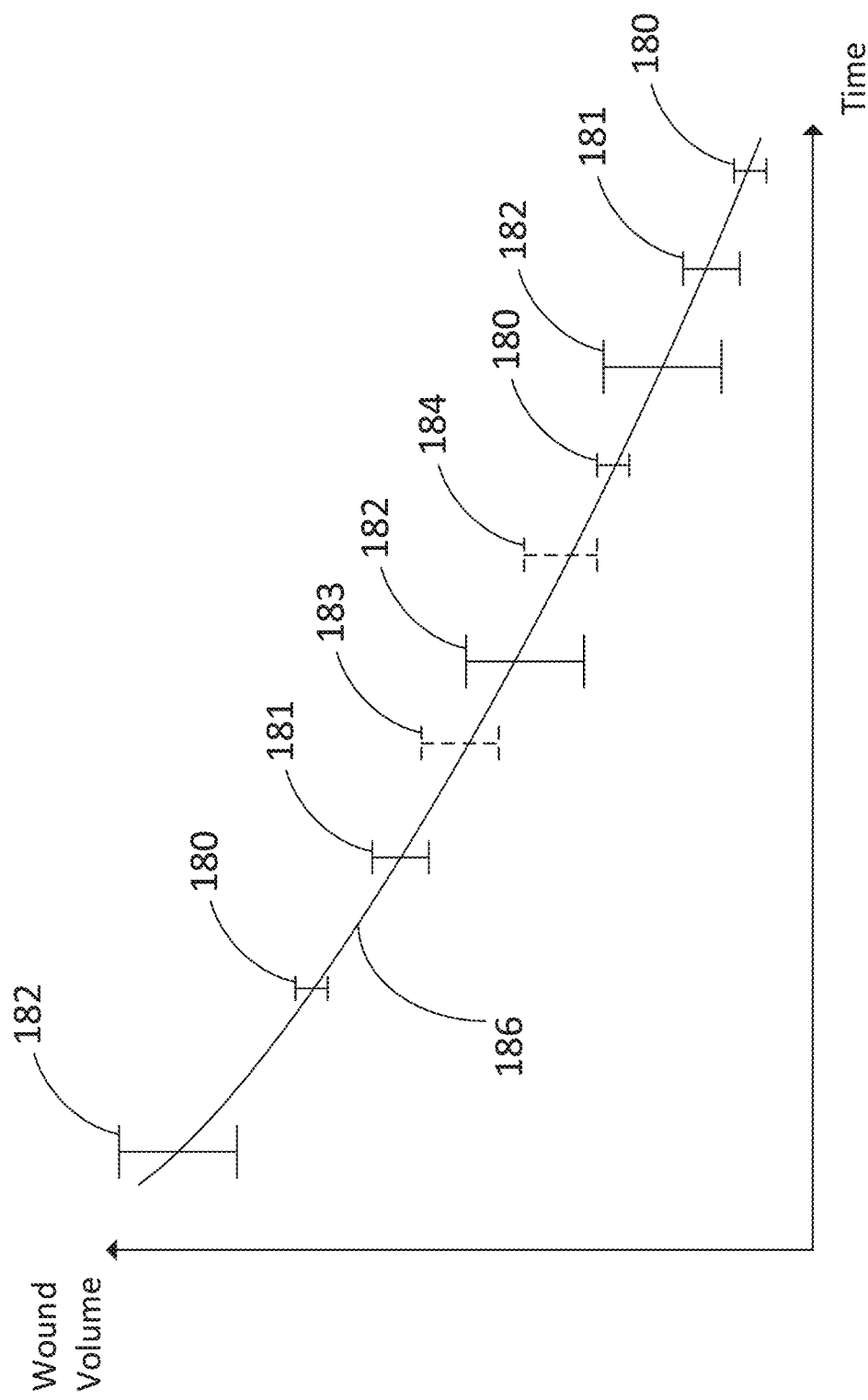
FIG. 8 illustrates data weighting or uncertainty and interpolation.

The Applicant's facility addresses these issues by interpolating and/or extrapolating from the fuller data sets to fill the gaps in other data sets. For example, FIG. 8 represents wound volume data based on data captures spread over time. Data points 180 carry relatively small error bars representing the high level of confidence. These data points may correspond to data capture using a device with fully sampled three-dimensional data. Data points 181 carry larger error bars, representing a lower level of confidence. Data points 182 carry still larger error bars, representing a still lower level of confidence. Dashed data points 183, 184 represent interpolated data, where no wound volume data can be obtained from the data set obtained at those time points. In a simple case, data point 183 may be interpolated from the two adjacent data points 181, 182, and data point 184 may be interpolated from the two adjacent data points 182, 180. However, more sophisticated interpolation methods may be used, and are well known.

A wound volume curve 186 may be fitted through the data points using any suitable fitting method. Alternatively, the healing progression may be represented as a band rather than a line alone or line with error bars. The width of the band would indicate the uncertainty of the measurements.

As an alternative to the error bar approach illustrated in FIG. 8, each data point may be assigned a weighting or confidence value that can be used as an input to interpolation or extrapolation, and to a curve fitting method.

Similar interpolation and/or extrapolation methods may be applied to other elements of the full data set, such that a data set at each capture time includes either captured or interpolated/extrapolated data for each element of the full data set.

Figure 9:
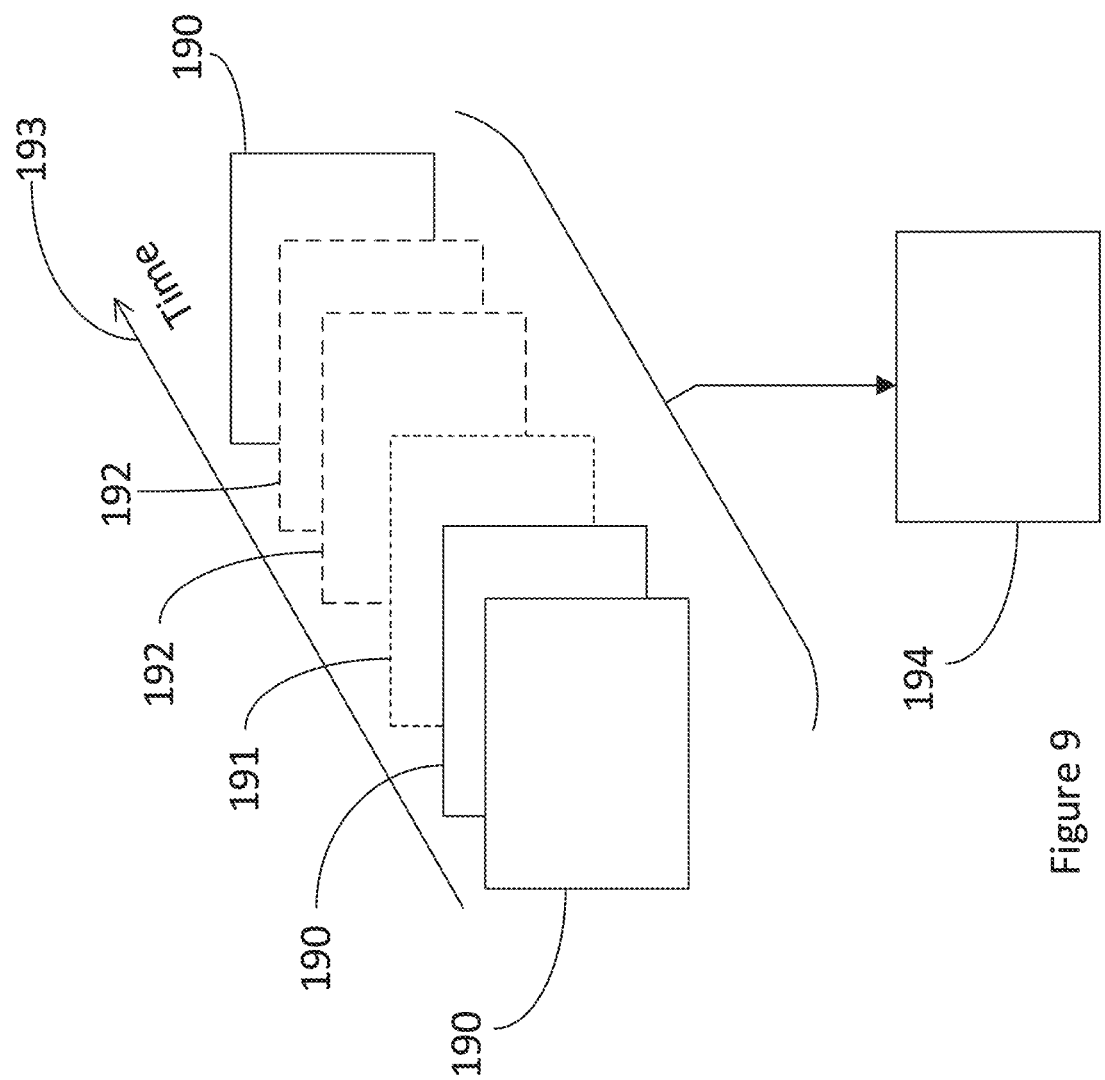
FIG. 9 illustrates datasets captured by different capture devices.

This arrangement facilitates display of data, as illustrated in FIG. 9. Each rectangle 190 represents a full data set captured by a first capture device. Each rectangle 191 represents a data set including a partial data set captured by a second device and, optionally, extrapolated or interpolated data to create a full data set. Each rectangle 192 represents a data set including a partial data set captured by a third device and, optionally, extrapolated or interpolated data to create a full data set. As indicated by axis 193, each data set corresponds to a particular capture time.

Images or representations taken from or based on the data sets may be displayed individually, or in windows, or cascaded, or in any other suitable display configuration on any suitable display screen, touchscreen, head mounted display or the like.

Alternatively, the data sets may be combined to form an animation, GIF or video clip indicated schematically at rectangle 194. Further image frames may be created based on the existing data sets, e.g. by direct copying or by interpolation/extrapolation from the existing data sets. In this way an animation or video clip showing the development or healing of a wound over time may be created and displayed in uniform temporal increments to a user on any suitable display screen, touchscreen, head mounted display or the like.

Displayed data, whether in still image or animation/video form, may include any combination of: a representation based on the three-dimensional image data (i.e. the point cloud). This representation may be any suitable projection from the three-dimensional point cloud onto a two-dimensional plane. Alternatively, any other suitable method for displaying the three-dimensional data may be used. Various such display methods are known and need not be described in detail here.

Further, the displayed data may be selected from the full data set. For example, a user may use checkboxes or some other selection interface to select "3D model" and "thermal". The displayed image may then include a representation of the 3D model with thermal data overlaid as a heat map or similar. A graphical slider control may be used to proportion the transparency of the overlay. Similarly, texture and/or fluorescence data may be overlaid. Other data may be displayed in text, graphic or any other suitable form. In general, any desired combination of data from the full data set may be displayed to a user.

A user may manipulate the displayed data via a suitable user interface, such as a touchscreen, pointer (e.g. mouse), keyboard, trackball, scroll wheel, voice recognition etc. The user may be enabled to rotate the displayed representation, zoom in or out, pan, add markings, notes, define regions of interest, define or adjust feature boundaries, regions or sub-regions.

In general data may be captured at any desired time, for example: at admission to a medical facility, at any consultation with a healthcare provider in a hospital, community clinic or in a home care situation, or when a patient changes healthcare facility. Captured data may be used in healthcare assessments and may feed into decision making around wound treatments. Captured data may also be used to justify decisions to insurers, for example a decision to admit or re-admit a patient or choose a particular treatment path. Captured data may also be useful in assessing liability. For example, data captured at admission may be used to establish pre-existing conditions, for which the medical facility will not be responsible. Captured data may feed back into a choice of capture devices. For example, the data may indicate that the wound is progressing favorably and that future data captures may be performed with a less sophisticated capture device. Alternatively, the data may indicate that wound progress is outside of expectations and that data should be captured at greater accuracy with a more sophisticated device.

In some applications it may be desirable to move or re-position the capture device between data captures. For example, a wound may extend sufficiently far around the circumference of a patient's limb that it is necessary or desirable to view the wound from two or more device poses in order to construct an acceptable 3D model. The data sets captured from each pose may be combined to form a three-dimensional model. The combination of data sets may be performed by tracking movement of the capture device between the poses, or by identifying common features in the captured data sets allowing registration of those data sets, or a hybrid of these two approaches that relies on tracking device motion and registration between data sets.

The capture device may include a number of accelerometers and/or magnetometers and/or gyroscopes and/or other sensors, which together can be considered an "Inertial Measurement Unit" or IMU (also known as an Attitude and Heading Reference System (AHRS)). In some fields an AHRS may be considered to include an IMU and a processor. In some fields an IMU may be considered not to include a magnetometer. However, for the purposes of this specification the term IMU is to include all such IMUs (with or without magnetometers, and with or without processors) and AHRSs.

The IMU may be used to track capture device movements while capturing two or more data sets from different device poses. The pose of the capture device for each data set is therefore known from the IMU, or at least the relative changes in pose between data captures are known.

In other embodiments any suitable location or pose-determination system may be used, including magnetic tracking systems etc. Such systems may use one or more reference beacons located in any suitable position, including beacons mounted in a room, portable beacons or beacons attached to the patient. Such beacons may be optical (active or passive), RF, acoustic or any other suitable beacons.

In some embodiments the two or more data sets may be captured substantially continuously as the capture device is moved. Alternatively, a smaller number (e.g. 2 to 10) data sets may be captured over a short period of time, preferably after the motion between captures is sufficient that there is a meaningful change in pose but not so great that there is no overlap between the previous capture and the next capture. This strategy results in less data to store and process. In some embodiments the data sets may be captured all in response to a single user data capture instruction. In other embodiments a single user capture instruction may be required for capture of each data set.

Registration between the captured data sets may be performed based on skin features. In addition, since these data sets are captured sequentially over a very short time period, the skin feature of interest (ulcer, wound etc., especially the boundary of the skin feature) will not change over the data capture period and may be used as an input to the registration process.

Registration may be performed using any available image data, including three-dimensional image data, texture or RGB image data, thermal image data, fluorescence image data etc. The registration between data sets may be aided by anatomical fiducials as described below and/or by temporary or applied fiducials. Temporary or applied fiducials may include one or more visible fiducials such as reference objects, applied markings etc., that will be detected in texture or RGB image data; one or more 3D fiducials having a shape in three dimensions, such as reference objects, applied raised markings etc., that will be detected in three-dimensional image data; one or more applied fluorescent fiducials, such as fluorescent materials or fluorescent ink markings that will be detected in fluorescent image data; and/or one or more thermal fiducials such as applied materials or markings, or locally heated or cooled objects, markings or regions of the patient's skin, that will be detected in thermal image data.

In further embodiments, simultaneous localization and mapping (SLAM) methods may be used to map the skin surface based on several images captured by the capture device from different positions. This may be done based on the available image data alone, or in some embodiments the image data may be combined with the tracking of the device position by the IMU.

Guide information may be overlaid on the display to assist the user to move the device in the correct manner during capture of such a sequence of data sets, maintaining an acceptable device pose, orientation and/or range.

Figure 10:
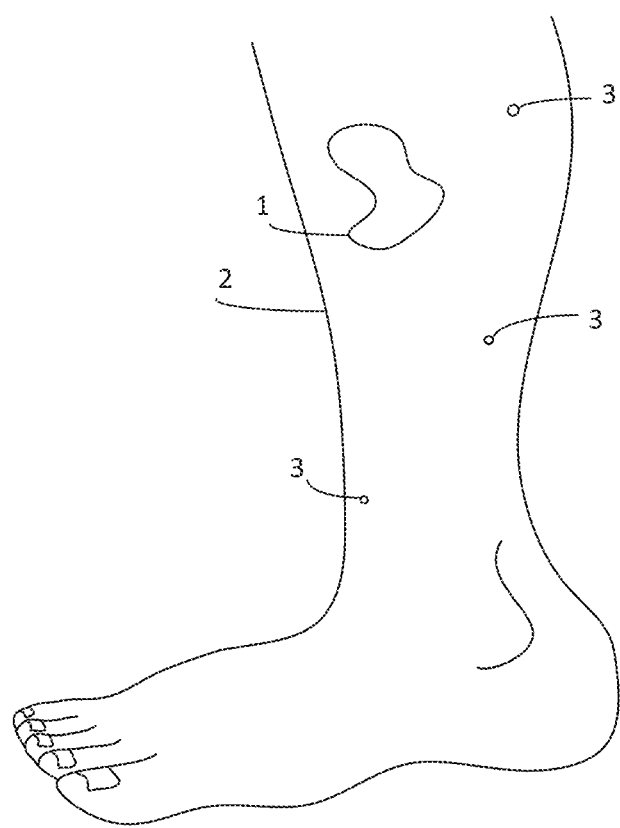
FIG. 10 shows a patient's leg, with a wound, ulcer, lesion or other surface feature of interest.

FIG. 10 shows an anatomical surface feature 1, such as a wound or ulcer, on the leg 2 of a patient. A user (e.g. a healthcare professional or caregiver) may capture a data set including one or more images of the patient's leg 2, including the wound 1, using the capture device 102, 102a, 102b, 102c (FIG. 1).

Dimensional information for the wound 1 may be obtained by analysis of the captured data. For some devices dimensional information may be obtained from three-dimensional image data, structured light data or the like. In the absence of any calibration or scale information the dimensional information obtained may be in arbitrary units, i.e. the dimensional information will not necessarily represent a true measurement of the ulcer. For example, analysis of the image may provide an ulcer length of 5 units, an ulcer width of 3 units and an ulcer area of 11.8 units squared (with the area being calculated by the well-known Kundin method, i.e. length times width times Pi/4). Alternatively, area may be calculated by counting the number of pixels in the captured image that fall within the outline of the wound; or by any other suitable method.

The captured data set may be stored in any suitable database and/or as part of any suitable electronic health record, together with the dimensional information, date information, patient identification information, wound or ulcer identification information (for patients with several wounds or ulcers), address details, treatment information, billing information etc. Any of these data may be input by the user and/or retrieved from the database or other data store. The retention of this data allows comparison with data captured at a later time, and for trends in development or healing of the wound to be monitored over time.

As shown in FIG. 10, the patient's skin surface may include a number of markings or other permanent or semi-permanent skin features 3, such as moles, freckles, birthmarks, skin wrinkles, creases, lines, tattoos (permanent or temporary tattoos), scars or the like. Such permanent or long-term, fixed points or markings on the patient's body may be termed "anatomical fiducials". In some embodiments, a permanent or semi-permanent marking may be added (using e.g. a pen, tattoo etc.) in order to provide an anatomical fiducial. Such markings may be in any material/ink etc. detectable by any image sensor included in the capture device (e.g. fluorescent ink markings may be detected in fluorescence imaging). This may be done in addition to existing anatomical fiducials, or in a surface region where no or insufficient suitable anatomical fiducials are found.

Such fiducials may assist in registration between data sets captured at different times, and/or between data sets captured relatively close in time but at different device poses.

Registration can be based on points shared between data sets, such as the outline of the patient's leg, bone structures, and any anatomical fiducials 3, such as moles, freckles, birthmarks, skin wrinkles, creases, lines, tattoos, scars or the like. For registration between data sets captured over a short time period, points in fluorescence and/or thermal images may be used.

In some embodiments transformations may be used to cater for different perspectives between images, different camera types, different camera focal lengths or fields of view, different ranges between camera and skin surface etc.

Figure 11:
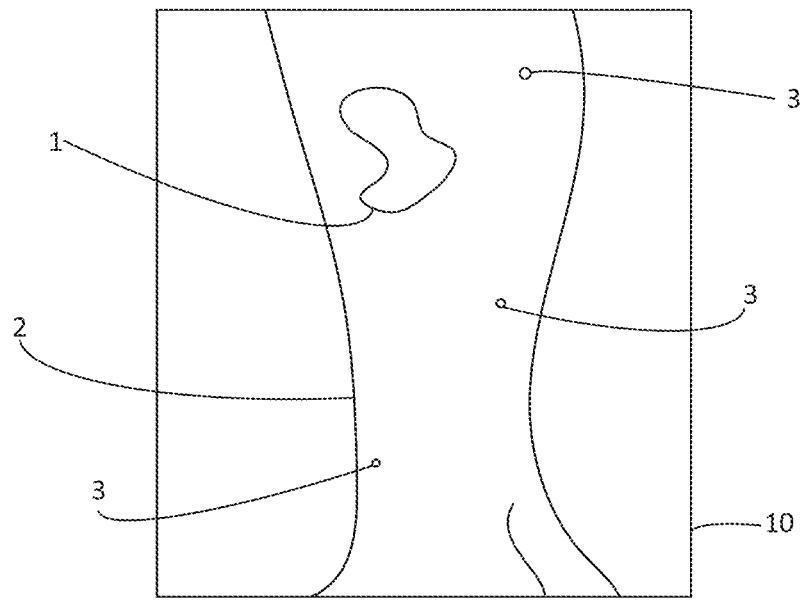
FIG. 11 shows a further image of the patient's leg of FIG. 10.

The user may be guided to position and orient the device with a desired pose relative to the patient's skin. FIG. 11 shows an image 10 of a patient's leg 2 captured at a first time and including a skin feature 1. The image 10 may show anatomical fiducials 3, as discussed above.

Figure 12:
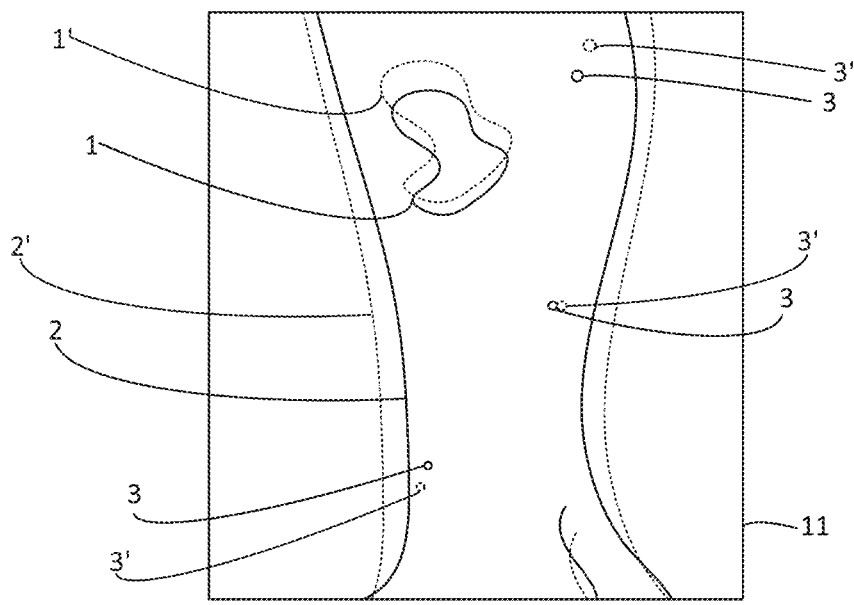
FIG. 12 shows a device display with a real-time camera feed and overlaid guide.
Figure 13:
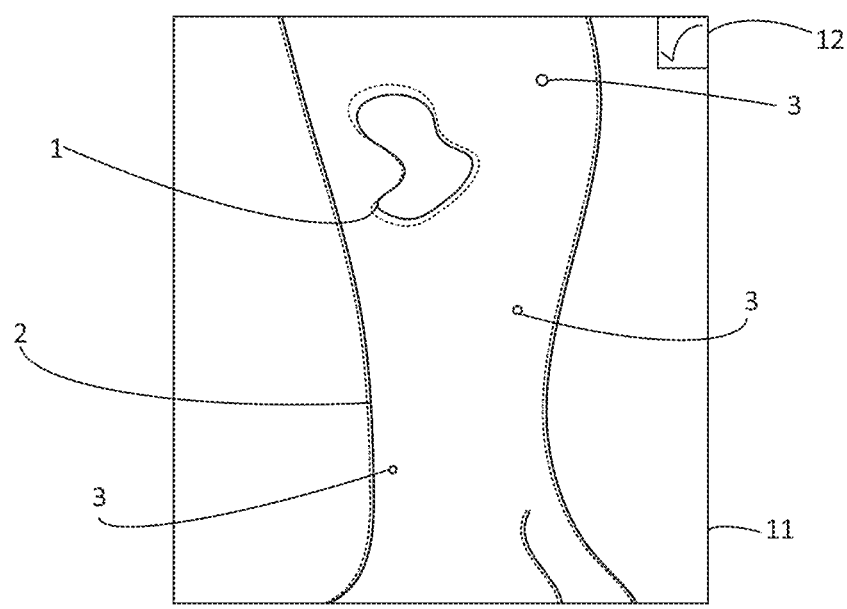
FIG. 13 is a further view of the display of FIG. 12.

FIG. 12 shows a device display 11 at a later time. The display shows a real-time camera view (shown in solid line) and an overlaid guide (shown in dashed line). The overlaid guide may simply be an overlaid image of the skin surface captured previously (such as the image 10 of FIG. 10). FIG. 12 shows that the device is not properly positioned. The camera view is misaligned with the guide, having a different perspective and scale. A user may align the device with the desired position by moving it to bring the camera view into alignment with the guide, as shown in FIG. 13. Correct alignment of the device may be determined by the user, by observing the alignment of camera view and overlaid guide. Alternatively, the device may detect the alignment of camera view and guide and when an acceptable level of alignment is reached provide feedback in the form of an audio, visual or audiovisual notification. For example, when acceptable alignment is achieved the device may beep. Or the quality of the alignment may be indicated, for example by the pitch, volume or other characteristic of the audio signal, to inform the user if he/she is moving the device in the right direction or otherwise. In the embodiment shown in FIG. 13, a visual indicator 12 may be displayed when acceptable alignment is achieved.

In some embodiments the device may automatically capture data when an acceptable alignment is detected. In other embodiments the user may issue a data capture instruction (for example by pressing a button, touch screen etc., or by any other suitable user input).

In other embodiments, the guide may be one or more portions of a previously captured image of the patient's skin surface. For example, it may be desirable to remove the wound 1 from the guide image, since the shape of the wound 1 may change over time, so that using the wound 1 in the guide image may confuse the user. Similarly, the background (e.g. tables/beds/equipment etc. visible in the image) may be eliminated from the guide image. Alternatively, the guide may comprise one or more guide masks or markings based on a previously captured image of the patient's skin surface. For example, guide markings may be generated based on the position of anatomical fiducials 3, or the outline of a user's limb, or positions of bone features etc. In still further embodiments, one or more guide masks or markings may be selected from a library of available guide masks or markings (e.g. a lower leg mask may be used, having a shape corresponding to the average lower leg).

A guide may be generated from a previously captured image. Where the capture device 102c includes a 3D camera, the guide may be based on previously captured 3D data.

In a scanning mode involving data capture from a plurality of device poses, a guide may be projected or displayed to indicate regions that have already been scanned. The guide may also indicate any areas where there are holes or bad data in the 3D data set. This information may be color coded or otherwise distinguished.

Text or graphics may be projected.

Guide information may be displayed using a virtual overlay dike Google glass or equivalent, or a Virtual Reality display such as DAQRI).

Further, when data is captured using a device 102 including a 3D camera, absolute dimensional data is obtained. Such data may be used to assist in calibration of data obtained with a simpler device. In some applications it may be desirable to gather full 3D data at a medical facility, or for full 3D data to be gathered by more skilled users such as medical professionals, using more capable devices. Other data can be gathered by less skilled users, possibly at remote locations, such as patient's homes, using more ubiquitous devices such as Smartphones, digital cameras, tablets etc. 3D data can be used to calibrate other data obtained either earlier or later than the 3D data.

In further embodiments fully scaled or calibrated data may be gathered at each data capture.

Where user supplied fiducials are used, these may provide a means to match image properties (e.g. exposure and/or white balance) between different images (possibly captured by different devices) allowing those images to be consistently displayed and compared. In other embodiments image properties (e.g. exposure and/or white balance) may be corrected (or at least made consistent between different image captures) by analysis of skin tones etc. Further, the device may be arranged to issue alerts to the user if lighting is outside a desired range, such that captured images have unacceptable exposure or white balance.

User-supplied fiducials may also contain machine readable indicia, such as bar codes, QR codes, RFID elements or any other suitable indicia. Such machine readable indicia may encode any desired data, including patient identification information, date information, wound information, and/or user information (e.g. healthcare provider identification). Machine readable indicia may be read from image data captured by the capture device, for example by identifying and reading a QR code in the image. The image data may be the image data captured for analysis of the anatomical surface feature. Alternatively, further image data may be captured. Alternatively, the machine readable indicia may be read over any suitable wired or wireless link (e.g. Bluetooth or reading by an RFID reader). Machine readable indicia may allow other captured data or medical samples to be correctly associated with the patient or anatomical surface feature data. Machine readable indicia may also be used to ensure that supplies (e.g. the fiducials) are not being reused for different patients.

Consistent scale across displayed images is also desirable, since it allows meaningful comparisons to be made. Images may either be captured at a consistent scale, or may be scaled for consistent display, assessment and/or measurements.

Figure 14:
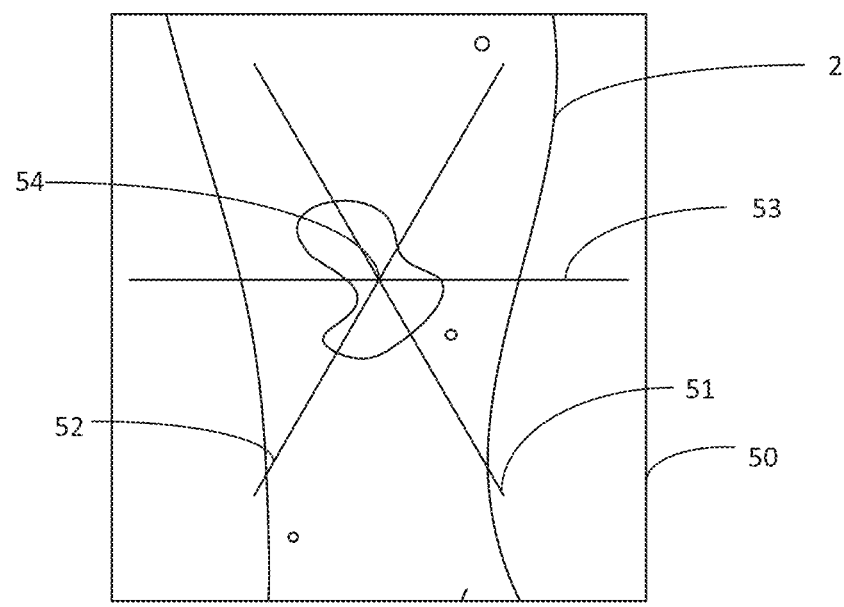
FIG. 14 shows a device display with real-time camera feed and overlaid guide, at a desired range.

FIG. 14 shows a device display 50 showing a real-time camera view of a patient's limb 2. Three guide lines 51, 52, 53 form a star pattern, with the three lines crossing at a single crossing point 54. This indicates that the range is correct and the user may capture data at that optimum range by pressing button, touching a touch screen or issuing some other suitable user capture instruction.

Figure 15:
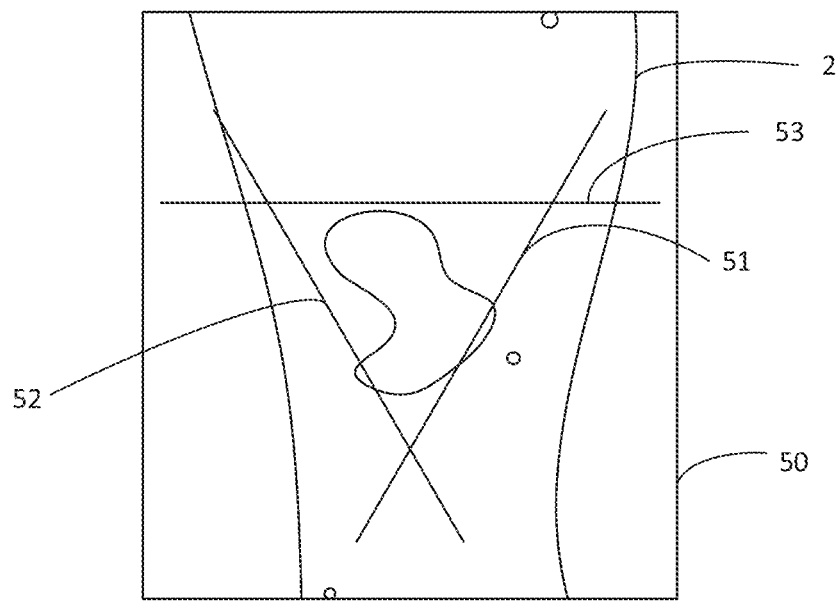
FIG. 15 shows the display of FIG. 13, at a closer range.

FIG. 15 shows the same device display 50 where the device is further away from the patient's skin than the optimum distance. Here the three guide lines 51, 52, 53 form a triangle, i.e. they do not meet at a single point. As the user moves the device towards the skin the triangle will reduce in size, with the guide lines 51, 52, 53 moving closer until they meet as in FIG. 13, when the distance is optimised.

Figure 16:
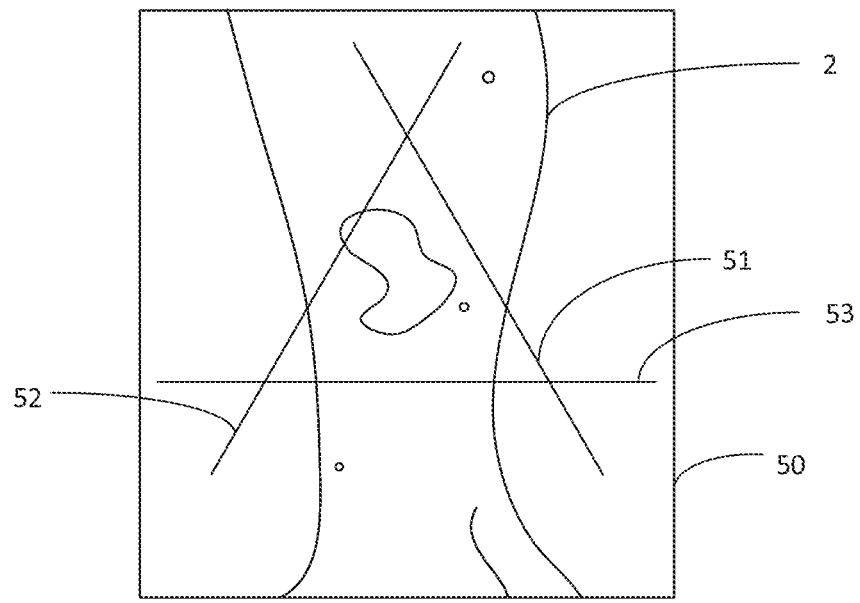
FIG. 16 shows the display of FIG. 13, at a farther range.

FIG. 16 shows the same device display 50 where the device is closer to the patient's skin than the optimum distance. Here the three guide lines 51, 52, 53 form a triangle, i.e. they do not meet at a single point. The triangle in this figure is inverted when compared to the triangle of FIG. 14. As the user moves the device away from the skin the triangle will reduce in size, with the guide lines 51, 52, 53 moving closer until they meet as in FIG. 14, when the distance is optimised.

In other embodiments a different number of guide lines may be used. For example, four lines could be used, forming a square or rectangle, or five lines could be used forming a pentagon. However, in some embodiments the polygon will diminish in size as the optimum range is approached, with all lines crossing at a single point at the optimum range.

In still further embodiments different kinds of visual indicator, such as red and green lights or symbols, may be displayed to indicate to the user how to move the device towards an optimum range. A sliding indicator on a scale could be used to show the current range and the desired or optimum range. A circular indicator or gauge could be used, showing the current range and the desired or optimum range. An audio indicator could be used. For example, the device may beep when within some tolerance of the desired or optimum range. Alternatively, a variable tone or volume sound could be emitted to guide the user to move the camera closer to, or away from, the patient, with the sound, tone or volume determined by the range.

Further, the device may be configured to automatically capture data when the user has positioned the device at the optimum range. This may allow data to be captured without requiring a button or touchscreen to be pushed or touched, reducing camera shake.

In further embodiments the device may capture video data over a time period while the user moves the device through a range of positions and/or orientations and/or ranges. The user may be guided in the required movement of the device.

The capture device may automatically select and/or retain video frames when an acceptable alignment and/or range is detected.

Figure 17:
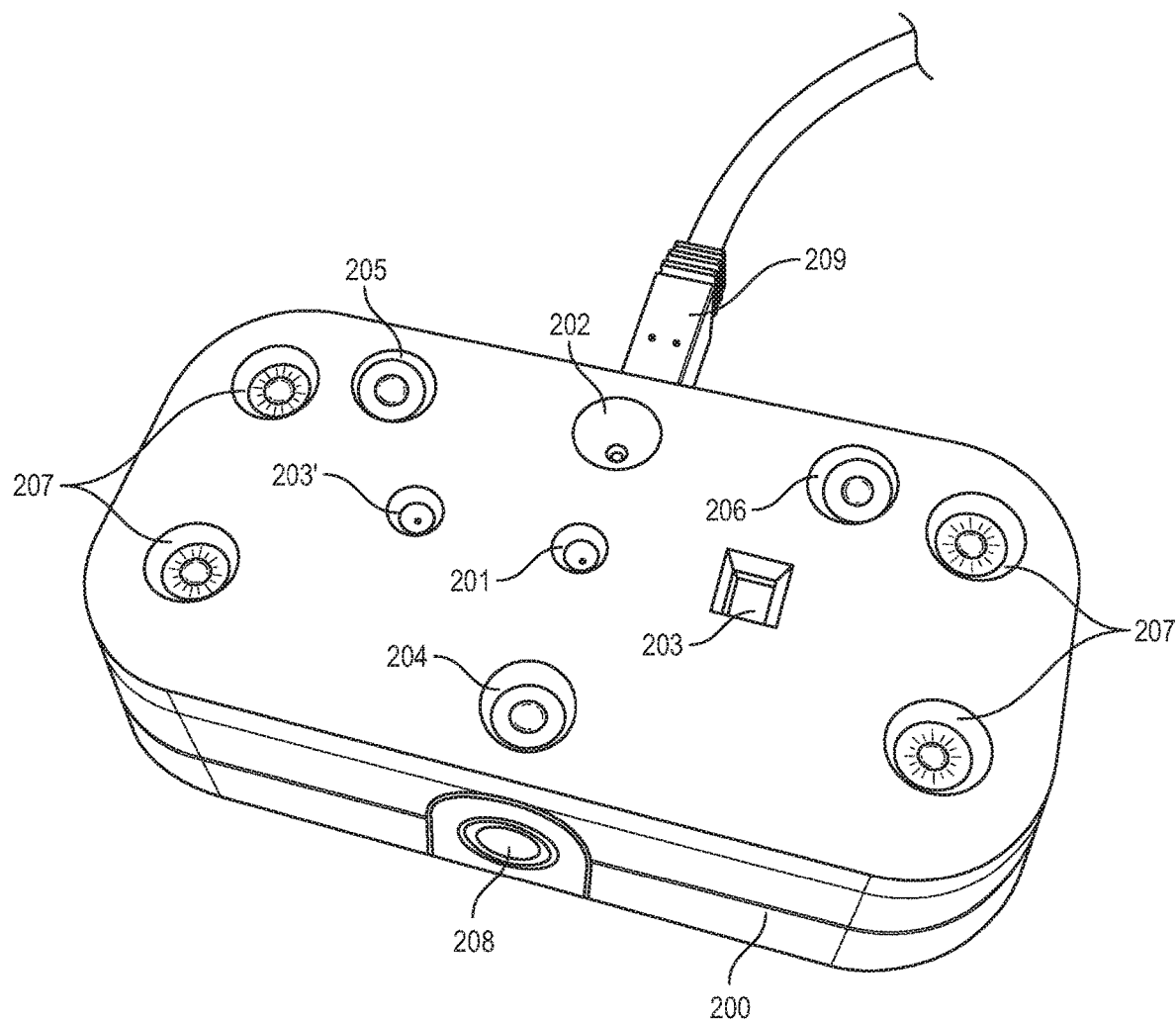
FIG. 17 shows a capture device according to one embodiment.
Figure 18:
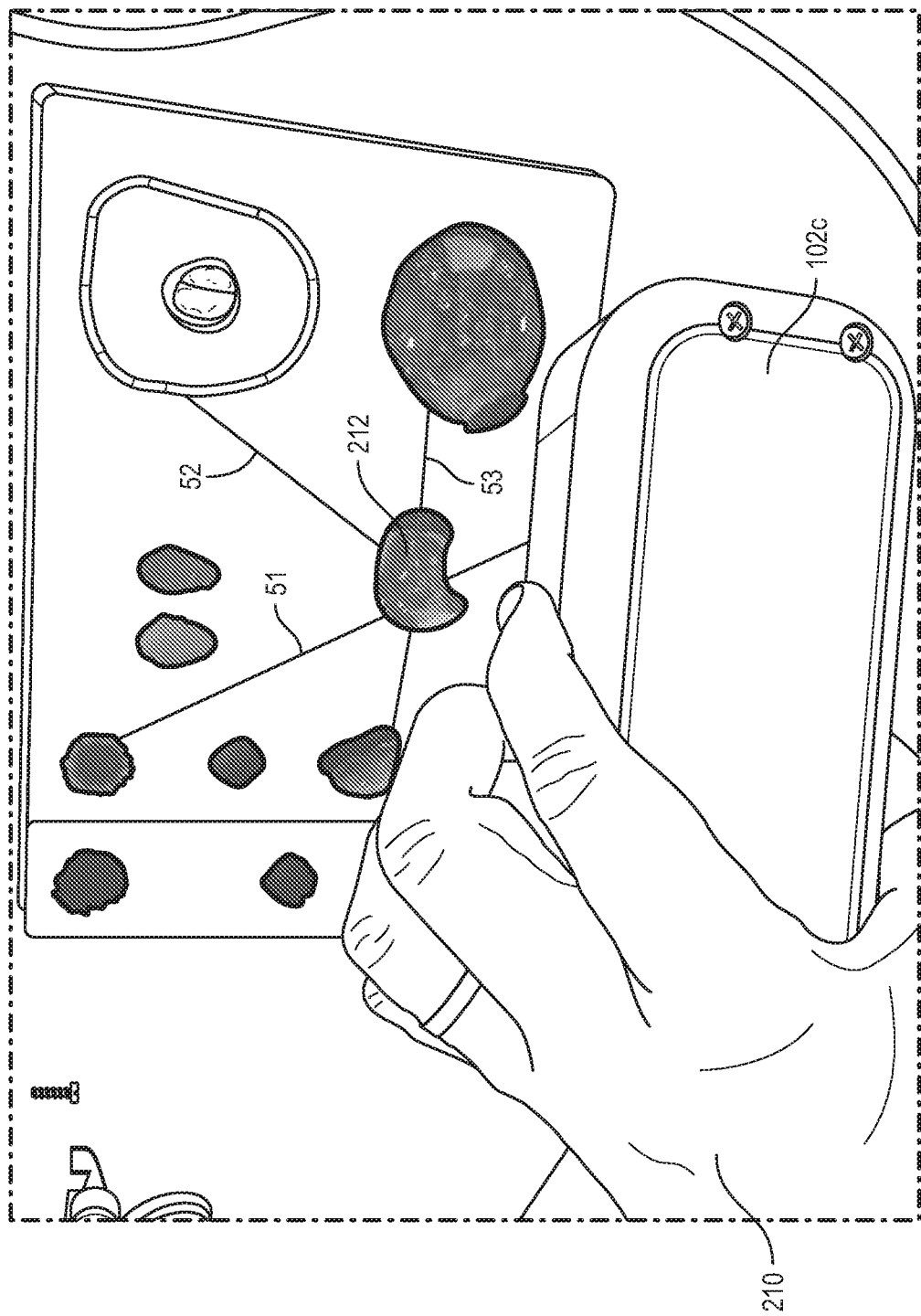
FIG. 18 is a further view of the device of FIG. 17.

FIGS. 17 and 18 show a further embodiment of capture device 102c. The device 102c includes a housing 200. Mounted in the housing 200 are: a texture or RGB camera 201, a thermal camera 202, a 3D camera 203, 203', a guide arrangement formed by three laser units 204, 205, 206, and a number of white light sources 207 (e.g. white light LEDs). An actuation button 208 and a port for connection of wired connector 209 may also be provided. Any other capture devices or functionality, communications functionality etc. described herein may also be included in this embodiment of capture device.

FIG. 18 shows the device 102c held by a user's hand 210, with the user's finger positioned on the actuation button 208. The device is pointed at an artificial "wound model" 212. The guide laser fan beam lines 51, 52, 53, emitted by laser units 204, 205, 206, guide the user to position the device at a desired capture range from the wound 212, and to align the device correctly with the wound 212.

In this device the 3D camera happens, in this embodiment, to be based on a fully sampled structured light method. The structured light uses infrared wavelengths to flood the scene to create a fully sampled depth map. If visible light were used it could be visually distracting and/or obscure any pattern projected from a visible light, graphic overlay, projector. The IR light is spatially or temporally encoded as discussed above. The structured light for the depth camera is projected from the aperture 203, while the sensor is at aperture 203'. Other 3D cameras, as discussed above, may be used.

FIGS. 19 to 26 show a display 219, which may be a screen, head mounted display or other suitable display separate to the capture device. In some embodiments similar data may be displayed on a display included in the capture device. A virtual reality (stereo) display may be used. The stereo display may be advantageously used to visualize the 3D rendered surface 223. In general any slices, projections, etc. from the captured data may be displayed. A reduced set of data may be displayed in some applications.

Figure 19:
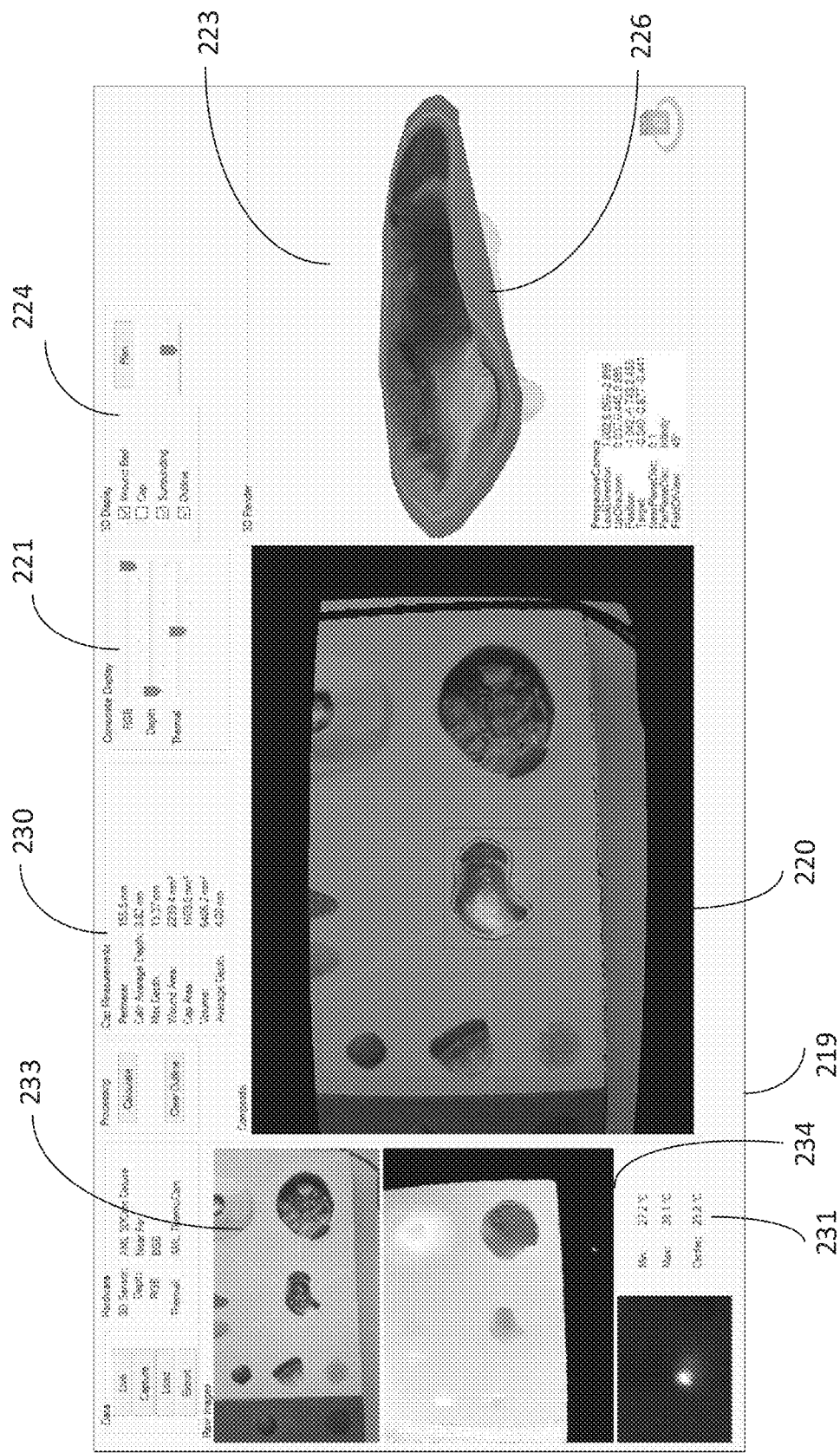
FIG. 19 shows a display displaying captured data.

As shown in FIG. 19, one or more of the following may be displayed.

Figure 25:
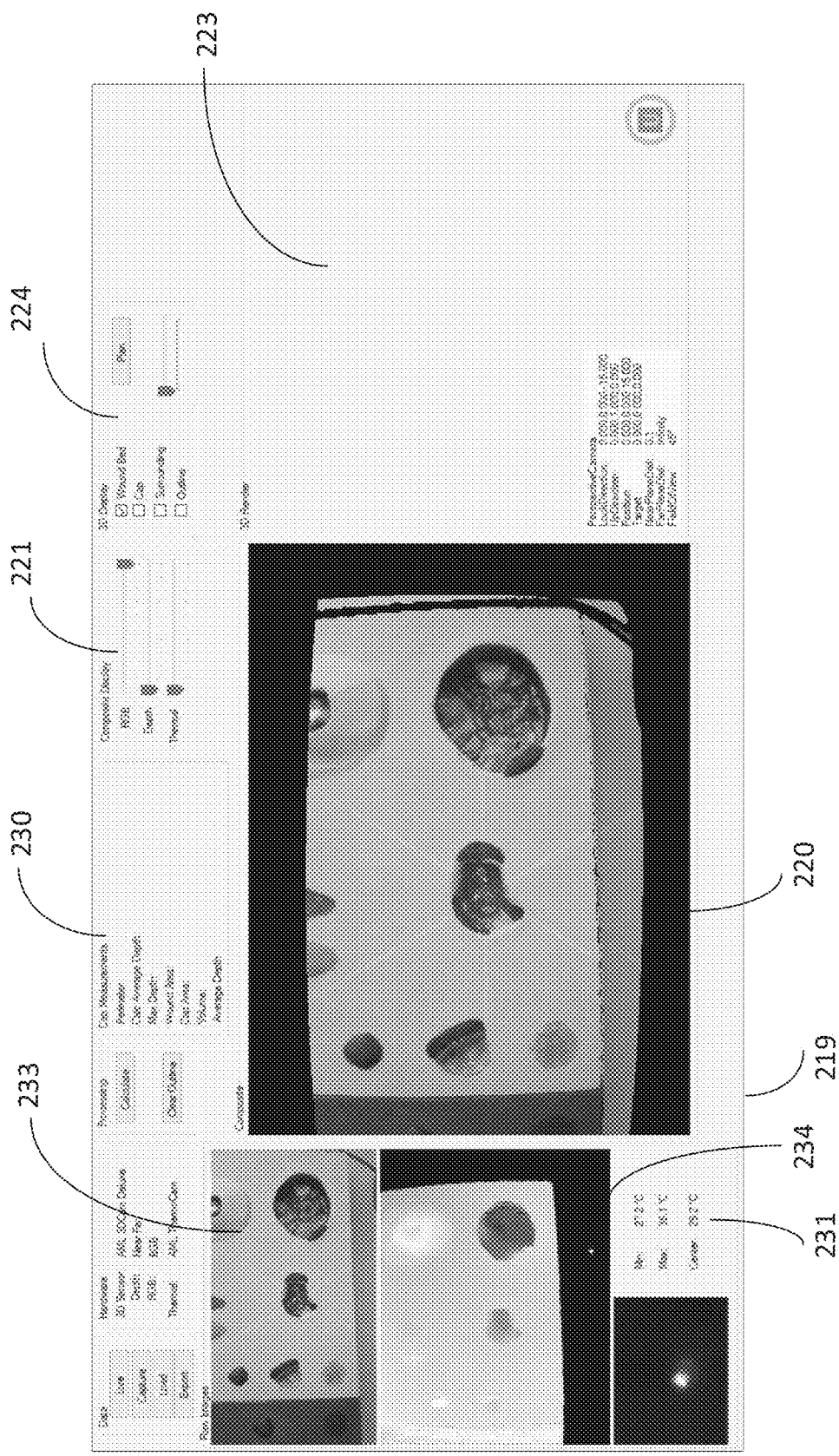
FIG. 25 is a further view of the display of FIG. 19.
Figure 26:
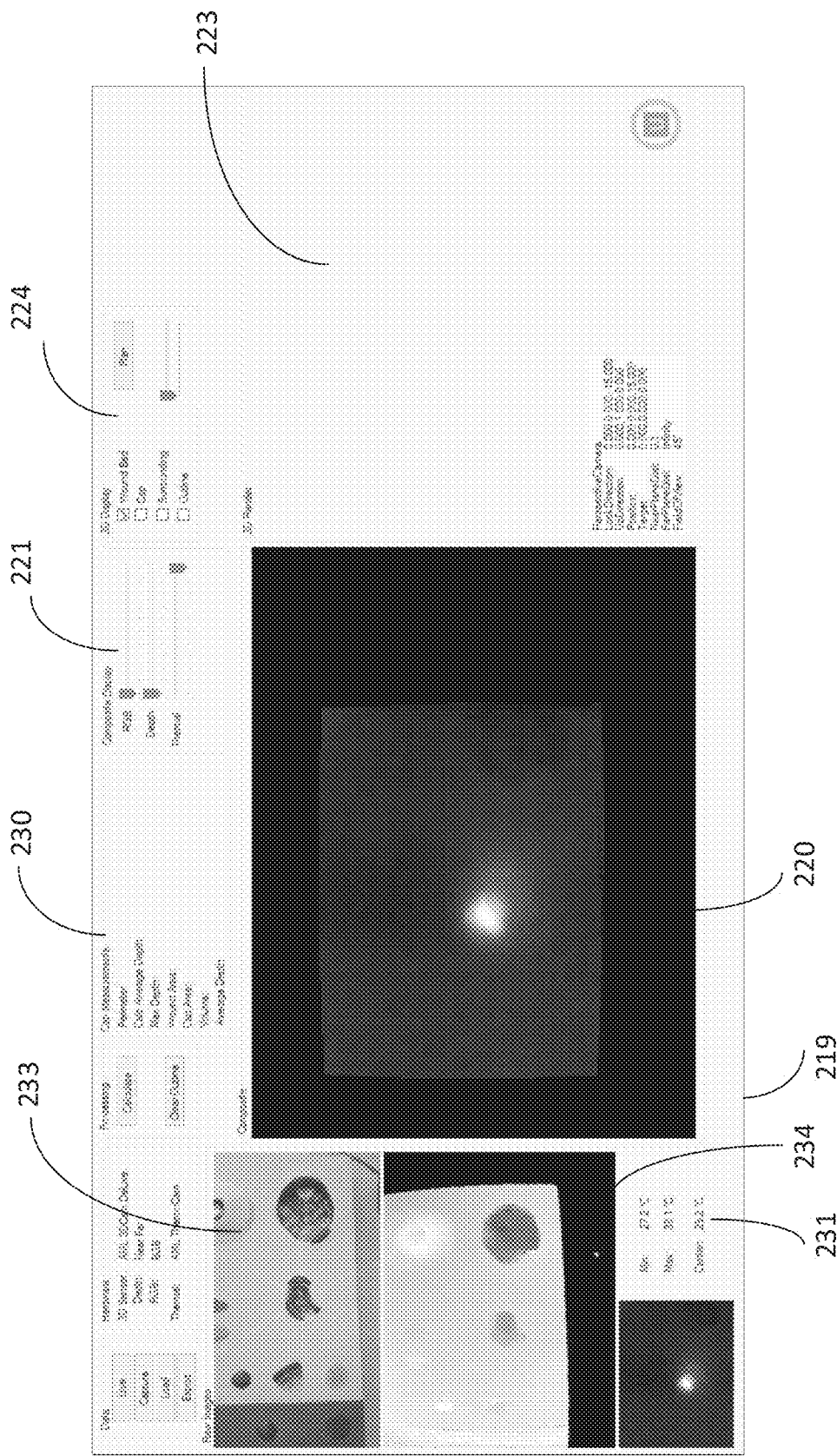
FIG. 26 is a further view of the display of FIG. 19.

A composite image 220 in which any captured image data may be overlaid to build up the displayed representation. In the embodiment shown, the captured image data included texture or RGB image data, 3D or depth image data and thermal image data. The weighting applied to each of these sets of image data may be adjusted using sliders in a control box 221. For example, FIG. 19 shows a composite image in which RGB and thermal image data are overlaid. FIG. 25 shows a composite image in which only RGB data is displayed. FIG. 26 shows a composite image in which only thermal data is displayed revealing a hot spot created artificially on the surface of the wound model.

Figure 20:
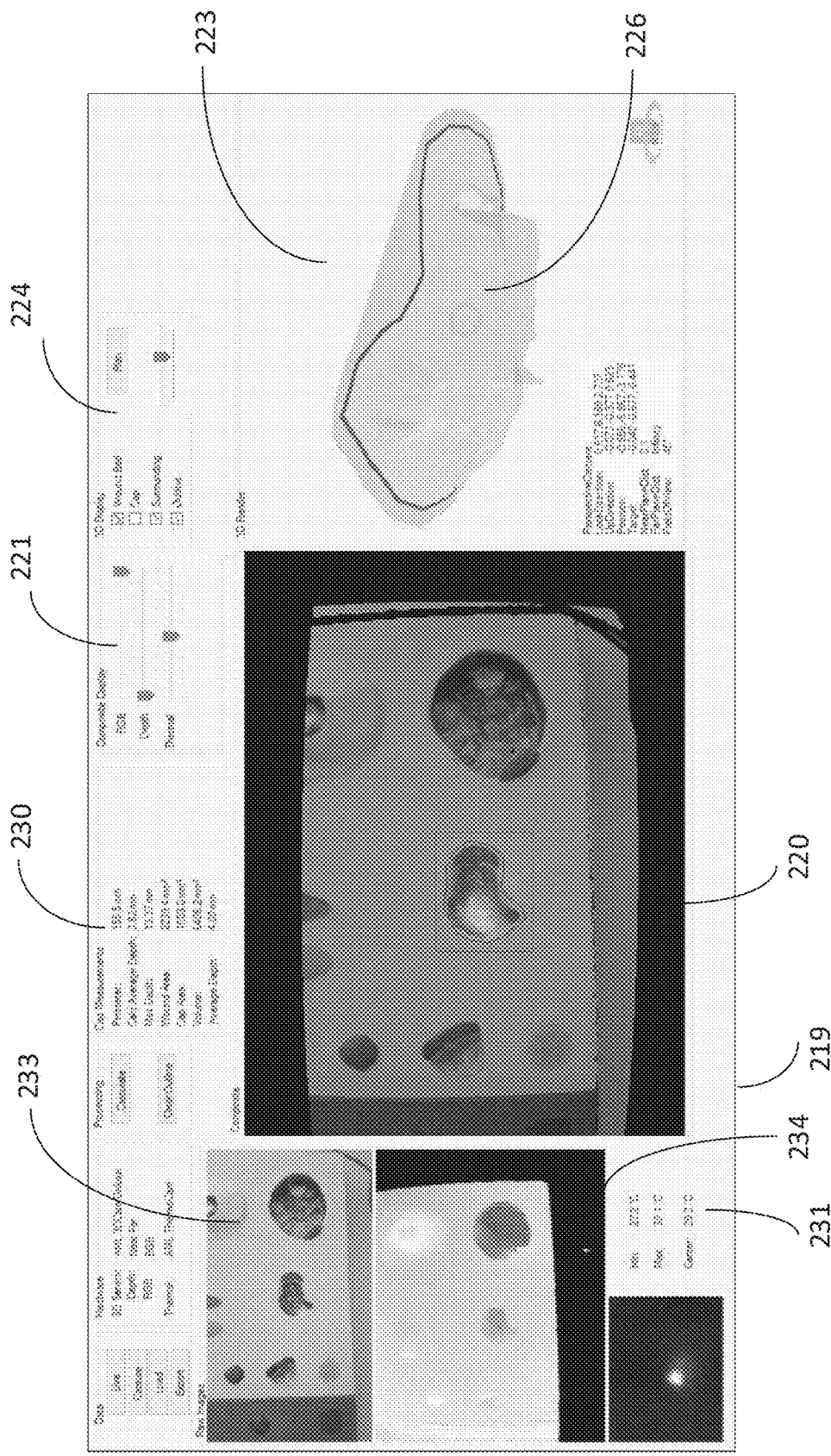
FIG. 20 is a further view of the display of FIG. 19.
Figure 21:
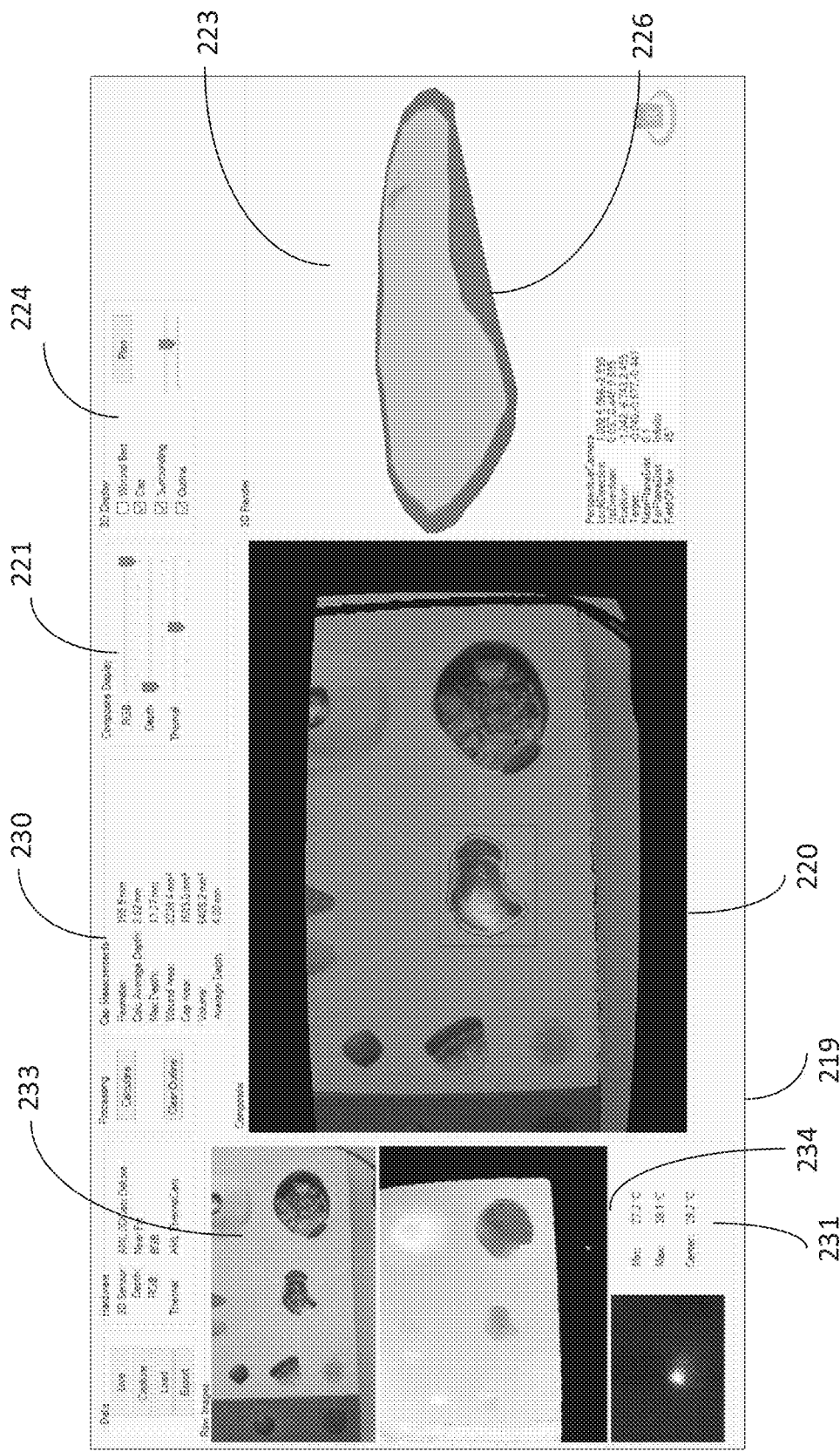
FIG. 21 is a further view of the display of FIG. 19.
Figure 22:
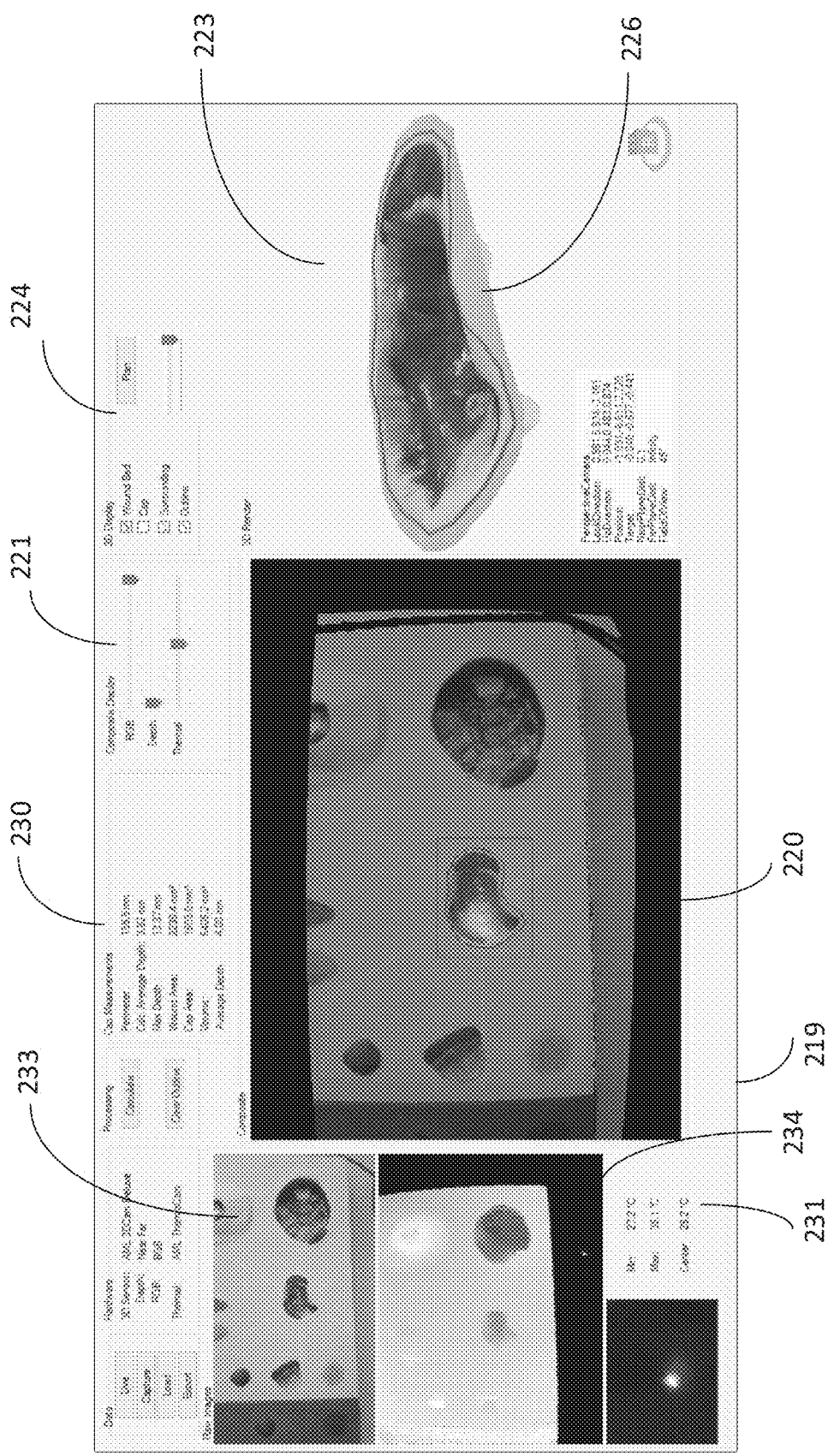
FIG. 22 is a further view of the display of FIG. 19.
Figure 23:
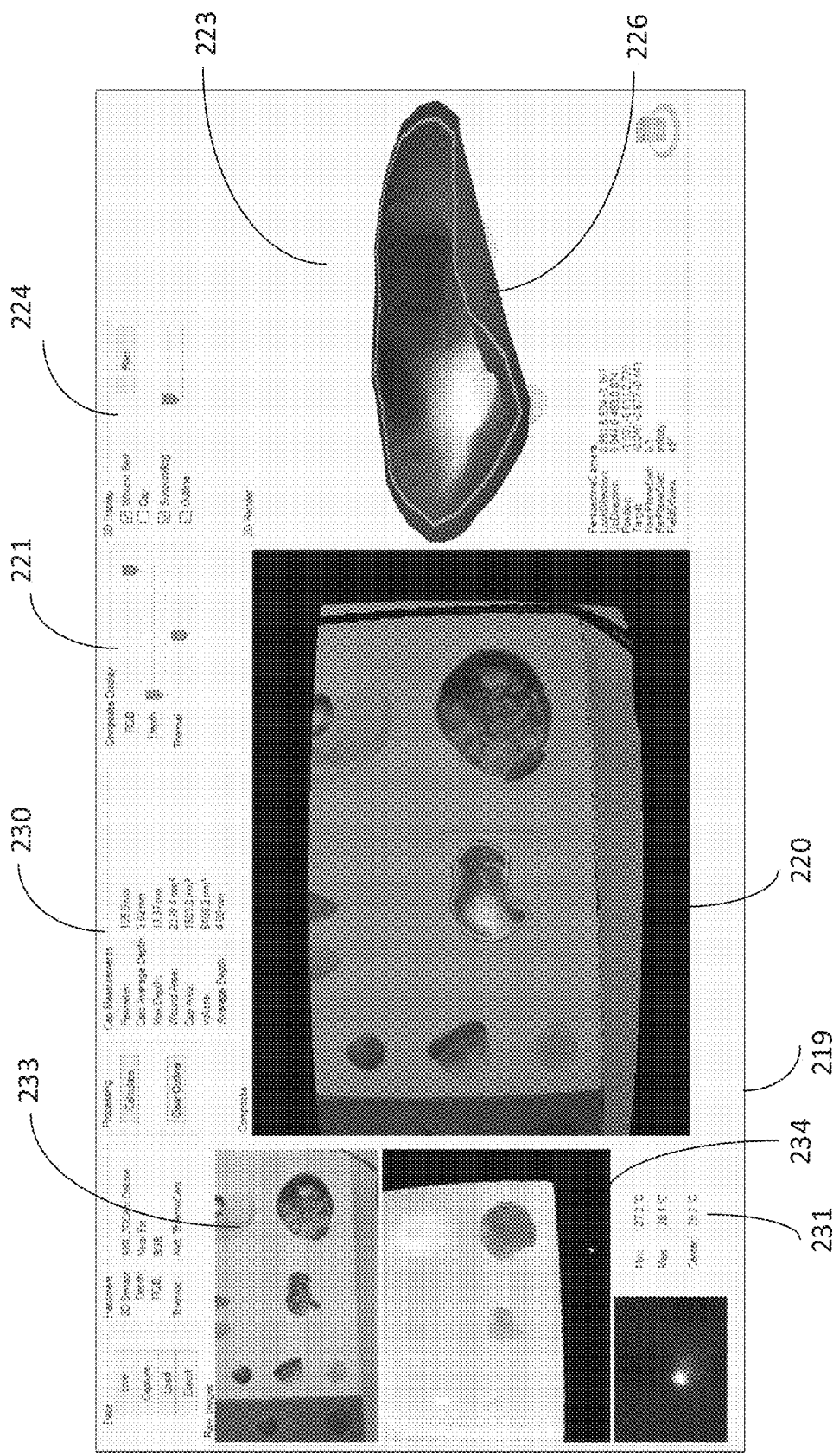
FIG. 23 is a further view of the display of FIG. 19.
Figure 24:
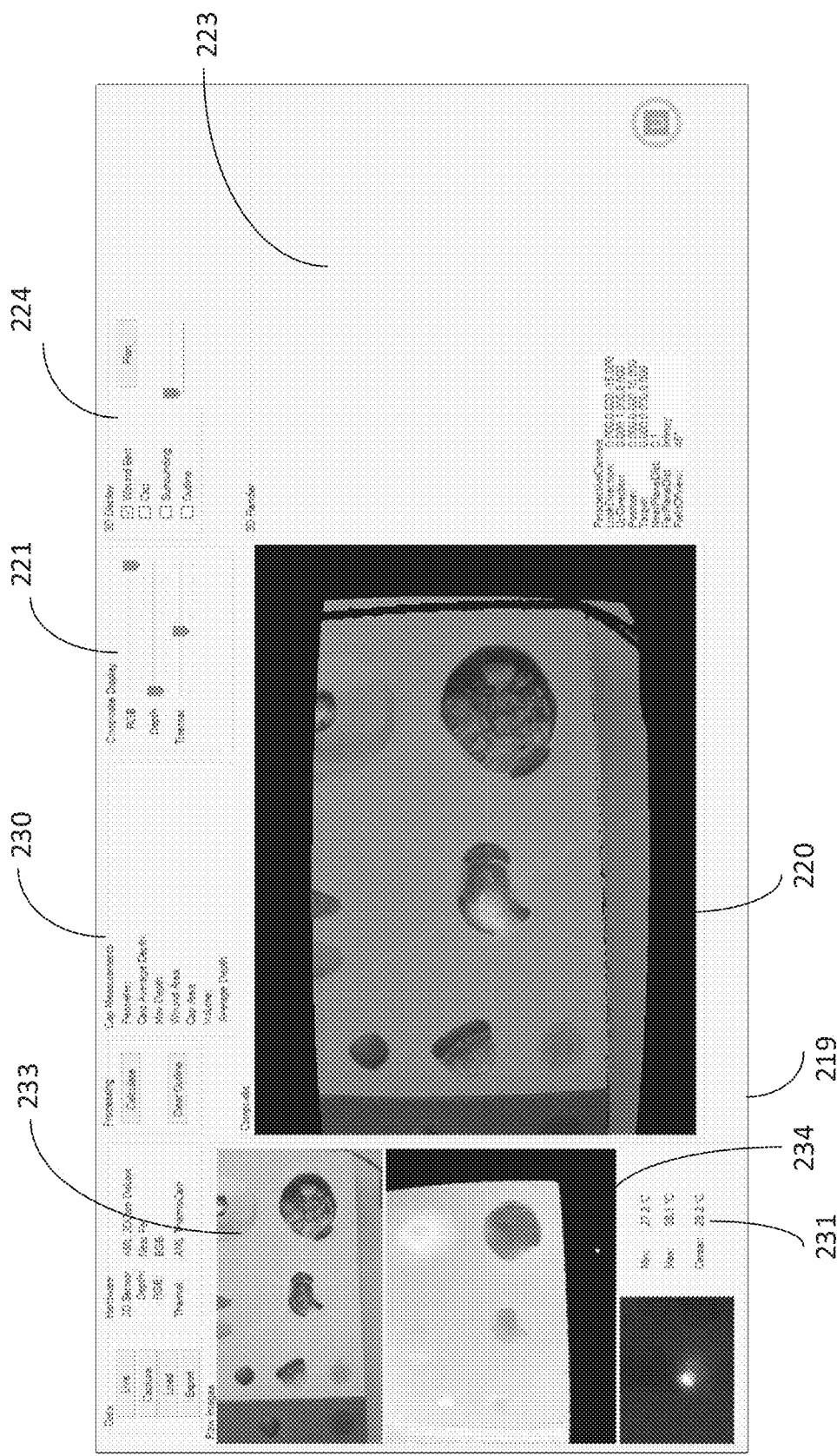
FIG. 24 is a further view of the display of FIG. 19.

A 3D representation 223 may be displayed, based on the 3D image data. The 3D representation may also be overlaid with any other image data, such as RGB and/or thermal data, or any other suitable indicators of wound parameters or characteristics may be overlaid on the 3D representation 223. A user may use checkboxes and sliders in control box 224 to alter the content of the 3D representation 223. For example, a user may select "wound bed" in order that the bed of the wound be displayed as in FIG. 19. In contrast a user may select "cap" in order that a cap over the wound be displayed, as shown in FIG. 21. The cap may be a surface extending within the wound boundary and may be determined by any suitable fit. For example the cap may simply be a plane fitted to points on the wound boundary. Alternatively, a cap may be determined based on an interpolation from the healthy skin surface—i.e the cap may represent the healthy skin surface that would exist were there no wound. The cap may be used as the reference surface for depth and volume measurements. The display of surrounding skin may be controlled using the "surrounding" checkbox and slider in control box 224. The user may also select an "outline", in which a wound outline 226 may be displayed. The wound outline may be determined by any suitable method, including any method disclosed in Applicant's U.S. Pat. No. 8,755,053, filed May 11, 2009; U.S. Pat. No. 9,179,844, filed Nov. 27, 2012; U.S. patent application Ser. No. 15/144,722; and U.S. Provisional Patent Application No. 62/423,709 filed 17 Nov. 2016. A user may rotate the 3D representation to examine the wound from different angles. To illustrate this, FIG. 20 shows an example in which the wound has been rotated to view it from the underside. Rotation allows viewing into any undermined regions that may have been captured in the data set (i.e. regions that extend under the skin surface outside of the wound boundary). Further controls may allow sub-surface slices or projections to be viewed, to allow these undermined regions to be displayed more fully.

Wound measurements may be displayed at display box 230. Displayed measurements may include one or more of: perimeter (based on the determined wound boundary); average depth; maximum depth; wound bed area (i.e. a surface area of the wound bed); cap area; wound volume.

The thermal image and associated temperature data may be displayed at box 231, including one or more of: minimum temperature, maximum temperature, average temperature, temperature at wound center. In some embodiments a temperature profile across the wound may be displayed.

A texture image may be displayed in window 233. A depth image may be displayed in window 234.

Figure 27:
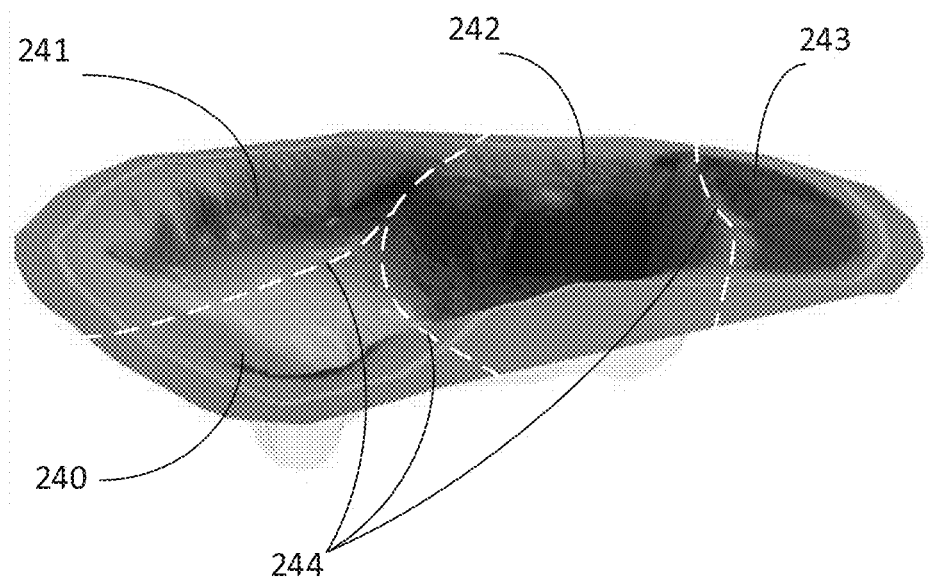
FIG. 27 illustrates segmentation of a wound.

FIG. 27 shows how the wound bed may be divided into a number of sub-regions 240, 241, 242, 243 for analysis of tissue types. The boundaries 244 within the wound boundary may be defined manually by a user, for example by tracing on a touch screen or other user input device. The user may define the sub-region boundaries based on a visual inspection of any of the available data, including RGB data, thermal data, fluorescence data and three dimension image data. Alternatively, the boundaries 240 may be determined automatically by a processor based on the available image data. The boundaries may be based on changes in color, temperature, fluorescence or surface roughness, for example.

For each sub-region, a determination may be made as to the tissue types present in that sub-region. Tissue types may include, for example: Granulation tissue, Slough, Eschar, Bone, Ligament, Healthy tissue (e.g. islands or tissue outside of wound). Tissue types may be selected manually by a user, for example from a menu of available tissue types. Alternatively, tissue types present in a sub-region may be determined automatically by analysis of the image and other captured data (including any of 3D, thermal, fluorescence data etc.). Previously gathered data for specific sub-regions may be overlaid or otherwise compared with current data, to allow changes or trends for that sub-region to be seen.

A determination may also be made as to the proportions of tissue types present in that sub-region. For example, by visual inspection a user may determine that granulation tissue occupies around 40% of a sub-region, slough around 30% and healthy tissue around 30%. The user may enter these values via any suitable user interface, for example, via sliders, text boxes etc. Alternatively, proportions of tissue types present in a sub-region may be determined automatically by analysis of the image data.

The wound bed area within each sub-region may be determined by analysis of the three-dimensional data. The proportions of tissue types can therefore be aggregated to provide one or more of: an aggregated surface area occupied by each tissue type; and an aggregated proportion of the wound bed area occupied by each tissue type.

The tissue types may also be aggregated into tissue classes, to provide one or more of: an aggregated surface area occupied by each tissue class; and an aggregated proportion of the surface area of the feature occupied by each tissue class. The tissue classes may include a viable tissue class and a non-viable tissue class.

Trends in tissue type area or proportions, or tissue class area or proportions, may be monitored over time. Tissue type area or proportions, or tissue class area or proportions, may be displayed in any suitable form, for example numerical form, color coded wound images, pie charts, bar charts etc. The overall size of a pie chart may be indicative of the size of the wound. An indication of wound "complexity" may be determined and displayed based on the identified tissue types and their proportions. Trends in wound complexity may also be monitored over time.

Alternatively, or in addition, the tissue classifications may be projected onto a plane or the cap to emulate, for consistency, the results in prior art devices that do not capture 3D data. The true surface areas may be understated in this display method however, particularly in regions that are steeply sloped. The full 3D methods discussed above may in general be more accurate.

In some embodiments auxiliary modules or devices may be used. These may attach physically to any of the capture devices described above, including to suitable Smartphones, tablets, computers etc. The attachment may be formed in any suitable manner, including for example a partial sleeve that allows the auxiliary device to mount to different capture devices. Alternatively, auxiliary devices may be integrated into Smartphone cases.

Suitable auxiliary devices include structured light devices (projecting one or more spots, stripes, fan beams etc. produced by appropriate laser devices or a pattern generator), guide devices (e.g. projecting a laser or other light pattern to guide the user to position the device at a desired range and/or position and/or orientation with respect to the skin surface) cameras, stereoscopic cameras, and image splitters. Further auxiliary devices include sonar, ultrasound, infrared, radar (including miniature radar, radio-frequency radar), or time of flight range finder modules. An auxiliary device may include one or more further sensors (e.g. light sensors, reflectance sensors, temperature sensors), light sources, distance sensors, further cameras, or code readers (e.g. RFID readers, barcode scanners etc.) etc.

An auxiliary device may be battery powered, or may be powered from an external power source. Where the auxiliary device requires power from an external source, in some cases this may be provided by a wired connection to the device's powered headphone jack. Further, control signals can be sent over a wired connection between the device's headphone jack and the auxiliary device, using the device's standard interface for transmitting audio signals through that jack. In other embodiments a wired connection may be made to any other suitable jack or connector on the capture device (e.g. Lightning connector).

Alternatively, control signals may be sent over any other suitable wired or wireless connection, including e.g. Bluetooth.

Where a structured light auxiliary device is used, this may be a very simple device providing range or scale information. That is, the structured light information may be used merely to determine a scale. A full model of the surface, as provided by more complex structured light devices may not be required in some applications.

In still further embodiments, a known size user-supplied fiducial may be used. By placing this fiducial in any image, the scale can be determined. This fiducial may be any small known object. For example, a circle or a triangle van be used to determine scale and orientation information. As noted above, user-supplied fiducials may include encoded information, which may be read by the capture device or any other suitable reader.

Further embodiments, operating within the facility, in which a user is guided to position the device at a desired range or position (including lateral position) for data capture will now be described. In these embodiments a guide is projected onto the surface, and the user moves the device to achieve a desired alignment of the guide with the surface and with the patient's anatomy. The Applicant's U.S. Pat. No. 9,179,844, the entire contents of which are incorporated by reference herein, discloses a projected guide consisting of a number of laser lines, and such an arrangement may be used in devices disclosed herein. For example, an auxiliary unit including laser fan beam generators may be attached to a Smartphone or other device.

However, in some embodiments of the current application, the projected guide is used solely as a positioning aid which assists the user to position the device at a desired range, thereby setting a scale associated with the resulting image. In these embodiments the structured light is either not present in captured data (e.g. it may be switched off for data capture) or is not analysed to provide scale information.

In other embodiments a guide based on an earlier captured image may be projected onto the surface. In a similar manner to other embodiments in which a guide is overlaid on a device display, the projected guide may guide the user to position the device at a desired range and/or perspective. The projected guide may guide the user to position the device at the same range from the user's skin, and/or with a similar perspective to that of a previously captured image. This will result in the scale of the second image being approximately the same as the scale of the previous image. The images may be directly compared and dimensions may be read directly from the second image, provided the cameras used for each data capture are the same or have similar characteristics. Alternatively, captured data may include camera parameters, which can subsequently be used in scaling to a common or normalized scale. Scaling or registration, as described above, may be performed if greater accuracy is desired.

The projected guide may simply be an image of the skin surface captured previously. A user may align the device with the desired position and/or range by moving it to bring the projected guide into alignment with the patient's anatomy. Correct alignment of the device may be determined by the user, simply by observing the alignment of the guide and the patient's anatomy. Alternatively, the device may detect the alignment of anatomy (as viewed through the camera) and guide and when an acceptable level of alignment is reached provide feedback in the form of an audio, visual or audiovisual notification. For example, when acceptable alignment is achieved the device may beep. Alternatively, a visual indicator may be displayed when acceptable alignment is achieved. In some embodiments the device may automatically capture data when an acceptable alignment is detected. In other embodiments the user may issue a data capture instruction (for example by pressing a button, touch screen etc., or by any other suitable user input).

In other embodiments, the projected guide may be one or more portions of a previously captured image of the patient's skin surface. For example, it may be desirable to remove the wound 1 from the projected guide image, since the shape of the wound 1 may change over time, so that using the wound 1 in the guide image may confuse the user. Alternatively, the guide may comprise one or more guide masks or markings based on a previously captured image of the patient's skin surface. For example, guide markings may be generated based on the position of skin features 3, or the outline of a user's limb, or positions of bone features etc. In still further embodiments, one or more guide masks or markings may be selected from a library of available guide masks or markings (e.g. a lower leg mask may be used, having a shape corresponding to the average lower leg).

The projected guide may include image portions or markings corresponding to the anatomical fiducials 3. Anatomical fiducials may be selected by a user in the previous image for subsequent use in the guide image. In methods using projected guides, the absolute scale is again not necessarily known. The image data is obtained at approximately the same scale in each case because the user is guided to position the device to deliver images with approximately the same scale. If further accuracy is required, scaling or registration can be performed as discussed above.

The projected guide may be projected using any suitable auxiliary projector. Portable devices incorporating picoprojectors or any other suitable type of projector may also be used. In other embodiments the guide may be projected using the device's inbuilt flashlight. A suitable pattern mask may be added to the window of the flashlight in order to project a guide pattern.

Graphical overlays, conveying additional information such as the patient ID, wound type and location, and so on, may be added to any kind of projected guide pattern. Further guide markings may indicate the extent of the image frame or camera field of view.

In still further embodiments the device may be positioned at a desired range from the surface using a physical guide or frame that sets a distance between the surface and device. Such a physical guide may include a device support, and a spacing arrangement with one or more distal elements configured to contact the skin. In many embodiments skin contact is undesirable. However, in some settings the use of such a physical guide may be acceptable.

Where the device is capable of determining a range to the skin surface, by any of the methods disclosed herein or any other suitable method, this range information may be used in at least the following ways.

First, the range information allows data to be captured at an arbitrary range and the appropriate scale factor to be determined and applied to the measurements. Additionally, the range information may be used to crop and/or rescale photos captured at arbitrary ranges (on the same model smart device) or with different model smart devices to a standard field of view. This should lead to greater consistency in the display of images captured as part of a serial study.

Second, the range information may be used to guide the user to capture at a pre-determined, 'standard', range. Again this leads to improved consistency (provided all captures are made using the same model smart device). A variation would be to guide the user to capture at the range which results in a standard field of view regardless of the camera model in the smart device, again for improved consistency.

In any embodiment described herein, the user device may be connected over any suitable wired or wireless connection to another local device and/or over a network to a server. The server may be a facility server (e.g. a hospital server) or may be a remote server used by a number of different facilities.

In some embodiments the capture and storage of data is controlled such that data is not stored, or is stored only transiently, on the device itself. Data is immediately communicated to secure storage over the wired/wireless link and/or over the network. A user may view data retrieved from that secure storage on the device display. The Applicant's methods at the device level may be implemented using a web application. The device may operate as a thin client.

In general, any of the data storage, communication and management methods and systems disclosed in the Applicant's co-pending U.S. patent application Ser. No. 15/144,722 (the entire contents of which are hereby incorporated by reference) may be employed.

Further, any desired associated data may be captured, such as e.g. an audio/video recording of caregiver's observations, images of the patient, the wound outline(s), patient ID, condition, location data (e.g. GPS data) etc. Such data, and any data from auxiliary sensors, may be tagged to or associated with captured image data.

While automated methods of wound measurement may be provided, in some embodiments the user may be enabled to enter manually obtained measurements of wound dimensions (e.g. length, width).

Any of the assessment techniques described herein allow surface feature dimensions to be tracked over time, whether in arbitrary units or in absolute dimensions. These trends allow medical professionals to monitor surface feature development or healing. Where a measurement departs from the predicted trend (e.g. an average trend for similar wounds, or some other defined trend based on one or more of: wound size and/or other characteristics, tissue type, patient characteristics etc.), an alert may be issued to a user, either through the device itself or by any suitable messaging system to a healthcare provider.

Statistical trends of conditions, treatments and outcomes across multiple patients can be monitored. These data can be used to suggest a particular treatment, based on a set of symptoms exhibited by a particular patient. Data can provide predictions for wound healing. Where actual healing differs from the prediction by more than a threshold, the system may issue an alert. Similarly, where the actual healing is in accordance with the predicted trend, a positive notification (e.g. "Wound healing well", or a green light or another positive indicator) may be issued or displayed.

In some embodiments it may be desirable to have substantially consistent scene field-of-view between image captures, despite the images being captured at different times and/or using different devices. This allows a series of images to have consistent apparent scale, allowing consistent visual scale appearance. To achieve this consistent scene size the image may be captured at a defined range (and/or zoom factor for devices incorporating a zoom lens), determined via the camera angular field-of-view. This can be achieved by several of the methods disclosed herein, including guiding the user with an image or guide overlay, guiding the user with a projected guide, and/or guiding the user to move the device closer or further to the surface until a desired range is achieved.

In any of the embodiments described herein it may be assumed that the surface feature and surrounding skin all lie in a plane. For many applications, this is expected to be sufficiently accurate. It may also be assumed that the device's optical axis or optical axes is/are perpendicular to that plane. Alternatively, in some embodiments no such assumption is made, and appropriate corrections may or may not be made.

The Applicant's methods and devices allow for assessment of skin features, especially skin features of human patients. The methods may rely on ubiquitous consumer electronics devices, such as smartphones or tablets, allowing assessment data to be obtained conveniently using relatively cheap and readily available devices. Data can be captured in an intuitive manner.

In some embodiments, executed within the facility, an auxiliary device or module (or "widget") including additional hardware may be used. In the case of auxiliary devices containing optical elements the alignment of the widget to the onboard camera within the capture device may be important. If the exact alignment of the auxiliary device to the host optical system cannot be guaranteed by design, it may be estimated or calibrated. The auxiliary device may communicate with the capture device using any appropriate wired, physical or wireless link.

The physical attachment of an auxiliary device to the capture device may be difficult due to the lack of mounting points available. However, an auxiliary device may be 'clipped on' to the capture device or built into a replacement case, or cover. The alignment of the auxiliary device to the capture device's optical system may be difficult to reproduce exactly between installations (especially where the auxiliary device is used with, or designed for use with, a multitude of device types). In such cases automatic alignment detection may be advantageous.

In one embodiment an auxiliary device may include a camera. In another embodiment an auxiliary device may include a camera and a range-finding device. This range finding device may be a direct range finder (ultrasonic, optical time-of-flight, microwave radar, etc.), or a structured light or triangulation based device using one or more laser points or lines etc.

An auxiliary device including a camera may have a field-of-view overlapping that of the camera in the capture device. By imaging a scene with both the camera in the capture device and the auxiliary device simultaneously or in quick succession, the relative geometry of the cameras can be determined by comparing the two frames in conjunction with the intrinsic parameters of each camera and the position of common points in the scene. This provides improved accuracy over an auxiliary device including no camera, since it allows the geometry between the auxiliary device and the capture device to be determined.

The position of the points in common is given by the auxiliary range-finder subsystem and the cameras' intrinsic parameters. The extrinsic parameters of the two cameras can be determined by determining the alignment of the two camera frames.

Here, 'intrinsic' parameters refer to the known internal geometry of the camera, eg: lens focal length, lens focal distance, sensor pitch, geometric distortion, etc. In general the degrees per pixel (or the solid angle subtended by a pixel) will be known. However, because the range is unknown, the size of an area on an image object corresponding to a pixel on the sensor is not known.

'Extrinsic' parameters refer to the geometrical relationship between two components, for example the angle and offset of the laser plane relative to the camera's optical axis. The extrinsic parameters of the components within the auxiliary device can be determined to the required degree of accuracy either by design or by a calibration step in the factory prior to being supplied to the user of the smart device.

The camera within the auxiliary device may not be high resolution assuming there is sufficient scene overlap with the capture device camera. This allows on-the-fly calibration of the geometry between the auxiliary device and the capture device (ie: extrinsic parameters) by using an inexpensive low-res camera in the auxiliary device. The capture device's high resolution camera may be used for determining the 3D model and/or measurements as well as for producing the texture image.

In one embodiment an auxiliary device may include three line generating lasers surrounding a low-resolution camera connected to a low-power processor and battery subsystem. The auxiliary device may project a light pattern similar to that disclosed in the Applicant's U.S. Pat. No. 9,179,844.

Communications with the capture device may be provided by Bluetooth, or other wireless, or wired communication link.

Figure 28:
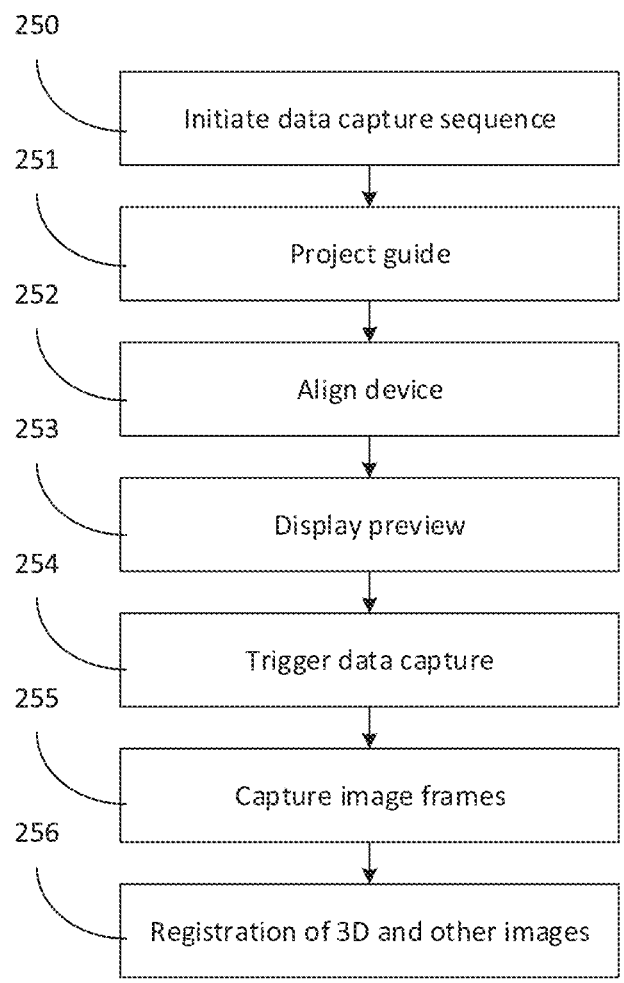
FIG. 28 is a flow chart showing one data capture sequence.

In one embodiment, executing within the facility, data may be captured in the following sequence, described with reference to FIG. 28. In other embodiments other capture sequences may be used, and the capture sequence may be adapted to the type of capture device and/or auxiliary device used. Capture from the 3D camera and other cameras may be simultaneous or sequential. Simultaneous capture may be appropriate when the spectra do not overlap, eg; capture from an IR 3D camera and a visible RGB camera. Simultaneous capture may be preferred since it avoids the need for registration when there is motion of the device. Sequential capture may however be needed in some cases, for example in the case of capture of a texture image and a fluorescence image.

At block 250 a user initiates the data capture sequence. At block 251 the guide may be projected. At block 252 the user aligns the capture device with the scene using the projected guide (e.g. bringing the capture device to a desired range and/or position and/or orientation). At block 253 a preview may be shown on the capture device's display (if the device includes a display), using image data from the capture device's texture camera. At block 254 a user may trigger capture, for example by pressing a button or touch screen on the capture device, or by any other suitable mechanism for issuing a capture instruction.

At block 255 one or more image frames may be captured. For example, using the capture device 3D camera 3D image data may be captured with the guide switched off. Using the thermal camera, thermal image data may be captured. Using a texture camera and switching the UV source on and off as necessary, fluorescence image data may be captured.

At block 256, a registration between the 3D data, thermal data and fluorescence data may be performed, as discussed above.

The Applicant's capture device may provide patient identification or selection functionality. A patient may be identified or selected by scanning a code associated with the patient, for example on a hospital wristband. The code may be a barcode, QR code, RFID code or any other suitable code. Alternatively, a patient may be identified or selected by scanning biometric information, such as a fingerprint, iris, or retina. Alternatively, a patient may be identified or selected by facial recognition. Where the device includes a 3D camera, facial recognition may be based on three-dimensional image data. Alternatively, a patient may be identified or selected by voice recognition. Similarly, a user, carer or healthcare provider may also be identified or selected by any of these methods. User, carer or healthcare provider identification or selection may form the basis of decisions as to which functions are provided or permitted. For example, some users may be permitted to obtain only partial data sets, or use only certain functions of the device. Some users may be permitted to edit data.

The device may also be arranged to cross-check the patient identification by analysis of captured data. For example, a determination may be made by comparison of data sets that e.g. the wound dimensions or shape, or the patient's skin tone or anatomical fiducials, or the apparent progress in wound development or healing, or any other feature of the data currently being captured are inconsistent with the selected or identified patient and their previously captured data.

Various measurement technologies are disclosed herein. Some measurements or detections may be based on only one type of measurement technology. However, others may be based on two or more measurement technologies. For example, some bacteria or biofilms may be apparent in both thermal and fluorescence images. Similarly, perfusion may be measurable in thermal images, RGB images (e.g. by analysing laser speckle), pulse oximeters and Doppler ultrasound.

Further sensors may be included in the capture device, or as auxiliary sensors for attachment to the capture device. Further sensors may include smell or odor sensors, pulse oximeters, pulse sensors, pH sensors. Other sensors may be provided in smart bandages, or in local sensors configured to be positioned near the wound under a conventional bandage. Such sensors may measure one or more of: pressure, temperature, pH, odor, color change, exudate volume, moisture and pulse sensors, sensors dedicated to specific chemicals, DNA, bacteria etc. Such external sensors or smart bandages may communicate with a capture device 102, 102a, 102b, 102c, or with any other part of the facility of FIG. 1. The sensors can also be used to analyse biological material accumulated onto the dressing. This communication may be over a suitable wireless link. Data may be captured periodically or continuously, and may be stored in storage local to the sensor. This provides further data in-between captures with a capture device 102, 102a, 102b, 102c.

Contrast agents and dyes may be added in some applications. These may assist in identifying tissue types, or particular bacteria, or in measurement of pH (where a pH-sensitive indicator dye is used). pH may be measured by detection of indicator dye colour in the texture image data.

In some embodiments the Applicant's methods may take advantage of existing device capabilities without the need for separate hardware attachments. In some embodiments the Applicant's methods may avoid any physical contact with the wound. In some embodiments the Applicant's methods may provide a mechanism for determining the scale of an image without requiring a reference object to be placed near the wound. In some embodiments the Applicant's methods may enable the determination of both area and depth or volume of a wound or dimensions of other anatomical surface features.

Where data from different devices (e.g. from one or more cameras and one or more sensors) or a plurality of sets of data from a single device (e.g. two or more images from a single camera) are required to be captured, all such data may be captured simultaneously or sequentially in response to a single capture instruction.

In some embodiments macro and/or wide angle images may be captured. Macro and/or wide angle images may be captured in addition to images at other ranges and/or focal lengths. One or more macro and/or wide angle images may be captured in addition to any number of images at other ranges and/or focal lengths, including any image or number of images according to any embodiment described above.

In some embodiments, a macro image may provide a more detailed view of a surface of an anatomical surface feature. For example, a macro image may provide a more detailed view and allow assessment of features or characteristics within a wound bed.

In some embodiments, a wide angle image may provide a broader view of a surface. For example, a wide angle image may provide a large field of view (encompassing an entire limb, or foot or torso, or even a whole body) to provide a context for where on the body the wound or wounds are.

Any of the guiding arrangements described above may be adapted to guide a user to position the device at a suitable range and/or position and/or orientation for capturing a macro image. In some embodiments the capture device may be arranged to guide the user to two or more desired ranges for capture of different images.

Thermal, 3D or other data gathered by the device may be used to automatically distinguish the patient from the background.

Any of the capture devices may be implemented as modular devices configurable through software and/or hardware plugins or modules to provide various levels of capability, performance and/or price.

EXAMPLES

Several aspects of the present technology are set forth in the following examples.

1. A method of assessing a feature on a patient's skin surface, including:
   i. receiving a three-dimensional data set representative of the patient's skin surface;
   ii. determining a boundary of the feature in the three-dimensional data set; and
   iii. determining with a processor a three-dimensional surface area of the feature within the boundary.

2. A method as described in example 1 including identifying a plurality of sub-regions within the boundary and identifying one or more tissue types in each sub-region.

3. A method as described in example 2 including a processor automatically identifying the plurality of sub-regions.

4. A method as described in example 3 wherein the processor automatically identifies the plurality of sub-regions by analysis of one or more of:
   a. three-dimensional image data;
   b. thermal image data;
   c. fluorescence image data; and
   d. texture image data.

5. A method as described in any one of examples 2-4 including a user manually identifying the plurality of sub-regions via a user interface.

6. A method as described in any one of examples 2-5 including a user manually identifying one or more of the plurality of sub-regions via a user interface and a processor automatically identifying one or more others of the plurality of sub-regions.

7. A method as described in any one of examples 2-6 including determining for each sub-region a proportion of a surface area of that sub-region occupied by each tissue type identified in that sub-region.

8. A method as described in any one of examples 2-7 including determining for each sub-region a proportion of a surface area of that sub-region occupied by each tissue type identified in that sub-region; determining a surface area of each sub-region; and aggregating the determined proportions of tissue types to determine one or more of: an aggregated surface area occupied by each tissue type; and an aggregated proportion of the surface area of the feature occupied by each tissue type.

9. A method as described in any one of examples 2-8 including determining for each sub-region a proportion of a surface area of that sub-region occupied by each tissue type identified in that sub-region; determining a surface area of each sub-region; aggregating the determined proportions of tissue types and aggregating the tissue types into tissue classes, to determine one or more of: an aggregated surface area occupied by each tissue class; and an aggregated proportion of the surface area of the feature occupied by each tissue class.

10. A method as described in example 9 wherein the tissue classes include a viable tissue class and a non-viable tissue class.

11. A method as described in any one of examples 1-10 wherein the feature is a wound and the surface area is a wound bed area.

12. A method as described in any one of examples 1-11 including capturing three-dimensional image data of the patient's skin surface and processing the captured image data to form the three-dimensional data set.

13. A method of assessing a feature on a patient's skin surface using a handheld capture device that includes a three-dimensional imaging system, including:
   capturing a first data set using the handheld capture device at a first device pose, and capturing a second data set using the handheld capture device at a second device pose, each of the first and second data sets including three-dimensional image data of the patient's skin surface captured by the three-dimensional imaging system; and
   processing at least the first and second data sets to form a three-dimensional model of the patient's skin surface including the feature.

14. A method as described in example 13 wherein:
   the handheld capture device includes a thermal camera;
   the first data set and the second data set each includes thermal image data; and
   processing at least the first and second data sets includes registering the thermal image data with the three-dimensional model.

15. A method as described in either example 13 or 14 wherein:
   the handheld capture device includes a texture camera;
   the first data set and the second data set each includes texture image data; and
   processing at least the first and second data sets includes registering the texture image data with the three-dimensional model.

16. A method as described in any one of examples 13-15 wherein:

the first data set and the second data set each includes fluorescence image data; and processing at least the first and second data sets includes registering the fluorescence image data with the three-dimensional model.

17. A method of displaying data representative of a feature on a patient's skin surface, including:

displaying a first representation of the feature based on first data captured at a first time; and displaying a second representation of the feature based on second data captured at a second time.

18. A method as described in example 17 including displaying an animation including at least the first and second representations.

19. A method as described in either example 17 or 18 including creating and displaying a third representation of the feature based at least in part on an interpolation or extrapolation from at least the first and second data.

20. A method as described in example 19 including displaying an animation including at least the first, second and third representations.

21. A method of displaying data representative of a feature on a patient's skin surface, including:

displaying a first representation relating to the feature based on first data captured at a first time;

displaying a second representation relating to the feature based on second data captured at a second time; and creating and displaying a third representation relating to the feature based at least in part on an interpolation or extrapolation from at least the first and second data.

22. A method as described in example 21 including displaying an animation including at least the first, second and third representations.

23. A method as described in either example 21 or 22 wherein the representation is an image.

24. A method as described in example 23 wherein the image includes a representation of a three-dimensional model including the feature.

25. A method as described in example 24 wherein the image further includes one or more of:

a. a representation of thermal image data overlaid on the representation of the three-dimensional model;

b. a representation of fluorescence image data overlaid on the representation of the three-dimensional model;

c. a representation of texture image data overlaid on the representation of the three-dimensional model; and d. one or more wound dimensions.

26. A method of displaying data representative of a feature on a patient's skin surface, including:

displaying a three-dimensional model of the skin surface including the feature; and on the displayed surface, displaying one or more indicators of a further parameter associated with the feature.

27. A method as described in example 26 wherein the one or more indicators comprise one or more of:

a. a representation of thermal image data overlaid on the representation of the three-dimensional model;

b. a representation of fluorescence image data overlaid on the representation of the three-dimensional model;

c. a representation of texture image data overlaid on the representation of the three-dimensional model; and d. one or more wound dimensions.

28. A method of assessing a patient's skin including:

projecting UV light onto a patient's skin surface during a first time period;

capturing a plurality of images of the patient's skin surface over at least a second time period immediately following the first time period;

analysing fluorescence in each of the plurality of images to determine a fluorescence lifetime or fluorescence decay profile.

29. A device configured to perform any one of the examples 1-28.

30. A device comprising a memory and a processor, the memory storing instructions configured to cause the processor to perform any one of the examples 1-28.

31. A system configured to perform any one of the examples 1-28.

32. A system comprising a memory and a processor, the memory storing instructions configured to cause the processor to perform any one of the examples 1-28.

33. A handheld skin assessment device including:

a three-dimensional image capture unit;

a thermal image capture unit;

the device having a desired capture range at which three-dimensional image data and thermal image data of a patient's skin surface will be captured by the three-dimensional image capture unit and the thermal image capture unit; and a guide arrangement configured to guide the user to position the device at the desired capture range from the patient's skin surface.

34. A handheld skin assessment device including:

a UV light source;

a three-dimensional image capture unit;

the device having a desired capture range at which three-dimensional image data and fluorescence image data of a patient's skin surface will be captured; and a guide arrangement configured to guide the user to position the device at the desired capture range from the patient's skin surface.

35. A device as described in example 34 wherein fluorescence image data is captured by the three-dimensional image capture unit.

36. A device as described in either example 34 or 35 including a fluorescence camera, wherein the fluorescence image data is captured by the fluorescence camera.

37. A device as described in any one of examples 34-36, including one or more optical filters arranged to filter light during capture of the fluorescence image data.

38. A handheld skin assessment device including:

a source of UV light arranged, in use, to project UV light onto a patient's skin surface;

an image capture device configured to capture a plurality of image frames of the patient's skin surface, at an image frame capture rate; and electronics configured to modulate the UV light at a function of the image frame capture rate.

39. A handheld skin assessment device including:

a UV light source arranged, in use, to project UV light onto a patient's skin surface;

a three-dimensional image capture device arranged, in use, to capture three-dimensional image data of the patient's skin surface;

a controller configured to control at least the UV light source and the three-dimensional image capture device to capture:

a three-dimensional image data set with the UV light source off; and a fluorescence image data set with the UV light source on.

40. A device as described in example 39, including a processor configured to determine one or more range values from the three-dimensional image data, and to correct intensity values in the fluorescence image data set based on the one or more range values.

41. A device as described in example 39 or 40 wherein fluorescence image data is captured by the three-dimensional image capture unit.

42. A device as described in any one of examples 39-41 including a fluorescence camera, wherein the fluorescence image data is captured by the fluorescence camera.

43. A device as described in any one of examples 39-42, including one or more optical filters arranged to filter light during capture of the fluorescence image data.

While the present technology has been illustrated by the description of the embodiments thereof, and while the embodiments have been described in detail, it is not the intention of the Applicant to restrict or in any way limit the scope of the appended claims to such detail. Additional advantages and modifications will readily appear to those skilled in the art. Therefore, the present technology in its broader aspects is not limited to the specific details, representative apparatus and method, and illustrative examples shown and described. Accordingly, departures may be made from such details without departure from the spirit or scope of the Applicant's general inventive concept.

We claim:

1. A method of assessing a feature on a patient's skin surface, comprising:
   i capturing three-dimensional topographical image data of the patient's skin surface with a three-dimensional camera;
   ii. processing the captured image data to form a three-dimensional topographical data set representative of the patient's skin surface,
   iii. determining a boundary of the feature in the three-dimensional topographical data set;
   iv. determining, with a processor, a three-dimensional surface area of the feature within the boundary;
   v. identifying a plurality of sub-regions within the boundary;
   vi. identifying one or more tissue types in each of the sub-regions; and
   vii. receiving a user input manually adjusting one or more of the identified sub-regions.

2. The method of claim 1 wherein identifying the plurality of sub-regions includes automatically identifying, with a processor, the plurality of sub-regions.

3. The method of claim 2 wherein automatically identifying the plurality of sub-regions includes analyzing one or more of
   a. the three-dimensional topographical data set;
   b. thermal image data;
   fluorescence image data; and
   d. texture image data.

4. The method of claim 1 wherein identifying the plurality of sub-regions includes receiving, via a user interface, a user input manually identifying the plurality of sub-regions.

5. The method of claim 1 wherein identifying the plurality of sub-regions includes
   receiving, via a user interface, a user input manually identifying one or more of the plurality of sub-regions; and
   automatically identifying, with a processor, one or more others of the plurality of sub-regions.

6. The method of claim 1 wherein the method further comprises determining, for each sub-region of the plurality of sub-regions, a proportion of a surface area of that sub-region occupied by each tissue type identified in that sub-region.

7. The method of claim 1 wherein the method further comprises:
   determining, for each sub-region of the plurality of sub-regions, a proportion of a surface area of that sub-region occupied by each tissue type identified in that sub-region;
   determining a surface area of each sub-region of the plurality of sub-regions; and
   aggregating the determined proportions of tissue types to determine one or more of (a) an aggregated surface area occupied by each tissue type, and (b) an aggregated proportion of the surface area of the feature occupied by each tissue type.

8. The method of claim 1 wherein the method further comprises:
   determining, for each sub-region of the plurality of sub-regions, a proportion of a surface area of that sub-region occupied by each tissue type identified in that sub-region;
   determining a surface area of each sub-region of the plurality of sub-regions; and
   aggregating the determined proportions of tissue types and aggregating the tissue types into tissue classes, to determine one or more of (a) an aggregated surface area occupied by each tissue class, and (b) an aggregated proportion of the surface area of the feature occupied by each tissue class.

9. The method of claim 8 wherein the tissue classes include a viable tissue class and a non-viable tissue class.

10. The method of claim 1 wherein the feature is a wound and the surface area is a wound bed area.

11. The method of claim 1 wherein receiving the user input manually adjusting the one or more of the identified sub-regions includes:
    displaying, via a user interface, data indicative of at least the one or more of the identified sub-regions to be adjusted; and
    receiving, via the user interface, a user manipulation of the displayed data.

12. The method of claim 1 wherein the method further includes displaying the identified sub-regions and overlaying previously gathered data for one or more of the identified sub-regions.

13. The method of claim 1 wherein the method further comprises monitoring trends in tissue type area or proportions over time.

14. The method of claim 1 wherein the method further comprises displaying tissue type area or proportions, or tissue class area or proportions.

15. A method of assessing a feature on a patient's skin surface, comprising:
    i. capturing three-dimensional topographical image data of the patient's skin surface with a three-dimensional camera;
    ii. processing the captured image data to form a three-dimensional topographical data set representative of the patient's skin surface,
    iii. determining a boundary of the feature in the three-dimensional topographical data set;
    iV. determining with a processor a three-dimensional surface area of the feature within the boundary; and v. identifying a plurality of sub-regions within the boundary and identifying one or more tissue types in each sub-region, wherein identifying the plurality of sub-regions includes receiving, via a user interface, a user input manually identifying one or more of the plurality of sub-regions; and automatically identifying, with a processor, one or more others of the plurality of sub-regions.

16. A method of assessing a feature on a patient's skin surface, comprising:
   i. capturing three-dimensional topographical image data of the patient's skin surface with a three-dimensional camera;
   ii. processing the captured image data to form a three-dimensional topographical data set representative of the patient's skin surface,
   iii. determining a boundary of the feature in the three-dimensional topographical data set;
   iv. determining, with a processor, a three-dimensional surface area of the feature within the boundary;
   v. identifying a plurality of sub-regions within the boundary;
   vi. identifying one or more tissue types in each sub-region; and
   vii. based at least in part on the identified tissue types, determining and displaying an indicator of complexity of the feature.

17. The method of claim 16 wherein the method further comprises monitoring trends in the complexity over time.

18. The method of claim 16 wherein determining the indicator of complexity is based at least in part on proportions of the identified tissue types.

19. The method of claim 16 wherein the method further comprises:
   determining for each sub-region a proportion of a surface area of that sub-region occupied by each tissue type identified in that sub-region;
   determining a surface area of each sub-region; and
   aggregating the determined proportions of tissue types to determine one or more of (a) an aggregated surface area occupied by each tissue type and (b) an aggregated proportion of the surface area of the feature occupied by each tissue type, wherein the indicator of complexity is determined based on the identified tissue types and their aggregated proportions.

* * * * *

UNITED STATES PATENT AND TRADEMARK OFFICE
CERTIFICATE OF CORRECTION

PATENT NO. : 11,903,723 B2
APPLICATION NO. : 16/500785
DATED : February 20, 2024
INVENTOR(S) : Philip John Barclay et al.

It is certified that error appears in the above-identified patent and that said Letters Patent is hereby corrected as shown below:

On the Title Page

On Page 6, Column 2, Line 33, delete "Berriss" and insert -- Berries --, therefor.

On page 6, Column 2, Line 35, delete "Berriss," and insert -- Berries, --, therefor.

On page 7, Column 1, Line 19, delete "Eoidemiol" and insert -- Epidemiol --, therefor.

On page 7, Column 1, Line 49, delete "JWound" and insert -- Wound --, therefor.

On page 7, Column 1, Line 59, delete "Malanoma" and insert -- Melanoma --, therefor.

On page 7, Column 2, Line 70, delete "Lasres" and insert -- Lasers --, therefor.

On page 8, Column 1, Line 30, delete "I 107" and insert -- 1107 --, therefor.

In the Specification

In Column 8, Line 55, delete "of the of the" and insert -- of the --, therefor.

In Column 12, Line 32, delete "surface" and insert -- surface. --, therefor.

In Column 12, Line 33, delete "map" and insert -- map. --, therefor.

In Column 15, Line 45, delete "Pseudomanas" and insert -- Pseudomonas --, therefor.

In Column 15, Line 48, delete "diptheriae," and insert -- diphtheria, --, therefor.

In Column 22, Line 34, delete "dike" and insert -- (like --, therefor.

Signed and Sealed this
Thirtieth Day of April, 2024

Katherine Kelly Vidal
*Director of the United States Patent and Trademark Office*

CERTIFICATE OF CORRECTION (continued)
U.S. Pat. No. 11,903,723 B2

In Column 28, Lines 33-34, delete "picoprojectors" and insert -- pico projectors --, therefor.

In the Claims

In Column 37, Line 30, Claim 1, delete "i" and insert -- i. --, therefor.

In Column 37, Line 35, Claim 1, delete "surface," and insert -- surface; --, therefor.

In Column 37, Line 54, Claim 3, before "fluorescence" insert -- c. --.

In Column 38, Line 63, Claim 15, delete "surface," and insert -- surface; --, therefor.

In Column 38, Line 66, Claim 15, delete "iV." and insert -- iv. --, therefor.

In Column 39, Line 18, Claim 16, delete "surface," and insert -- surface; --, therefor.